United States Patent
Liu et al.

(10) Patent No.: US 12,414,464 B2
(45) Date of Patent: Sep. 9, 2025

(54) ORGANIC COMPOUND AND APPLICATION THEREOF

(71) Applicants: Wuhan Tianma Microelectronics Co., Ltd., Wuhan (CN); Wuhan Tianma Microelectronics Co., Ltd. Shanghai Branch, Shanghai (CN)

(72) Inventors: Ying Liu, Wuhan (CN); Dong Jiang, Wuhan (CN); Dongyang Deng, Wuhan (CN); Wei Gao, Wuhan (CN)

(73) Assignees: Wuhan Tianma Microelectronics Co., Ltd., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 731 days.

(21) Appl. No.: 17/845,004

(22) Filed: Jun. 21, 2022

(65) Prior Publication Data
US 2022/0328770 A1    Oct. 13, 2022

(30) Foreign Application Priority Data
Feb. 15, 2022    (CN) .......................... 202210137557.4

(51) Int. Cl.
| | |
|---|---|
| H10K 85/60 | (2023.01) |
| C07D 493/10 | (2006.01) |
| C07D 495/10 | (2006.01) |
| C07D 498/10 | (2006.01) |
| C09K 11/06 | (2006.01) |
| H10K 50/11 | (2023.01) |
| H10K 101/10 | (2023.01) |

(52) U.S. Cl.
CPC ....... *H10K 85/6574* (2023.02); *C07D 493/10* (2013.01); *C07D 495/10* (2013.01); *C07D 498/10* (2013.01); *C09K 11/06* (2013.01); *H10K 85/654* (2023.02); *H10K 85/657* (2023.02); *H10K 85/6572* (2023.02); *C09K 2211/1018* (2013.01); *H10K 50/11* (2023.02); *H10K 2101/10* (2023.02)

(58) Field of Classification Search
CPC .... C09K 11/06; C07D 493/10; C07D 495/10; C07D 497/10; C07D 513/10
See application file for complete search history.

(56) References Cited

U.S. PATENT DOCUMENTS

2014/0225040 A1* 8/2014 Parham ................ C07D 405/04
544/70

FOREIGN PATENT DOCUMENTS

CN    110240594 A    9/2019

\* cited by examiner

*Primary Examiner* — Sean M DeGuire
(74) *Attorney, Agent, or Firm* — KDW FIRM PLLC

(57) ABSTRACT

Provided are an organic compound and an application thereof The organic compound of the present disclosure has a structure similar to a spiro ring. The structure can enable the compound to obtain relatively high thermal stability and a relatively high glass transition temperature Tg. The skeleton has an electron-donating ability, and a group having an electron withdrawing ability is linked to the skeleton so that the skeleton has the electron withdrawing ability, which is more conducive to the transport and recombination of electrons and holes in this region. The compound having the structure similar to the spiro ring also has suitable steric distortion and can reduce a molecular acting force and intermolecular stacking, which is conducive to reducing concentration quenching and efficiency roll-off and preparing an organic light-emitting diode (OLED) device. Therefore, the compound of the present disclosure also enables the device to achieve a longer lifetime.

14 Claims, 1 Drawing Sheet

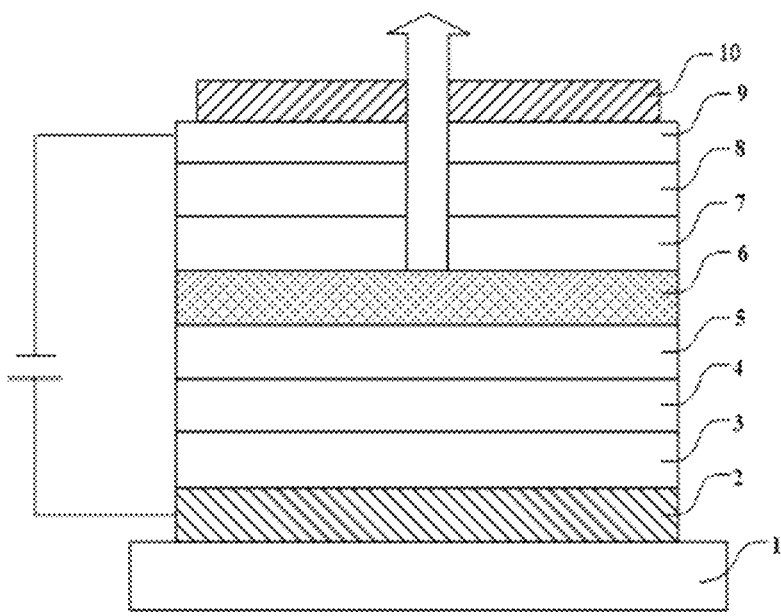

ORGANIC COMPOUND AND APPLICATION THEREOF

CROSS-REFERENCE TO RELATED APPLICATION(S)

This application claims priority to Chinese Patent Application No. CN 202210137557.4 filed Feb. 15, 2022, the disclosure of which is incorporated herein by reference in its entirety.

TECHNICAL FIELD

The present disclosure belongs to the field of organic electroluminescent materials and relates to an organic compound and an application thereof.

BACKGROUND

Organic electroluminescent materials (such as organic light-emitting diodes (OLEDs)), as a new generation of display technology, have the advantages of ultra-thinness, self-luminescence, a wide viewing angle, a fast response, high luminescence efficiency, good temperature adaptability, a simple manufacturing process, a low driving voltage, low energy consumption and the like and have been widely applied to flat-panel display, flexible display, solid-state lighting, vehicle display and other industries.

The organic electroluminescent materials can be divided into electrofluorescence and electrophosphorescence according to a luminescence mechanism, where fluorescence is the radiative decay and transition of singlet excitons while phosphorescence is light emitted during the radiative decay of triplet excitons to a ground state. According to the theory of spin quantum statistics, singlet excitons and triplet excitons are formed at a ratio of 1:3. A fluorescent material has an internal quantum efficiency lower than or equal to 25% and an external quantum efficiency which is generally lower than 5%. An electrophosphorescent material has an internal quantum efficiency of 100% in theory and an external quantum efficiency which can reach 20%. In 1998, Prof. Ma Yuguang of Jilin University, China, and Prof. Forrest of Princeton University, USA, reported that an osmium complex and a platinum complex were doped as dyes into a light-emitting layer separately. They have successfully obtained and explained the phenomenon of phosphorescent electroluminescence for the first time and pioneered the application of the prepared phosphorescent material to an electroluminescent device.

CN112979536A discloses a phosphorescent host material, a preparation method thereof and an organic electroluminescent device. The phosphorescent host material may be used as a light-emitting layer material of the organic electroluminescent device and can reduce the driving voltage of an optoelectronic device, significantly improve the luminescence efficiency of the optoelectronic device, and prolong the service life of the optoelectronic device.

CN112778293A discloses an organic electrophosphorescent host material and an application thereof to an organic electroluminescent device. The organic electroluminescent material has good optoelectronic performance and is suitable for use as a host material or a blue light-emitting material in the organic electroluminescent device which has higher device efficiency and a longer service life. Meanwhile, the compound in CN112778293A has very good thermal stability and film formability and a glass transition temperature as high as 139° C. The organic electroluminescent device has the advantages of a low turn-on voltage, high efficiency, good stability and a long lifetime.

CN107311978A discloses a phosphorescent host material, a preparation method thereof and an organic light-emitting device using the material. The phosphorescent host material is a fluorene compound containing pyridyl and carbazolyl and has the characteristics of a wide energy gap, a high glass transition temperature and a small concentration quenching effect.

However, phosphorescent host materials including the above materials still have many deficiencies in terms of luminescence performance, usage stability and machining performance and cannot meet the requirements for their applications as light-emitting materials to display devices. The overall performance of the phosphorescent host materials is still to be improved and balanced to a large extent.

Therefore, it is a research focus in the art to develop a compound that can increase a carrier transport rate and balance carrier transport performance to improve luminescence efficiency for the compound to be better applied in the field of electroluminescence technology.

SUMMARY

The present disclosure provides an organic compound and an application thereof

A first aspect of the present disclosure is to provide an organic compound, wherein the organic compound has a structure represented by Formula I:

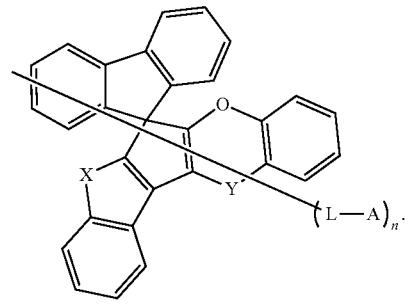

Formula I

In Formula I, L is independently selected from a single bond, substituted or unsubstituted C6 to C30 aryl, or substituted or unsubstituted C5 to C30 heteroaryl;

A is independently selected from cyano, substituted or unsubstituted C6 to C40 arylamine, or substituted or unsubstituted C5 to C30 heteroaryl;

X and Y are independently selected from O, S,

or M—R, wherein M is N, Si or B, and R is C1 to C10 linear or branched alkyl, C1 to C10 alkoxy, C6 to C20 aryl or C6 to C20 arylamino; and n is an integer from 1 to 16.

In the present disclosure, C6 to C30 may be C6, C7, C8, C9, C10, C12, C13, C14, C15, C16, C18, C20, C22, C24, C26, C28 or C30, etc.

C6 to C40 may be C6, C7, C8, C9, C10, C12, C13, C14, C15, C16, C18, C20, C22, C24, C26, C28, C30, C33, C36, C38 or C40, etc.

C6 to C20 may be C6, C7, C8, C9, C10, C12, C13, C14, C15, C16, C18 or C20, etc.

C5 to C30 may be C6, C7, C8, C9, C10, C12, C13, C14, C15, C16, C18, C20, C22, C24, C26, C28, C30, etc.

C1 to C10 may be C1, C2, C3, C4, C5, C6, C7, C8, C9 or C10.

In the present disclosure, n is an integer from 1 to 16, for example, 1, 2, 3, 5, 8, 9, 10, 12, 14 or 15, etc. In Formula I of the present disclosure, the -L-A group crosses the entire main structure, indicating that the group may be substituted at any substitutable position of the entire main structure.

The organic compound of the present disclosure has good thermal stability and film formability and an appropriate glass transition temperature Tg, which is conducive to forming a stable and uniform thin film during thermal vacuum evaporation and reducing phase separation, maintaining the stability of a device. The organic compound has a relatively high carrier transport rate and balanced carrier transport performance, which is conducive to the balance of hole and electron transport in the device and obtaining a relatively wide carrier recombination region, improving luminescence efficiency.

A second aspect of the present disclosure is to provide an organic electroluminescent material including the organic compound as described in the first aspect.

A third aspect of the present disclosure is to provide a light-emitting layer material including the organic compound as described in the first aspect.

A fourth aspect of the present disclosure is to provide an OLED device including an anode, a cathode and an organic thin film layer disposed between the anode and the cathode, wherein a material of the organic thin film layer includes the organic compound as described in the first aspect.

A fifth aspect of the present disclosure is to provide a display panel including the OLED device as described in the fourth aspect.

A sixth aspect of the present disclosure is to provide an organic light-emitting display device including the display panel as described in the fifth aspect.

Compared with the related art, the present disclosure has the beneficial effects described below.

The organic compound of the present disclosure has a structure similar to a spiro ring. The structure can enable the compound to obtain relatively high thermal stability and a relatively high glass transition temperature Tg. The skeleton has an electron-donating ability, and a group having an electron withdrawing ability is linked to the skeleton so that the skeleton has the electron withdrawing ability, which is more conducive to the transport and recombination of electrons and holes in this region. The compound having the structure similar to the spiro ring also has suitable steric distortion and can reduce a molecular acting force and intermolecular stacking, which is conducive to reducing concentration quenching and efficiency roll-off and preparing the OLED device. Therefore, the compound of the present disclosure also enables the device to achieve a longer lifetime.

BRIEF DESCRIPTION OF DRAWINGS

FIG. 1 is a structure diagram of an organic light-emitting device according to the present disclosure, where the direction of an arrow represents a light emission direction of the device.

REFERENCE LIST 1 substrate
2 ITO anode
3 first hole transport layer
4 second hole transport layer
5 electron blocking layer
6 light-emitting layer
7 first electron transport layer
8 second electron transport layer
9 cathode
10 capping layer

DETAILED DESCRIPTION

Technical solutions of the present disclosure are further described below through embodiments. It is to be understood by those skilled in the art that the embodiments described herein are used for a better understanding of the present disclosure and are not to be construed as specific limitations to the present disclosure.

A first aspect of the present disclosure is to provide an organic compound, where the organic compound has a structure represented by Formula I:

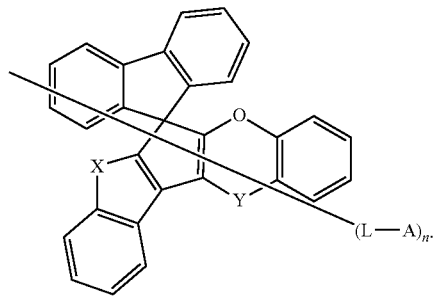

Formula I

In Formula I, L is independently selected from a single bond, substituted or unsubstituted C6 to C30 aryl, or substituted or unsubstituted C5 to C30 heteroaryl;

A is independently selected from cyano, substituted or unsubstituted C6 to C40 arylamine, or substituted or unsubstituted C5 to C30 heteroaryl;

X and Y are independently selected from O, S,

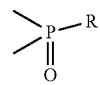

or M—R, wherein M is N, Si or B, and R is C1 to C10 linear or branched alkyl, C1 to C10 alkoxy, C6 to C20 aryl or C6 to C20 arylamino; and n is an integer from 1 to 16.

In the present disclosure, C6 to C30 may be C6, C7, C8, C9, C10, C12, C13, C14, C15, C16, C18, C20, C22, C24, C26, C28 or C30, etc.

C6 to C40 may be C6, C7, C8, C9, C10, C12, C13, C14, C15, C16, C18, C20, C22, C24, C26, C28, C30, C33, C36, C38 or C40, etc.

C6 to C20 may be C6, C7, C8, C9, C10, C12, C13, C14, C15, C16, C18 or C20, etc.

C5 to C30 may be C6, C7, C8, C9, C10, C12, C13, C14, C15, C16, C18, C20, C22, C24, C26, C28, C30, etc.

C1 to C10 may be C1, C2, C3, C4, C5, C6, C7, C8, C9 or C10.

In the present disclosure, n is an integer from 1 to 16, for example, 1, 2, 3, 5, 8, 9, 10, 12, 14 or 15, etc. In Formula I of the present disclosure, the -L-A group crosses the entire main structure, indicating that the group may be substituted at any substitutable position of the entire main structure.

In the present disclosure, when two or more -L-A groups are substituted on the main structure, L groups may be the same or different and A groups may be the same or different.

The organic compound of the present disclosure has good thermal stability and film formability and an appropriate glass transition temperature Tg, which is conducive to forming a stable and uniform thin film during thermal vacuum evaporation and reducing phase separation, maintaining the stability of a device. The organic compound has a relatively high carrier transport rate and balanced carrier transport performance, which is conducive to the balance of hole and electron transport in the device and obtaining a relatively wide carrier recombination region, improving luminescence efficiency.

In one embodiment, a substituent in the substituted C6 to C30 aryl, substituted C5 to C30 heteroaryl or substituted C6 to C40 arylamine is protium, deuterium, halogen, cyano, C1 to C10 (for example, C2, C4, C6, C7, C8 or C9) linear or branched alkyl, C1 to C10 (for example, C2, C4, C6, C7, C8 or C9) alkoxy, C6 to C20 (for example, C6, C7, C8, C9, C10, C12, C13, C14, C15, C16 or C18) aryl, or C6 to C20 (for example, C6, C7, C8, C9, C10, C12, C13, C14, C15, C16 or C18) arylamino.

In one embodiment, L is independently selected from a single bond, substituted or unsubstituted phenyl, substituted or unsubstituted biphenyl, substituted or unsubstituted naphthyl, or substituted or unsubstituted anthryl; and a substituent in the substituted group is selected from deuterium, tritium, cyano or phenyl.

In one embodiment, A is independently selected from cyano, substituted or unsubstituted diphenylamine, substituted or unsubstituted triphenylamine, substituted or unsubstituted carbazolyl, substituted or unsubstituted triazinyl, substituted or unsubstituted quinolyl or substituted or unsubstituted isoquinolyl; and a substituent in the substituted group is selected from protium, deuterium, halogen, cyano, C1 to C10 (for example, C2, C4, C6, C7, C8 or C9) linear or branched alkyl, C1 to C10 (for example, C2, C4, C6, C7, C8 or C9) alkoxy, C6 to C20 (for example, C6, C7, C8, C9, C10, C12, C13, C14, C15, C16 or C18) aryl or C6 to C20 (for example, C6, C7, C8, C9, C10, C12, C13, C14, C15, C16 or C18) arylamino.

In one embodiment, X and Y are independently selected from O or S.

In one embodiment, R is phenyl, pyridyl, biphenyl, pyridyl-phenyl, phenyl substituted with at least one cyano group, pyridyl substituted with at least one cyano group, biphenyl substituted with at least one cyano group or pyridyl-phenyl substituted with at least one cyano group.

In one embodiment, the organic compound has a structure represented by Formula II:

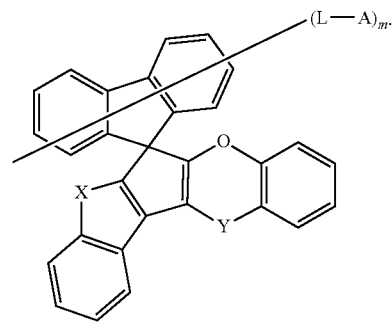

Formula II

In Formula II, L is independently selected from a single bond, substituted or unsubstituted C6 to C30 aryl, or substituted or unsubstituted C5 to C30 heteroaryl;

A is independently selected from cyano, substituted or unsubstituted C6 to C40 arylamine, or substituted or unsubstituted C5 to C30 heteroaryl;

X and Y are independently selected from O, S,

or M—R, wherein M is N, Si or B, and R is C1 to C10 linear or branched alkyl, C1 to C10 alkoxy, C6 to C20 aryl or C6 to C20 arylamino; and m is an integer from 1 to 8 (for example, may be 1, 2, 3, 4, 5, 6, 7 or 8).

In the compound of Formula II of the present disclosure, the -L-A group crosses a fluorenyl group in the main structure, indicating that the -L-A group is substituted at any substitutable position of the fluorenyl group.

In one embodiment, the organic compound is any one of the following compounds:

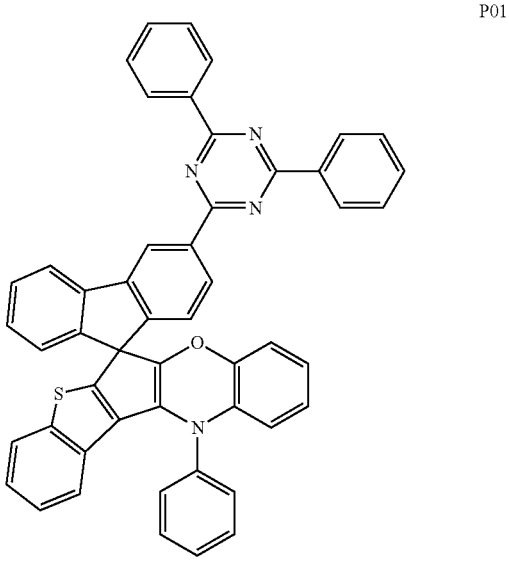

P01

P02
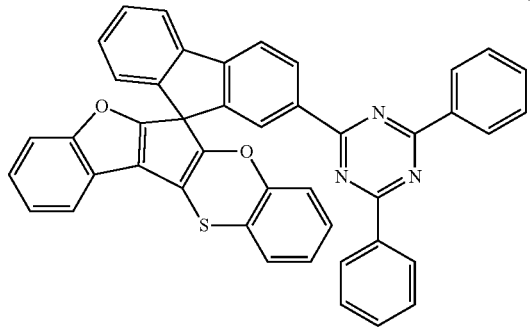
P03
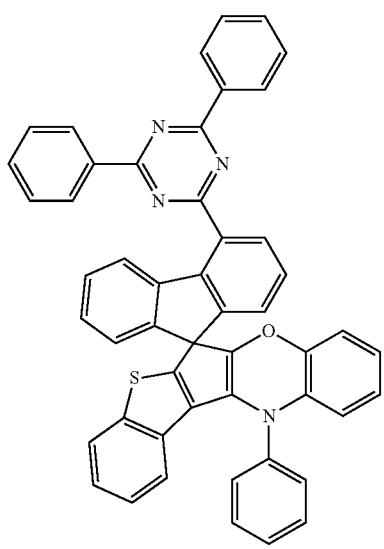
P04
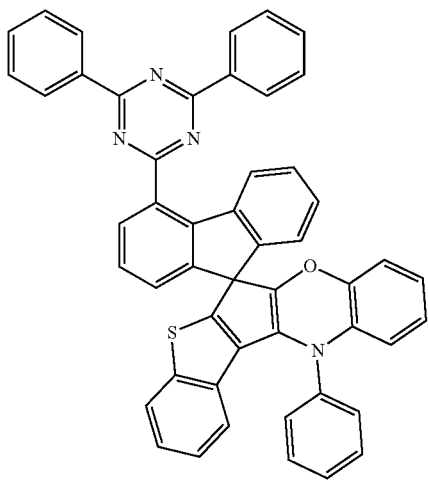
P05
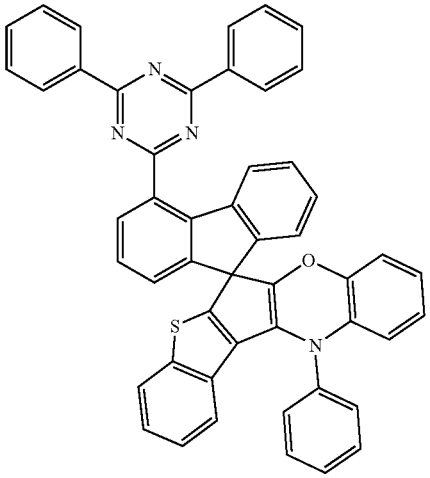
P06
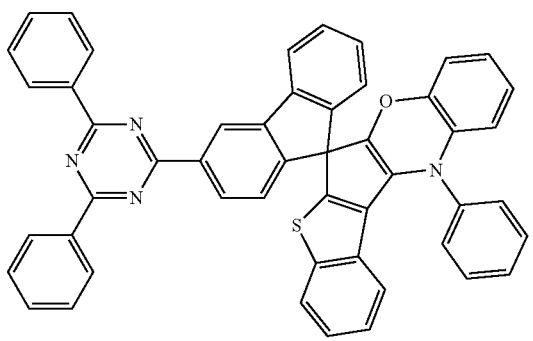
P07
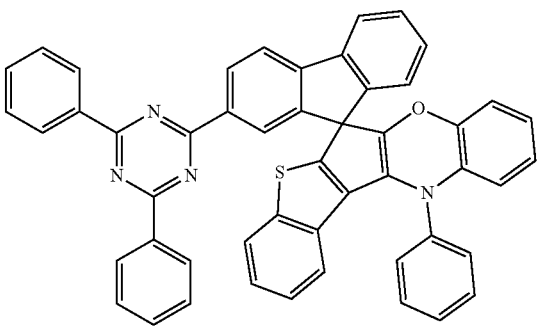
P08
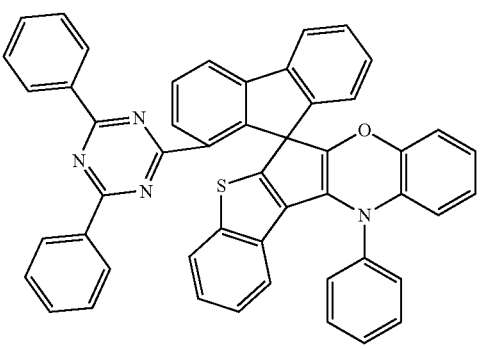

-continued
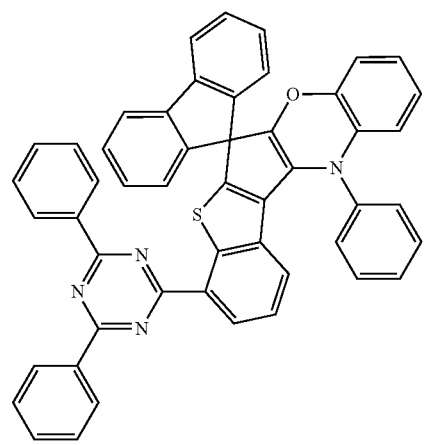
P09
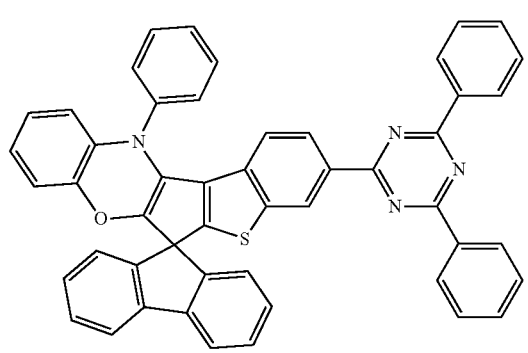
P10
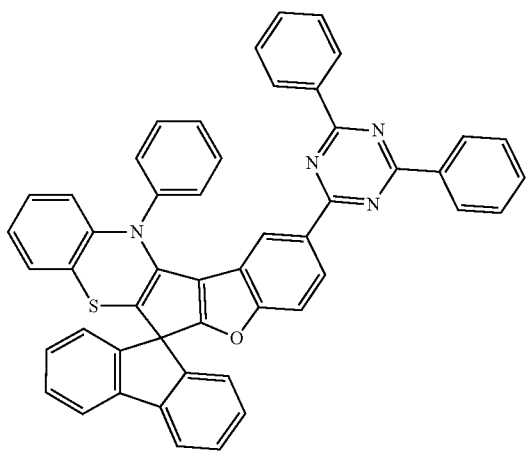
P11
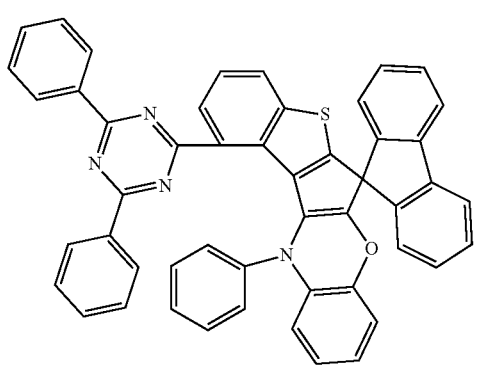
P12
-continued
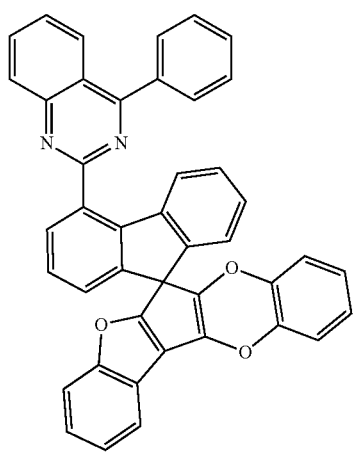
P13
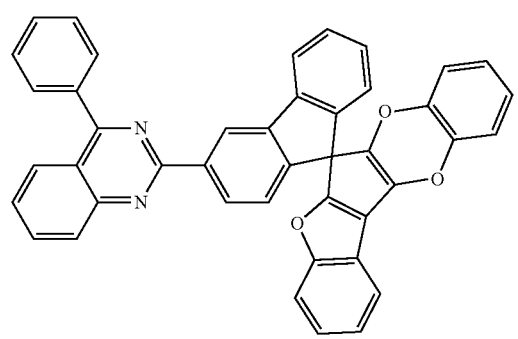
P14
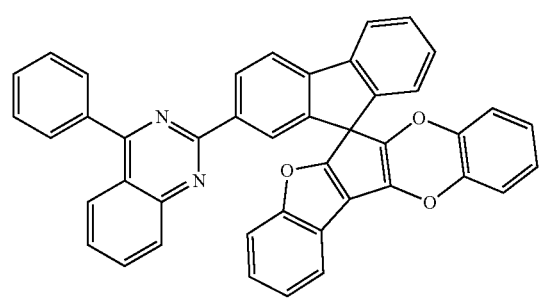
P15
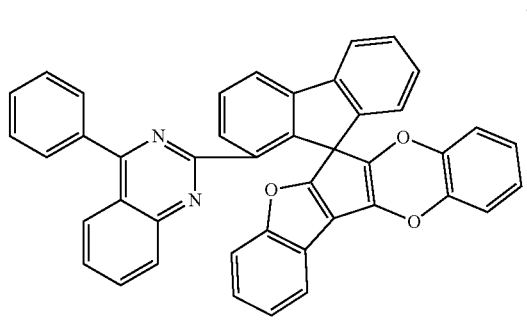
P16

P17
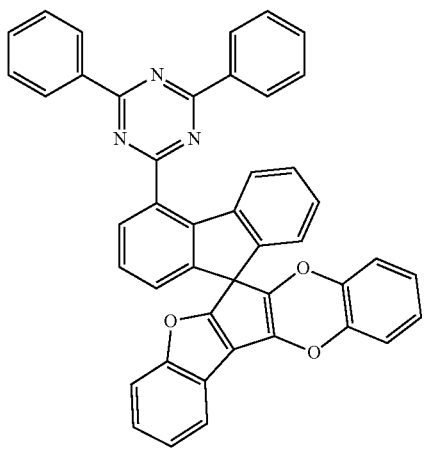
P18
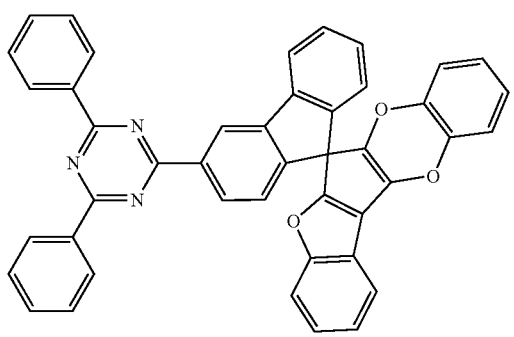
P19
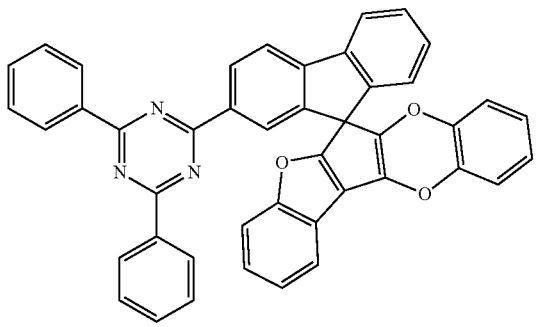
P20
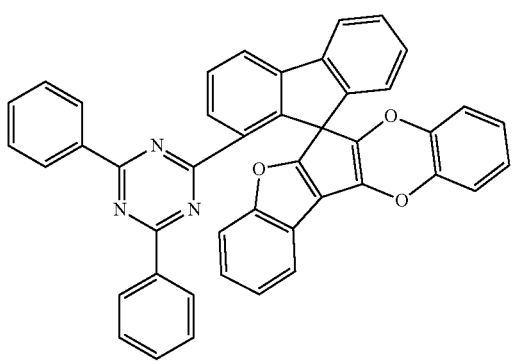
P21
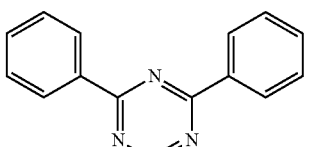
P22
P23
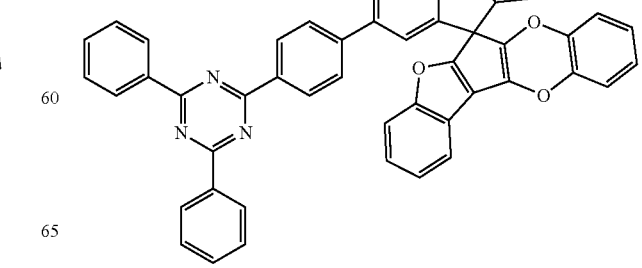

-continued
P24
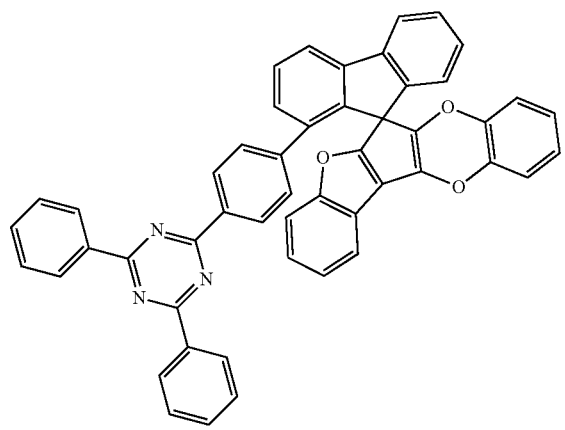
P25
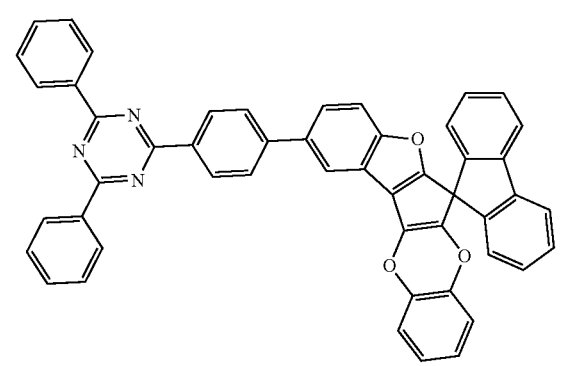
P26
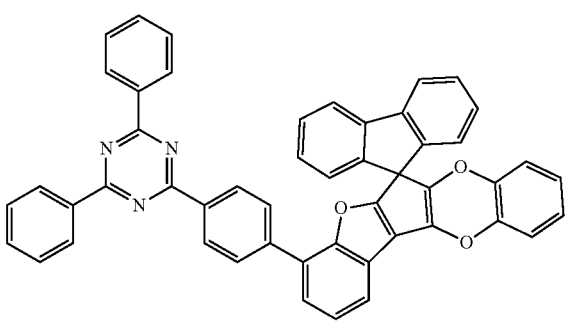
P27
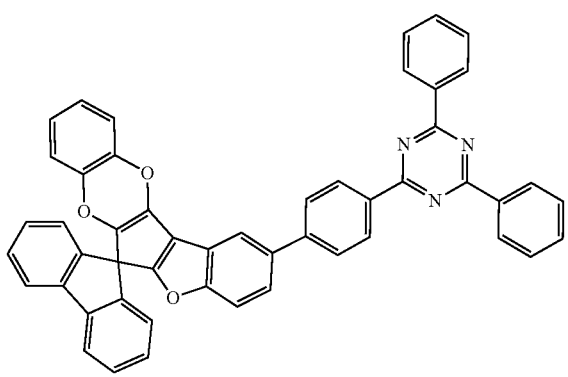
-continued
P28
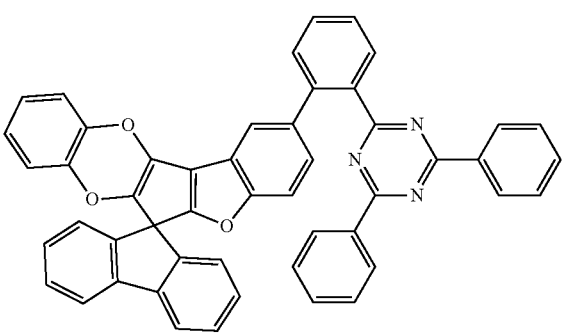
P29
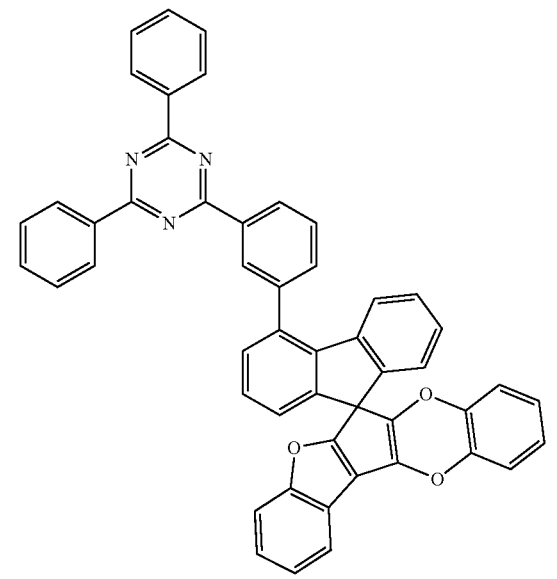
P30
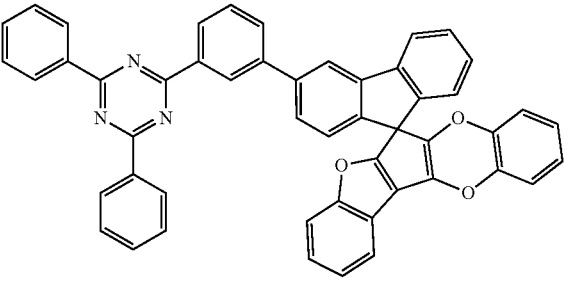
P31
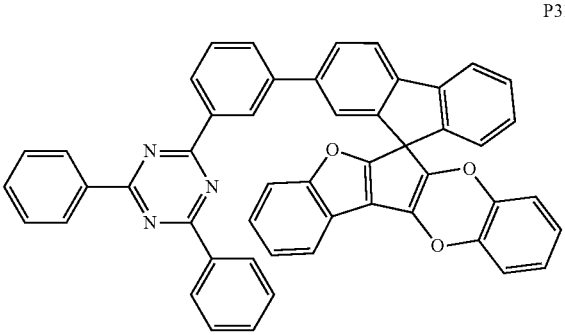

P32
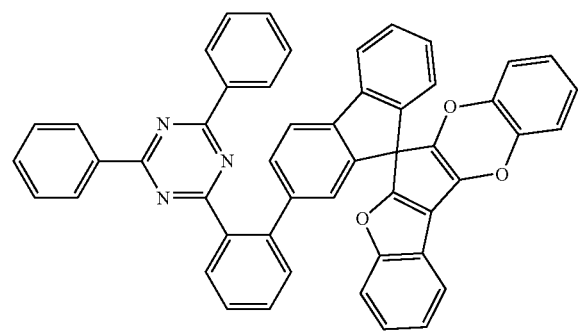
P36
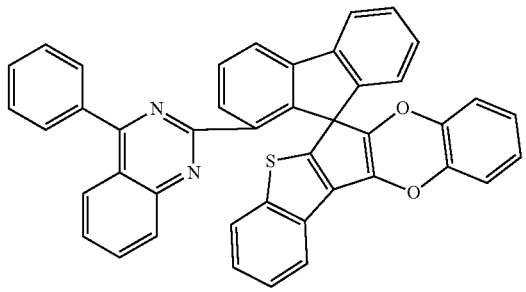
P33
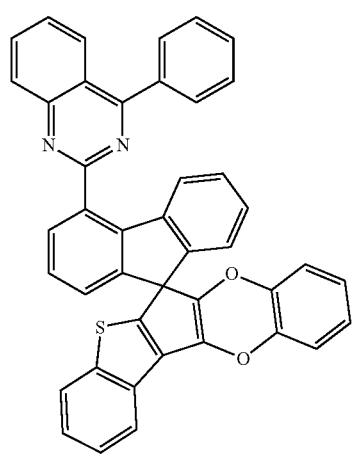
P37
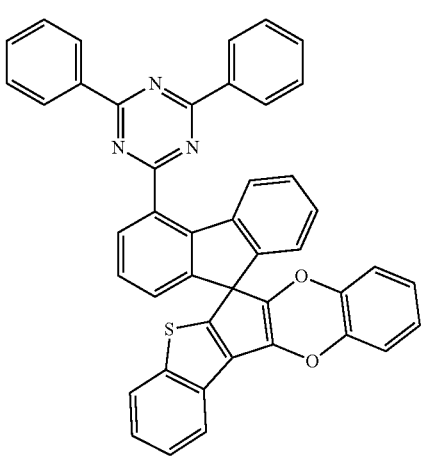
P34
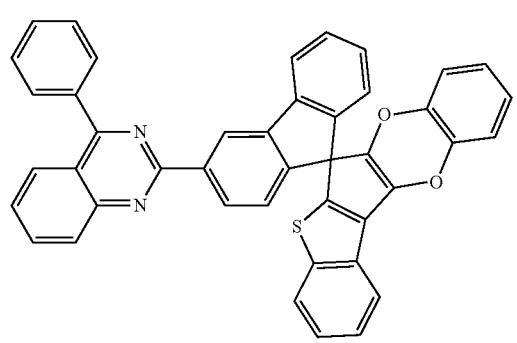
P38
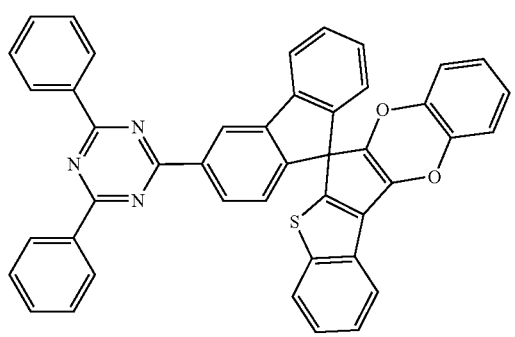
P35
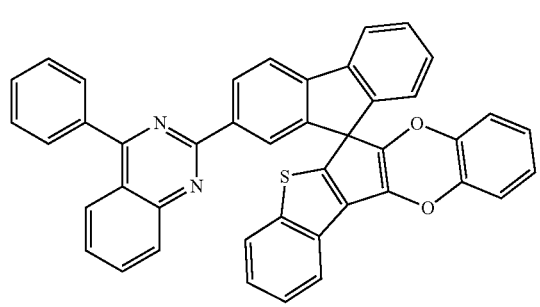
P39
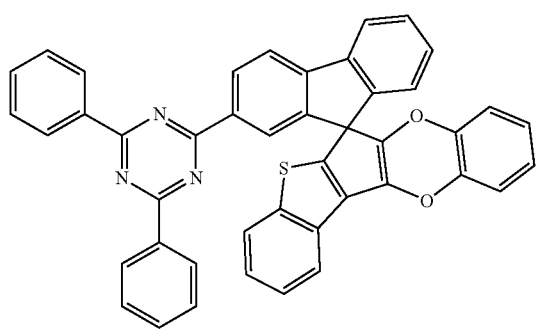

P40
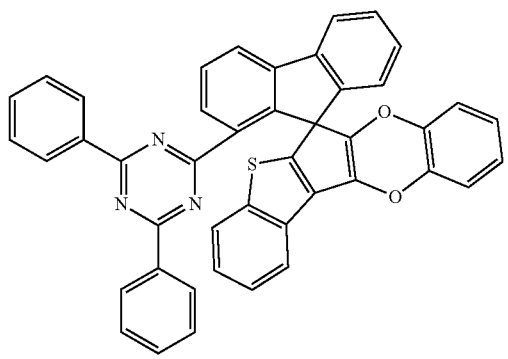
P41
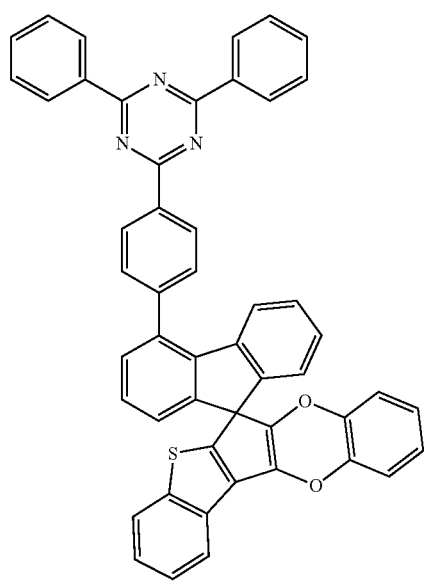
P42
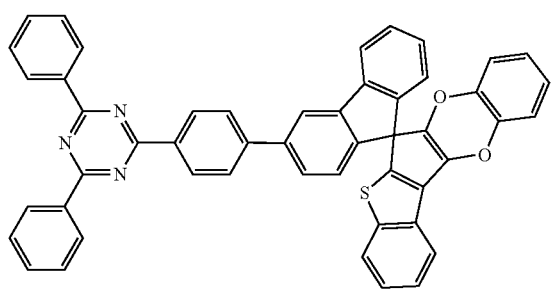
P43
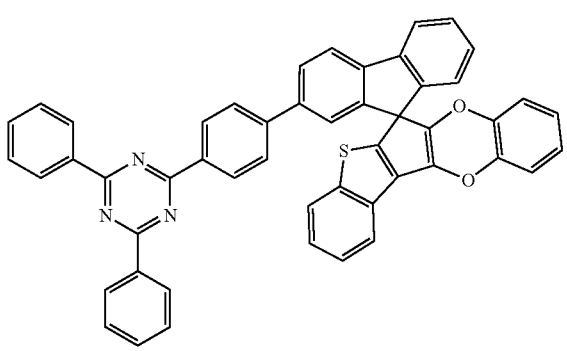
P44
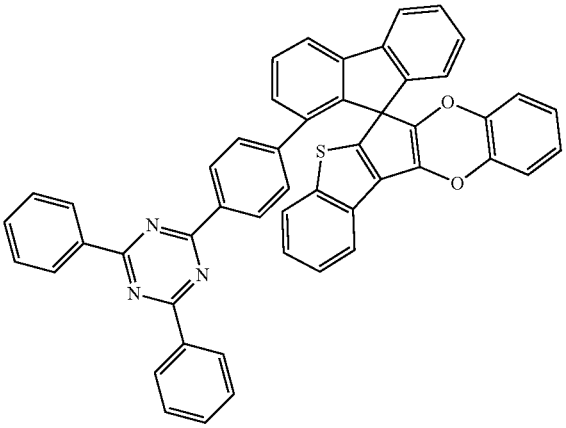
P45
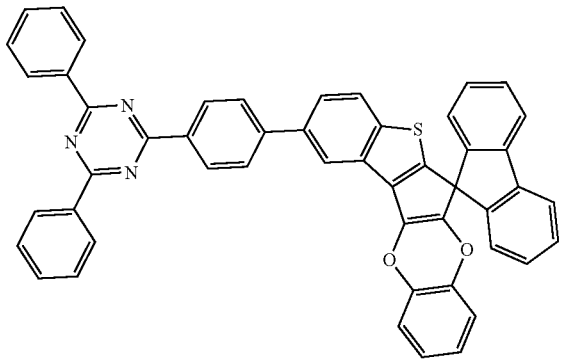
P46
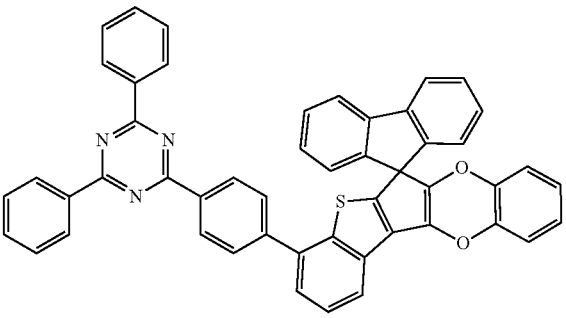
P47
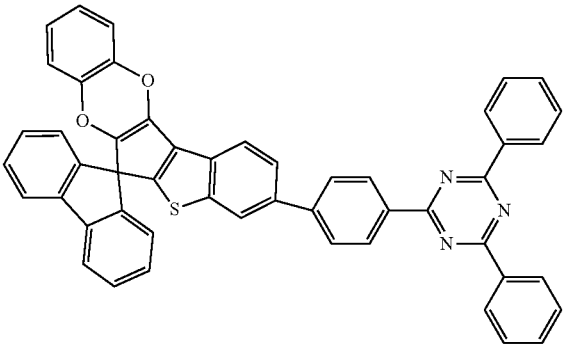

P48
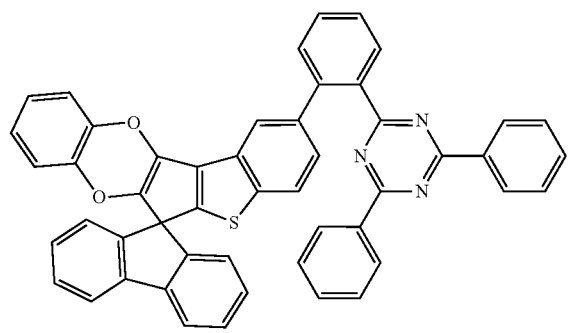
P49
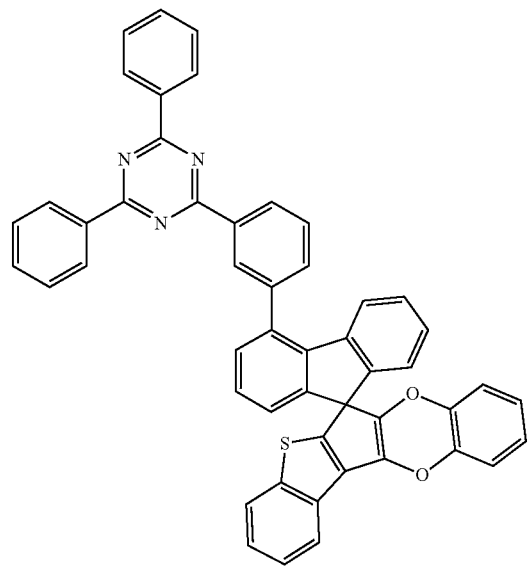
P50
P51
P52
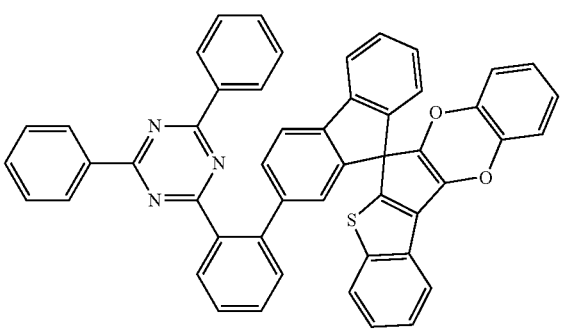
P53
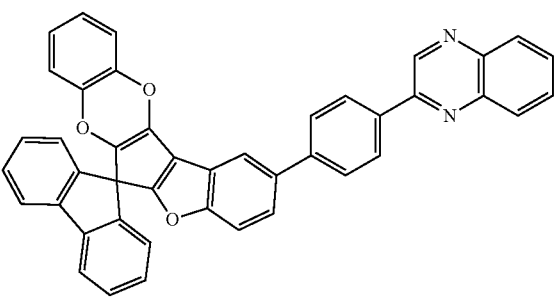
P54
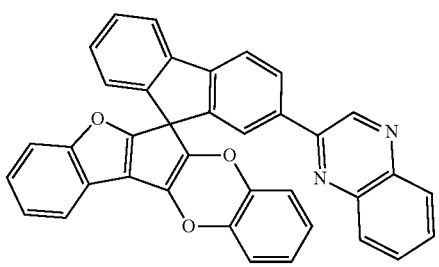
P55
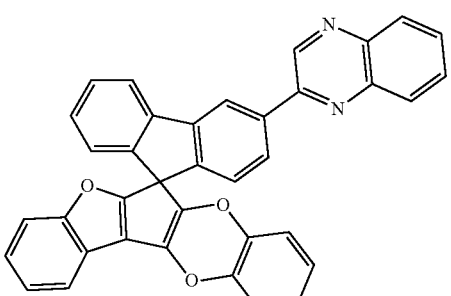
P56
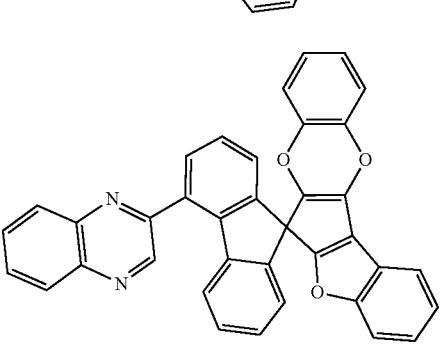

P57
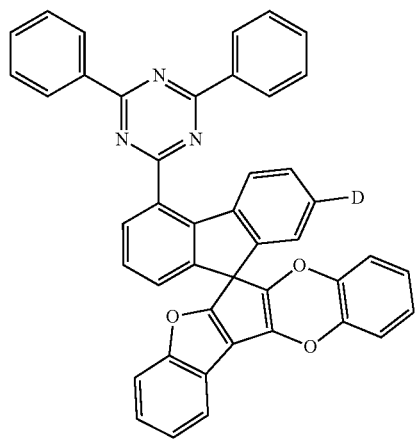
P58
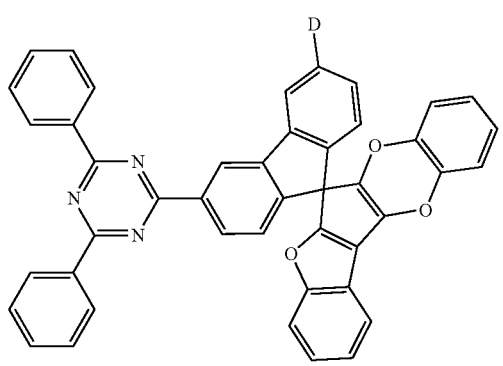
P59
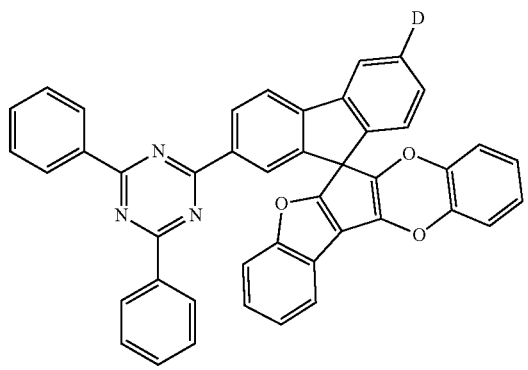
P60
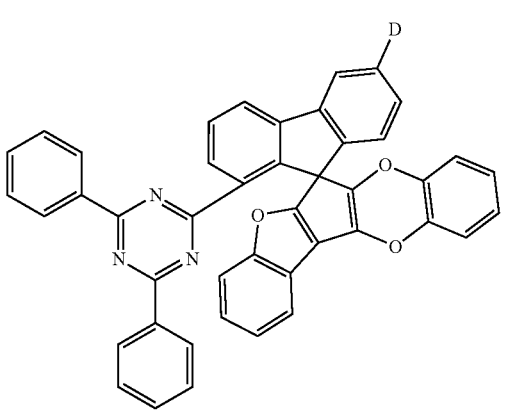
P61
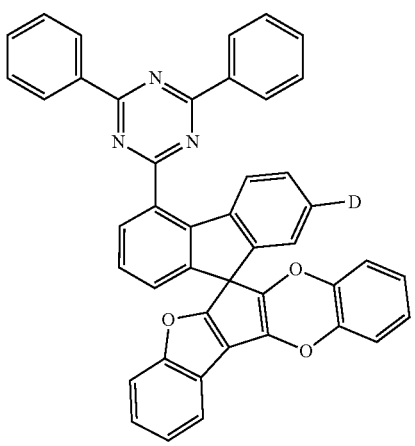
P62
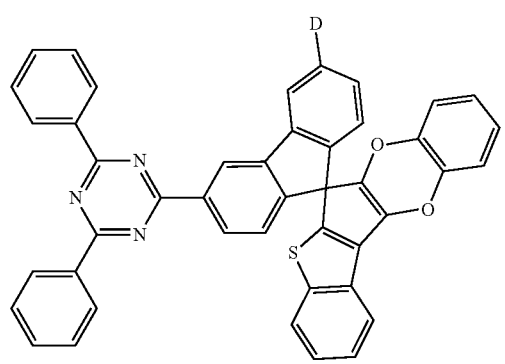
P63
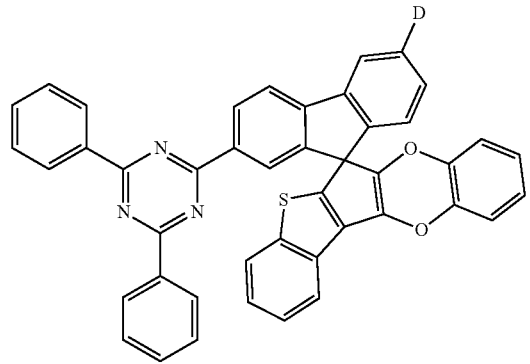
P64
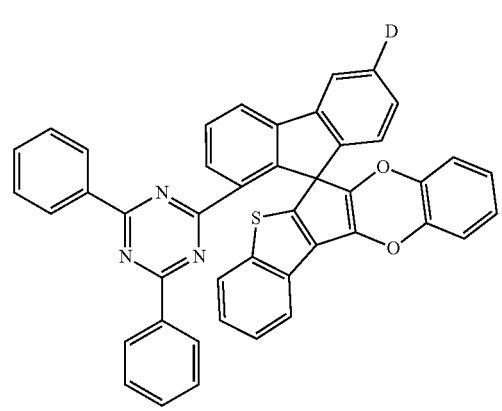

P65
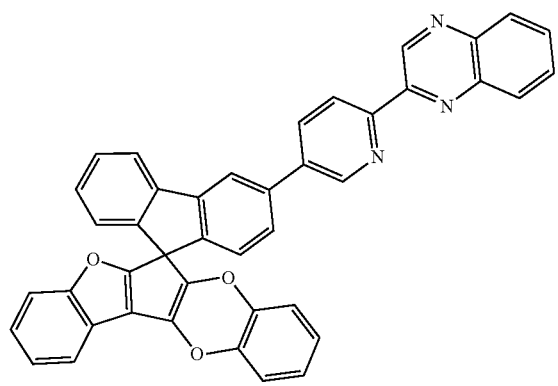
P66
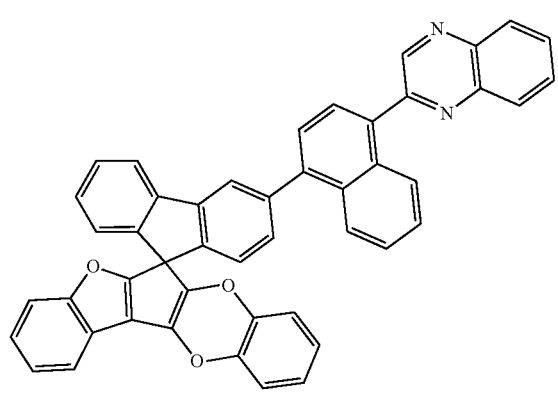
P67
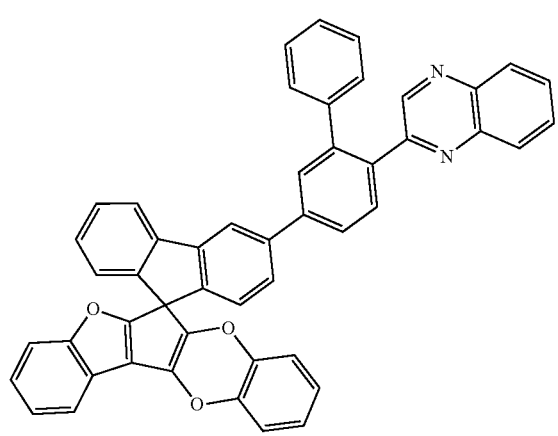
P68
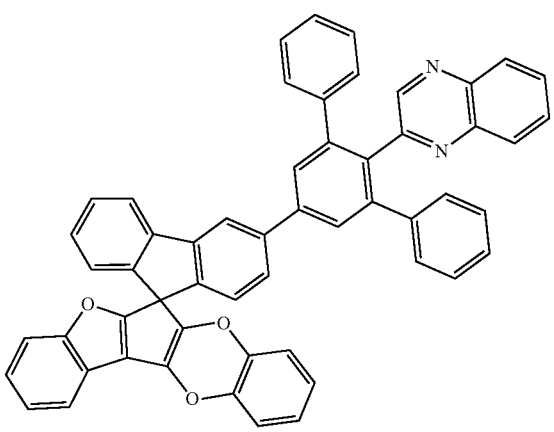
P69
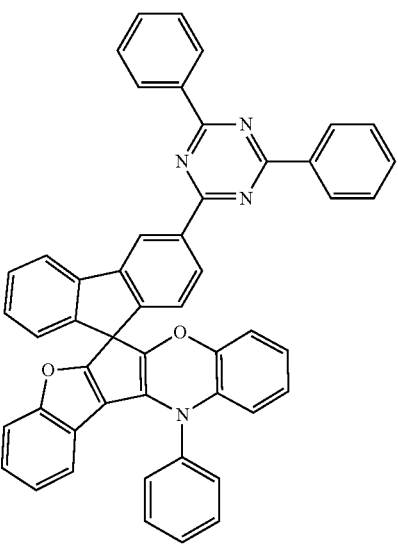
P70
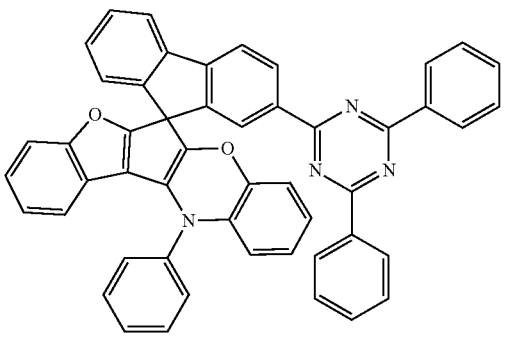

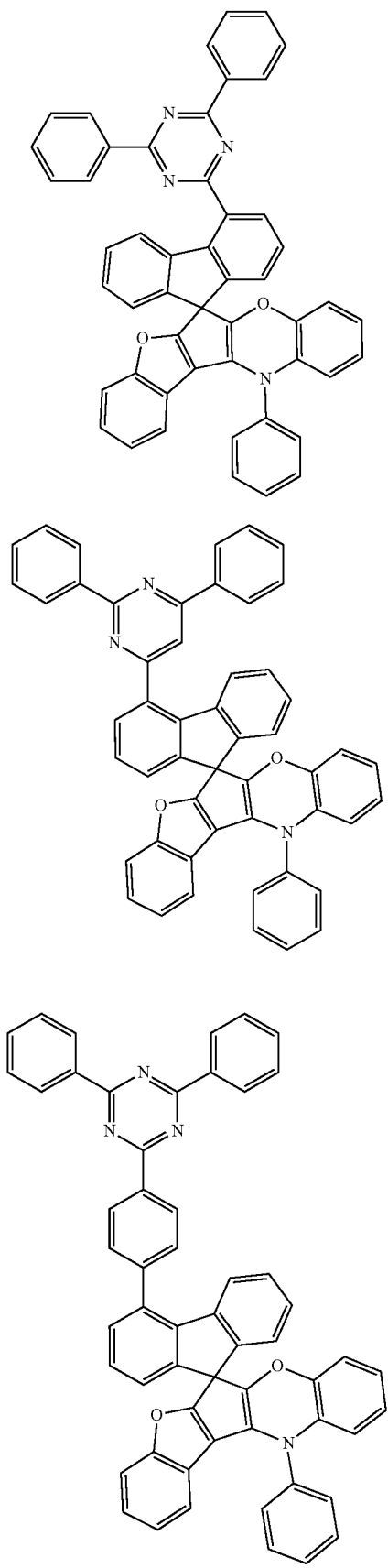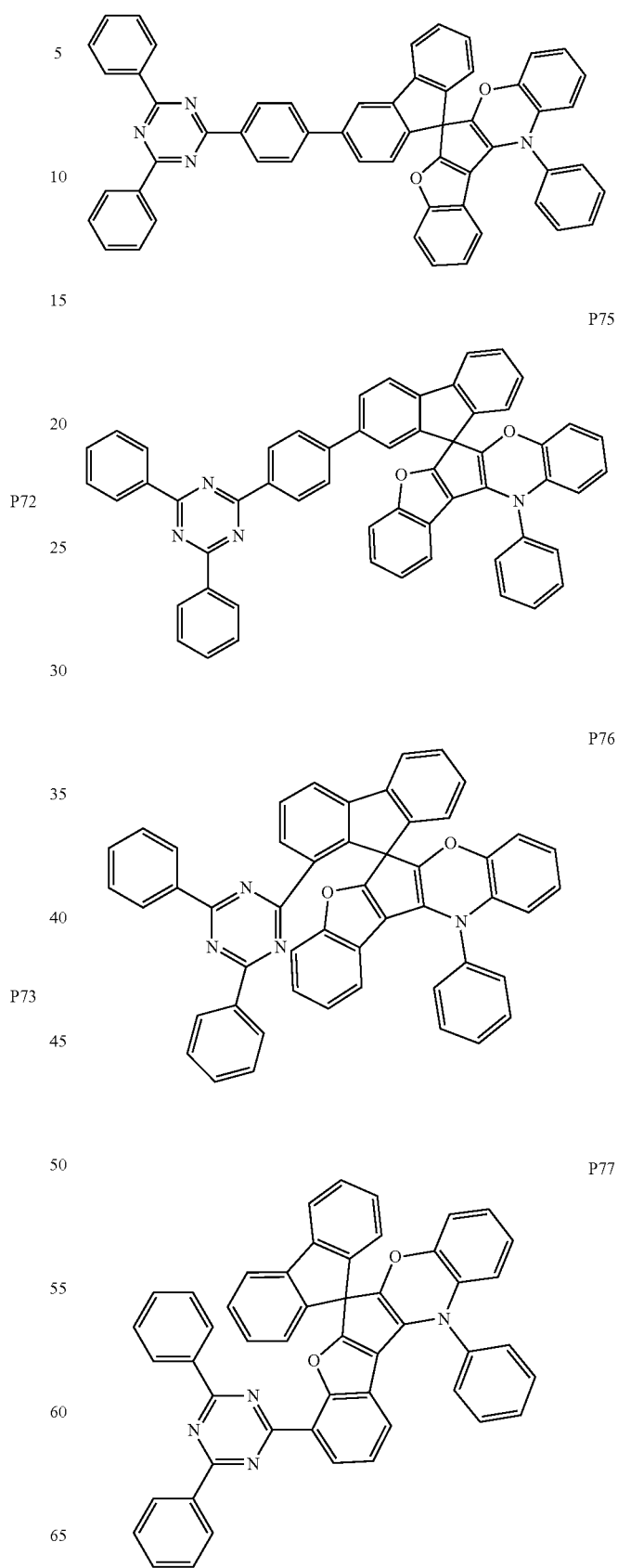

P78
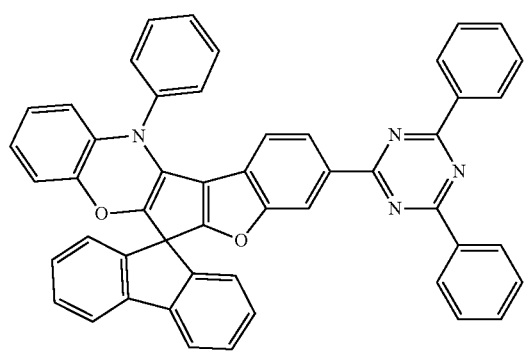
P79
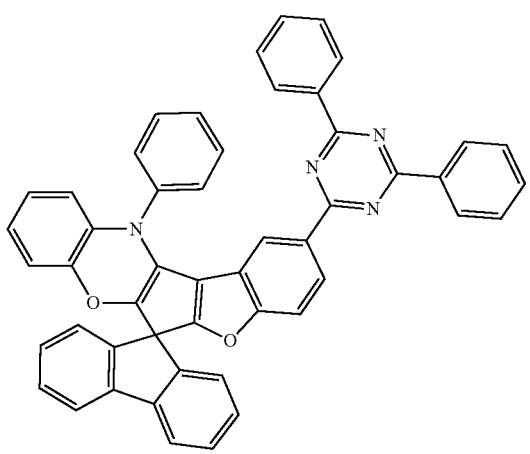
P80
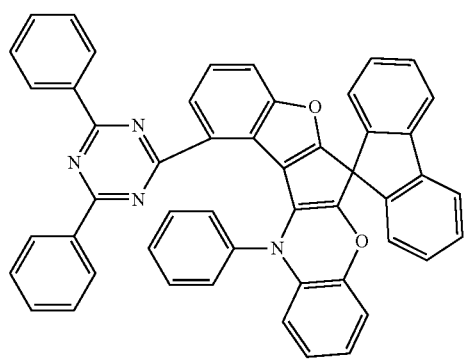
P81
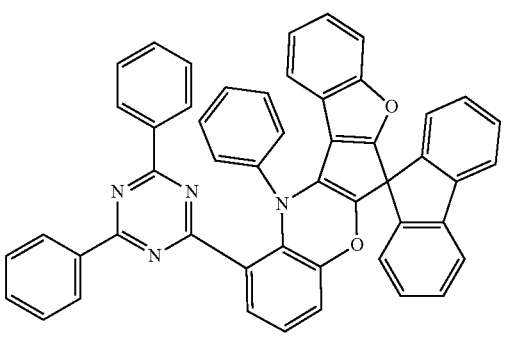
P82
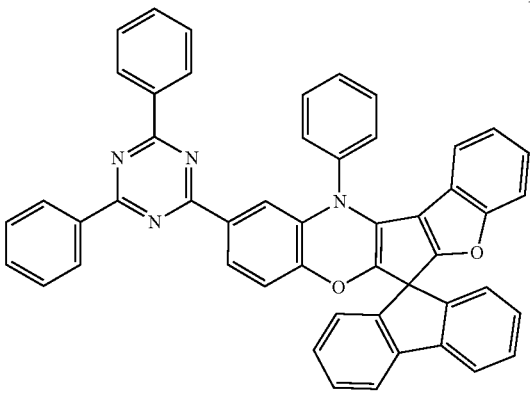
P83
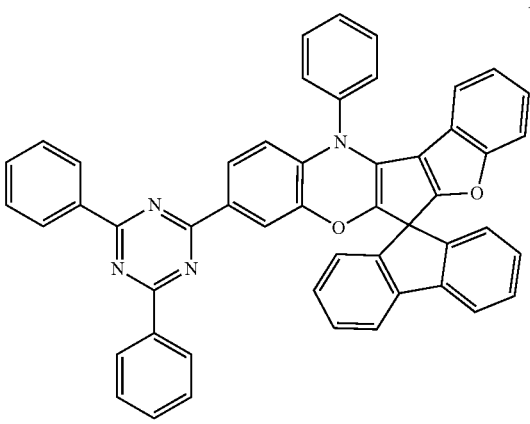
P84
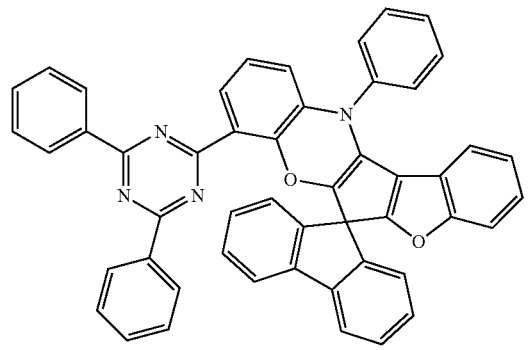

P85
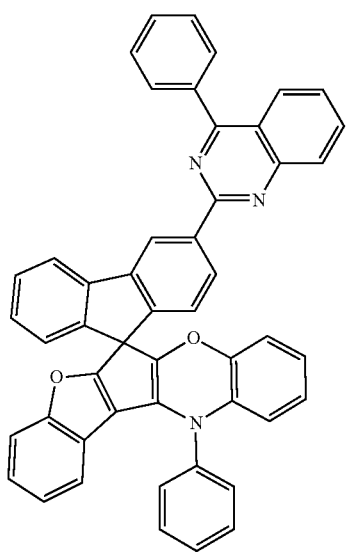
P86
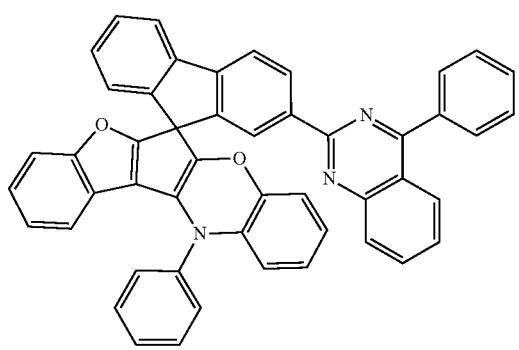
P87
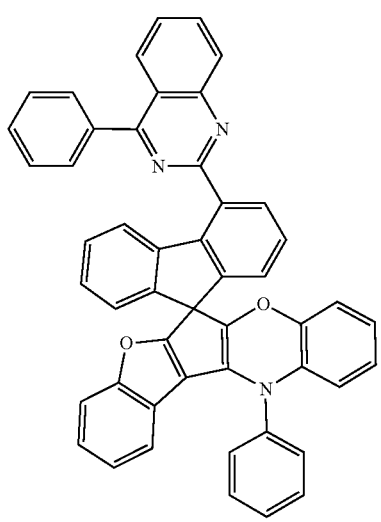
P88
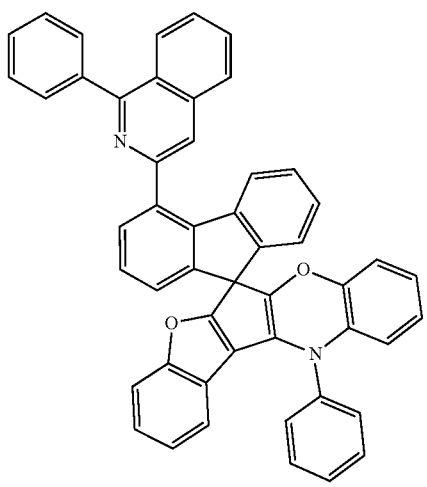
P89
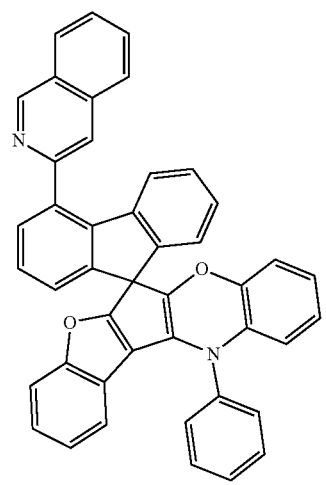
P90
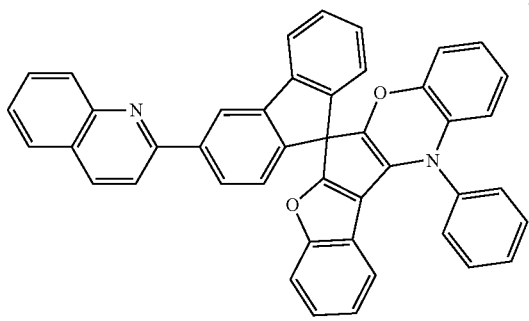
P91
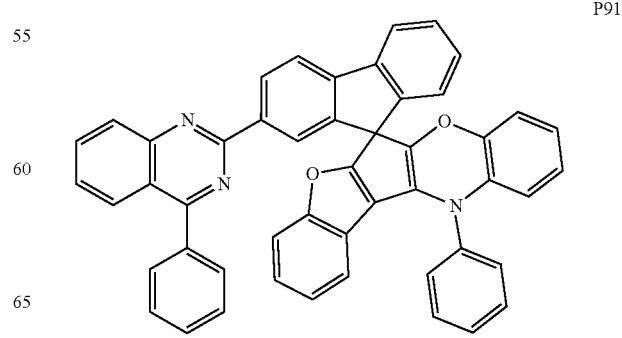

P92
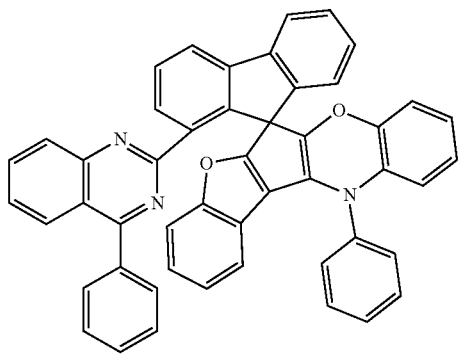
P93
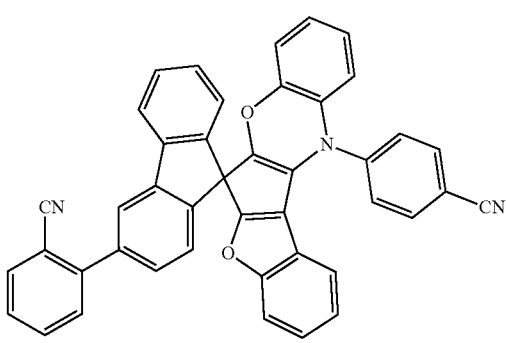
P94
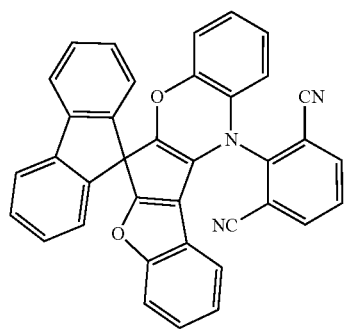
P95
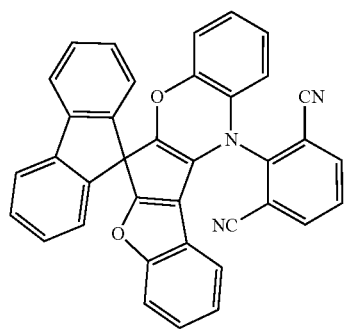
P96
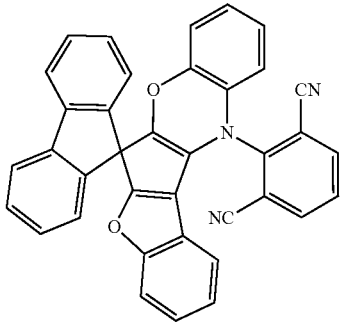
P97
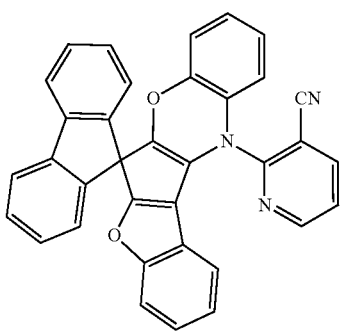
P98
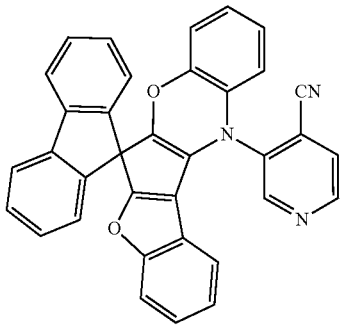
P99
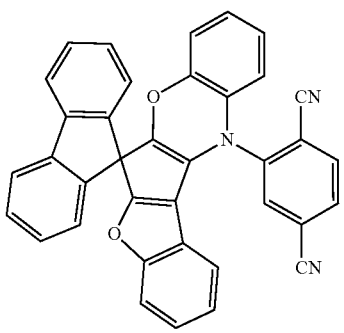

P100
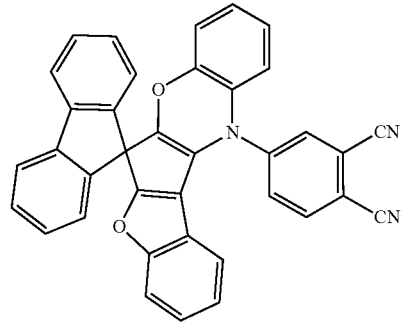
P101
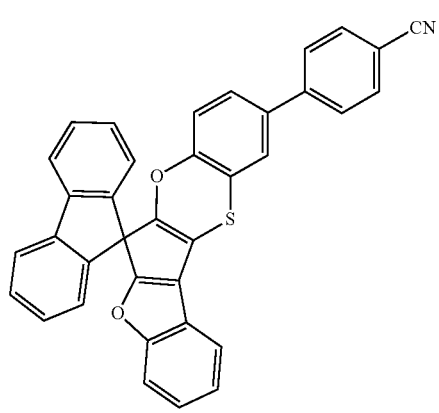
P102
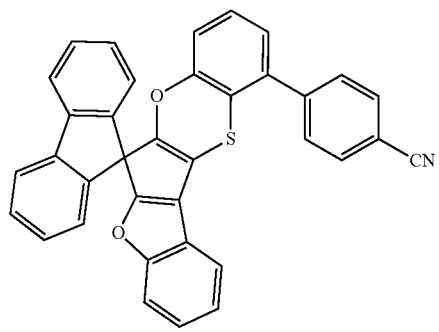
P103
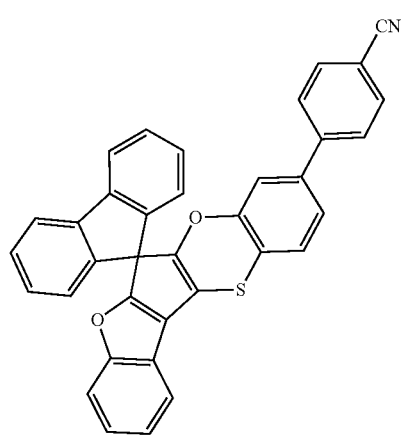
P104
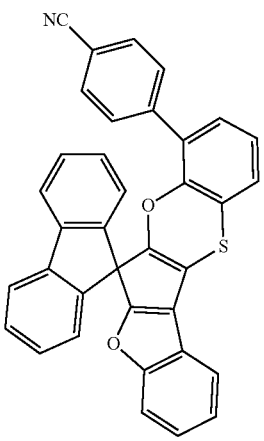
P105
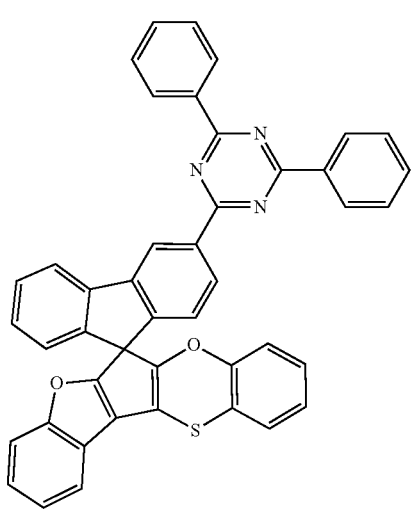
P106
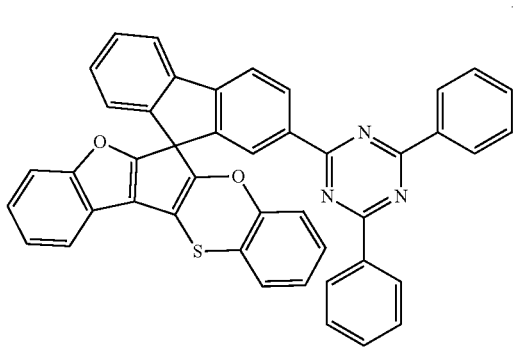

P107
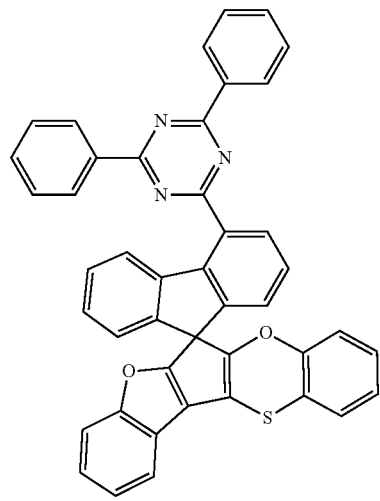
P108
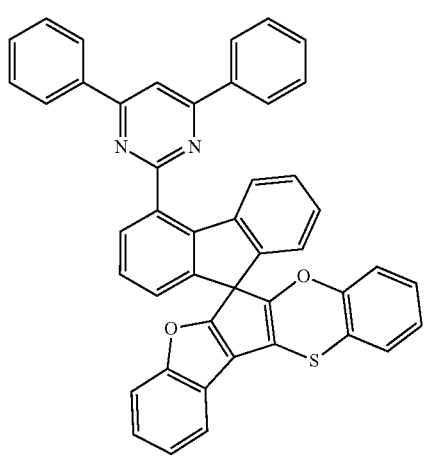
P109
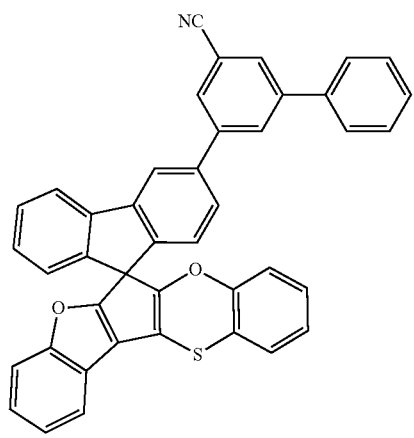
P110
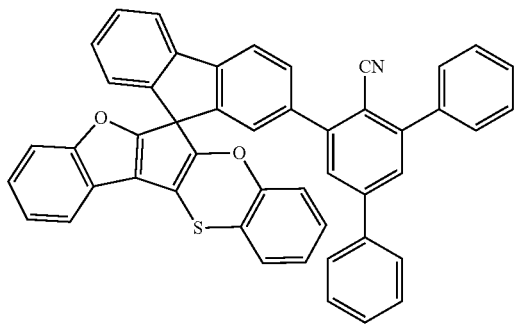
P111
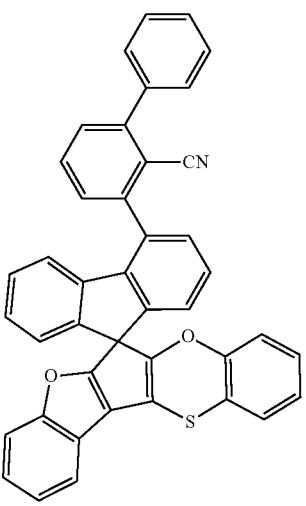
P112

P113
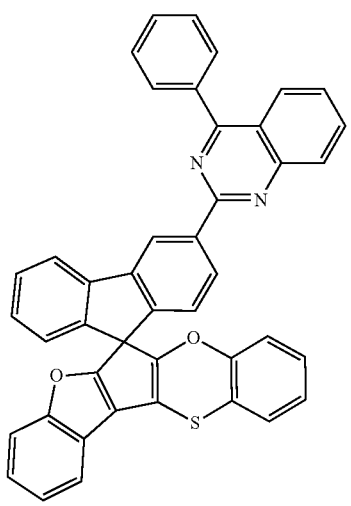
P114
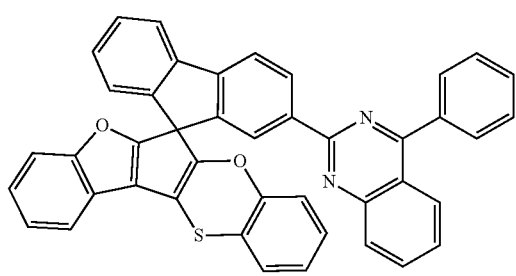
P115
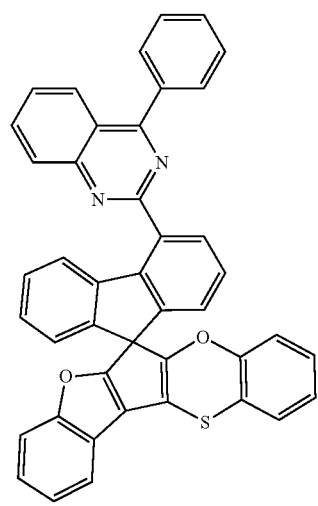
P116
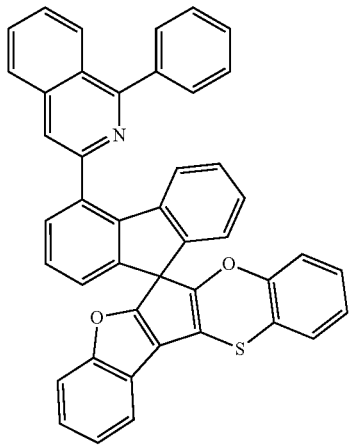
P117
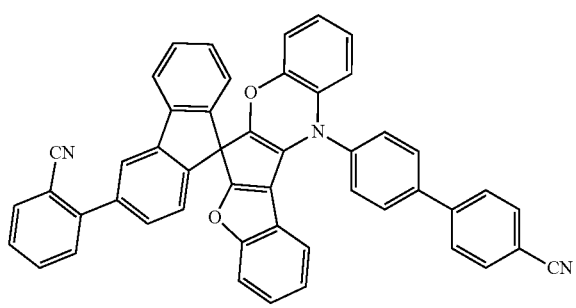
P118
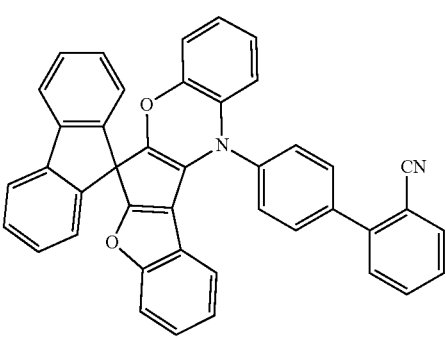
P119
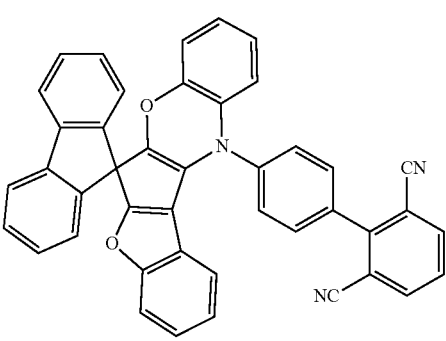

-continued
P120
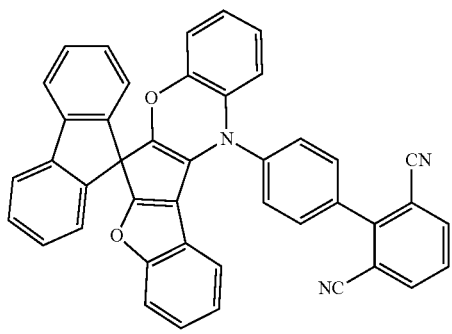
P121
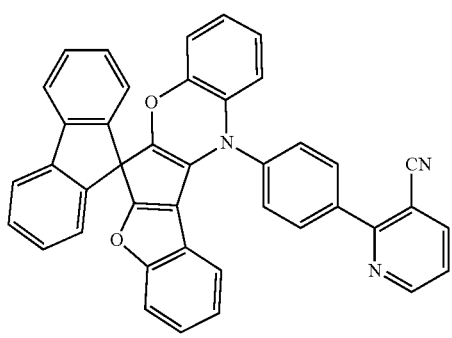
P122
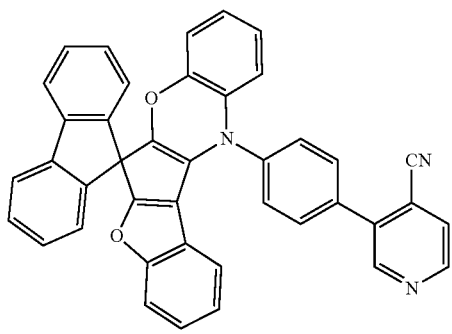
P123
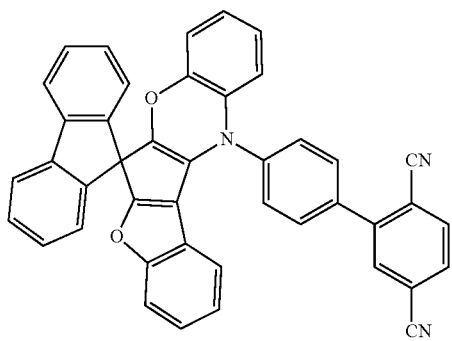
-continued
P124
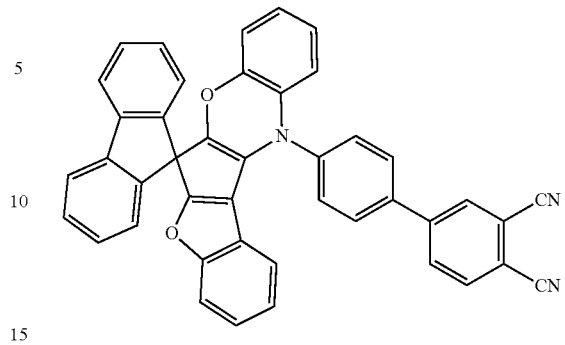
P125
P126
P127
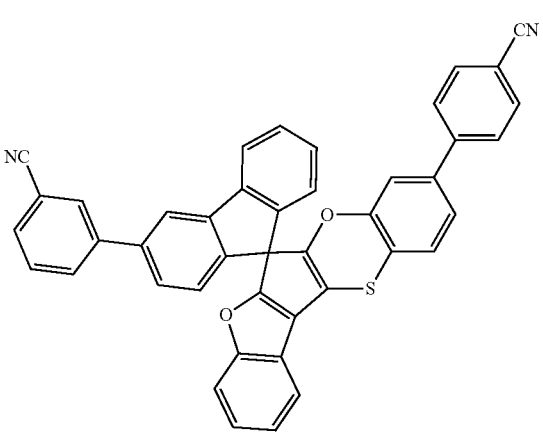

P128
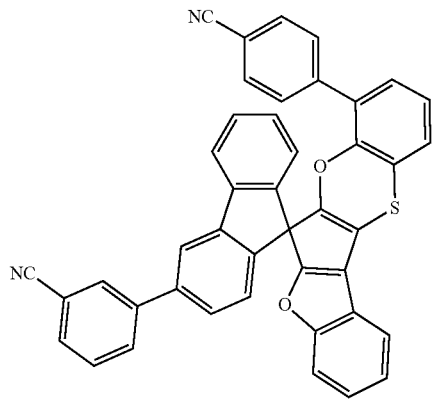
P129
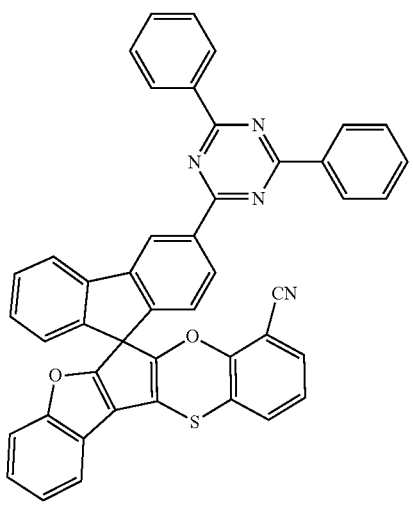
P130
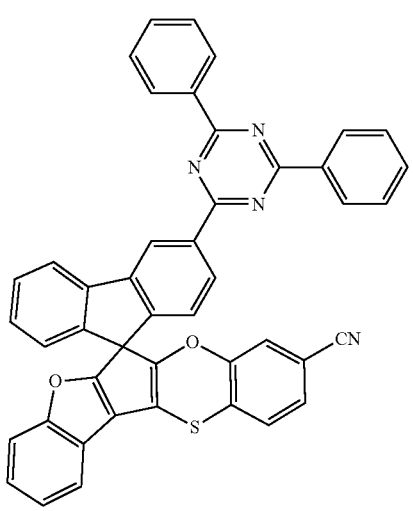
P131
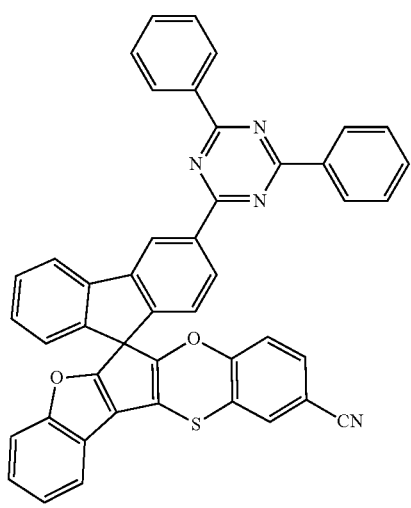
P132
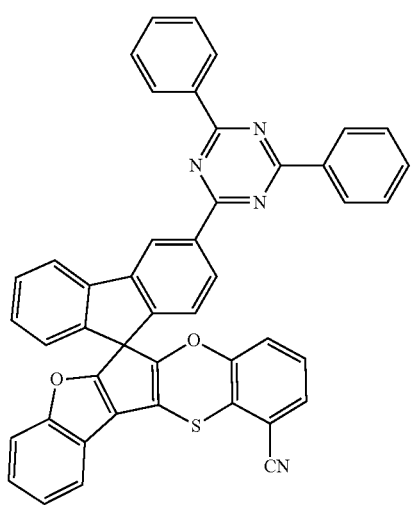
P133
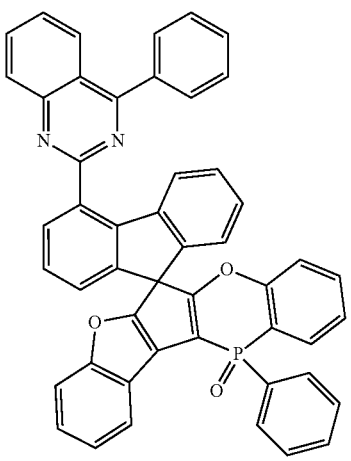

P134

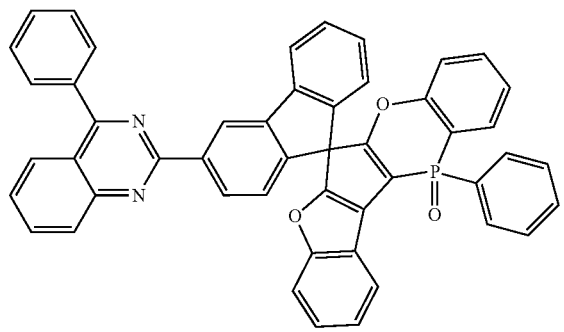

P135

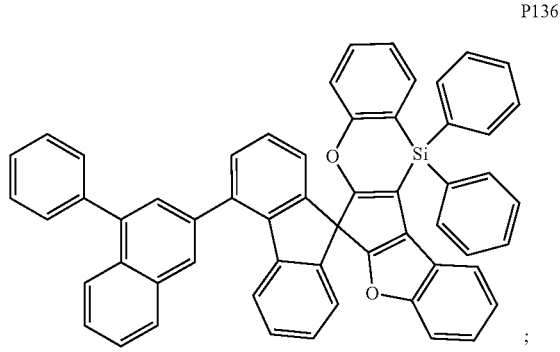

P136

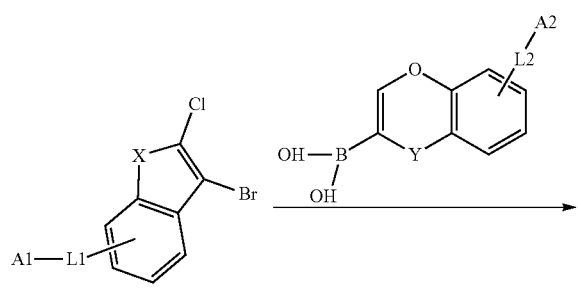

;

wherein, D represents deuterium.

In the present disclosure, the preparation route of the organic compound is described below.

General Synthesis Formula

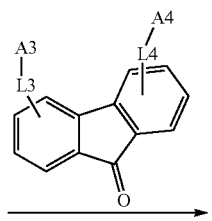

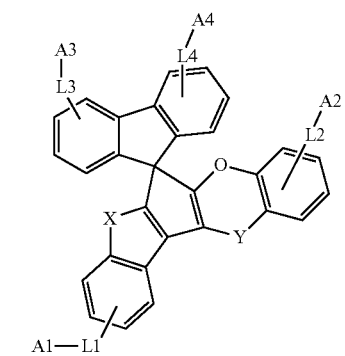

In the preparation route, L1 to L4 are defined within the same range as L in Formula I, and A1 to A4 are defined within the same range as A in Formula I. In the preparation route, different symbols are used to represent that L and A in Formula I may be from L1 to L4 and A1 to A4 in different raw materials. In the preparation route, the number of -La-Ab (wherein a is an integer from 1 to 4, and b is an integer from 1 to 4) groups in each raw material may be an integer from 0 to 4, that is, the raw materials may be unsubstituted or substituted with multiple -La-Ab groups, but the total number of -La-Ab groups in each raw material must be at least 1.

A second aspect of the present disclosure is to provide an organic electroluminescent material including the organic compound as described in the first aspect.

A third aspect of the present disclosure is to provide a light-emitting layer material including the organic compound as described in the first aspect.

A fourth aspect of the present disclosure is to provide an OLED device including an anode, a cathode and an organic thin film layer disposed between the anode and the cathode, where a material of the organic thin film layer includes the organic compound as described in the first aspect.

In one embodiment, the organic thin film layer includes a light-emitting layer which includes a host material and a doped material, wherein the host material includes the organic compound as described in the first aspect.

In the OLED device provided by the present disclosure, a material of the anode may be a metal, a metal oxide or a conductive polymer, wherein the metal includes copper, gold, silver, iron, chromium, nickel, manganese, palladium, platinum, etc. as well as alloys thereof, the metal oxide includes indium tin oxide (ITO), indium zinc oxide (IZO), zinc oxide, indium gallium zinc oxide (IGZO), etc., and the conductive polymer includes polyaniline, polypyrrole, poly(3-methylthiophene), etc. In addition to the above materials that facilitate hole injection and combinations thereof, the material of the anode further includes known materials suitable for use as the anode.

In the OLED device, a material of the cathode may be a metal or a multilayer metal material, wherein the metal includes aluminum, magnesium, silver, indium, tin, titanium, etc. as well as alloys thereof, and the multilayer metal material includes LiF/Al, LiO$_2$/Al, BaF$_2$/Al, etc. In addition to the above materials that facilitate electron injection and combinations thereof, the material of the cathode further includes known materials suitable for use as the cathode.

In the OLED device, the organic thin film layer includes at least one light-emitting layer (EML) and any one or a combination of at least two of a hole injection layer (HIL), a hole transport layer (HTL), an electron blocking layer (EBL), a hole blocking layer (HBL), an electron transport layer (ETL) or an electron injection layer (EIL) that are arranged on two sides of the at least one light-emitting layer. In addition to the organic compound as described in the first aspect of the present disclosure, the hole/electron injection and transport layers may also include carbazole compounds, arylamine compounds, benzimidazole compounds and metal compounds, etc. The OLED device may further be optionally provided with a capping layer (CPL) disposed on the cathode (on a side of the cathode facing away from the anode).

The OLED device of the present disclosure may be prepared by the following method: forming the anode on a transparent or opaque smooth substrate, forming the organic thin film layer on the anode, and forming the cathode on the organic thin film layer. The organic thin film layer may be formed by using known film forming methods such as evaporation, sputtering, spin coating, impregnation and ion plating.

A fifth aspect of the present disclosure is to provide a display panel including the OLED device as described in the fourth aspect.

A sixth aspect of the present disclosure is to provide an organic light-emitting display device including the display panel as described in the fifth aspect.

Several preparation examples of the organic compound of the present disclosure are exemplarily described below.

PREPARATION EXAMPLES

Example 1

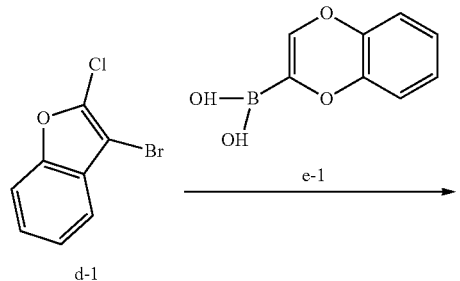

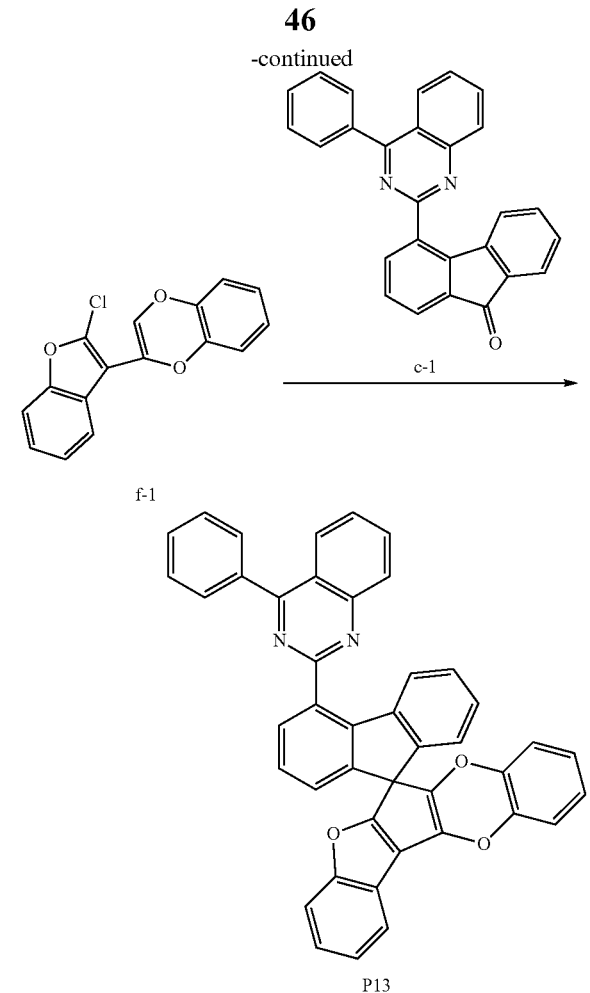

(1) Synthesis of Intermediate f-1

Compound d-1 (80 mmol), Compound e-1 (85 mmol), potassium carbonate (0.3 mol), tetrahydrofuran (250 mL), water (120 mL) and tetrakis(triphenylphosphine)palladium (0.6 g) were added in sequence to a three-necked flask, heated to reflux for 12 h under nitrogen protection, cooled, extracted with dichloromethane, concentrated, and purified the crude product through column chromatography to obtain Intermediate f-1.

MALDI-TOF (m/z): $C_{16}H_9ClO_3$, whose calculated value was 284.02 and measured value was 284.00.

(2) Synthesis of Compound P13

Intermediate f-1 (50 mmol) and dry tetrahydrofuran (120 mL) were added in sequence to a three-necked flask, cooled to −70° C. under nitrogen protection, and slowly added with 3.0 M n-butyl lithium (20 mL). After the dropwise addition, the system was reacted for 1 h and then added with a solution (70 mL) of Compound c-1 (55 mmol) in tetrahydrofuran. After the addition, the system was slowly warmed to room temperature, reacted for 3 h, extracted with dichloromethane, concentrated, added with acetic acid (120 mL) and concentrated hydrochloric acid (3 mL), heated to reflux for 8 h and then cooled. The solvents were removed. The crude product was dissolved in dichloromethane and washed with water. The organic layer was dried and concentrated, and then purified through column chromatography to obtain Compound P13.

MALDI-TOF (m/z): $C_{43}H_{24}N_2O_3$, whose calculated value was 616.18 and measured value was 616.15.

Results of the elemental analysis of the compound: calculated value: C 83.75, H 3.92, N 4.54, O 7.78; measured value: C 83.74, H 3.93, N 4.54, O 7.78.

Example 2

Example 3

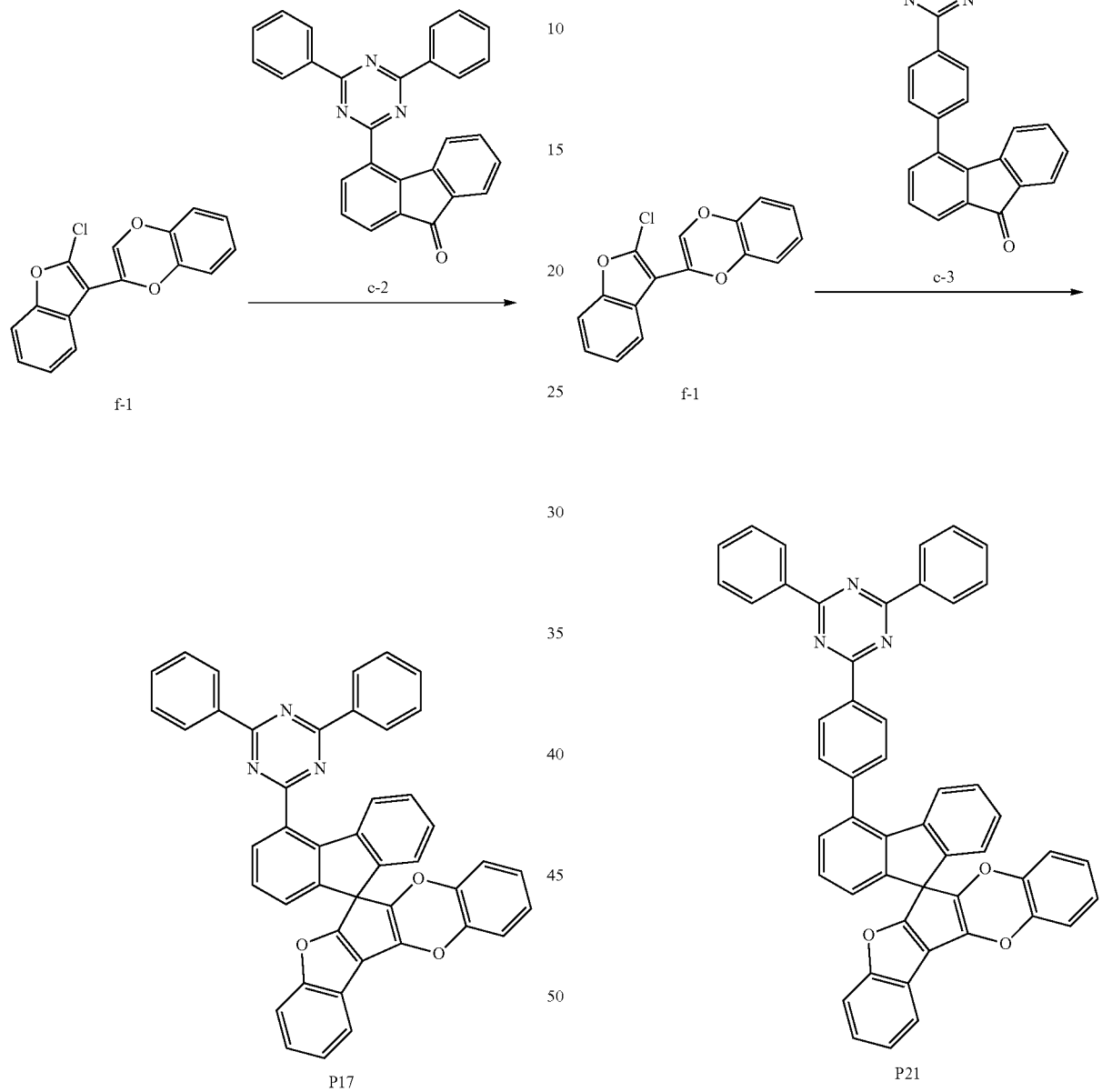

The preparation method of Compound P17 differs from step (2) in Example 1 in that Intermediate c-1 was replaced with an equimolar amount of c-2, while other raw materials, reaction steps and reaction conditions were the same as those in step (2) in Example 1, so as to obtain Compound P17.

MALDI-TOF (m/z): $C_{44}H_{25}N_3O_3$, whose calculated value was 643.19 and measured value was 643.15.

Results of the elemental analysis of the compound: calculated value: C 82.10, H 3.91, N 6.53, O 7.46; measured value: C 82.10, H 3.91, N 6.53, O 7.46.

The preparation method of Compound P21 differs from step (2) in Example 1 in that Intermediate c-1 was replaced with an equimolar amount of c-3, while other raw materials, reaction steps and reaction conditions were the same as those in step (2) in Example 1, so as to obtain Compound P21.

MALDI-TOF (m/z): $C_{50}H_{29}N_3O_3$, whose calculated value was 719.22 and measured value was 719.20.

Results of the elemental analysis of the compound: calculated value: C 83.43, H 4.06, N 5.84, O 6.67; measured value: C 83.42, H 4.07, N 5.84, O 6.67.

Example 4

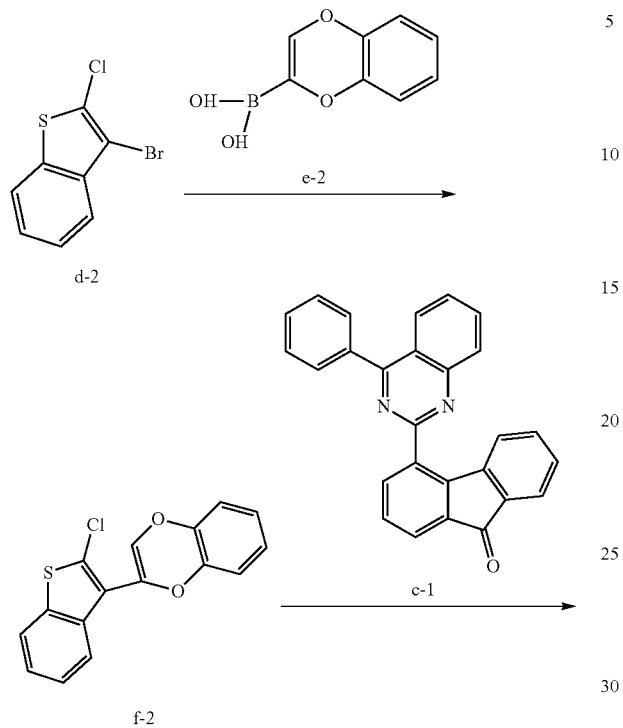

The preparation method of Intermediate f-2 differs from step (1) in Example 1 in that Intermediate d-1 was replaced with an equimolar amount of d-2 and Intermediate e-1 was replaced with an equimolar amount of e-2, while other raw materials, reaction steps and reaction conditions were the same as those in step (1) in Example 1, so as to obtain Compound f-2.

MALDI-TOF (m/z): $C_{16}H_9ClO_2S$, whose calculated value was 300.00 and measured value was 300.01.

The preparation method of Compound P33 differs from step (2) in Example 1 in that Intermediate f-1 was replaced with an equimolar amount of f-2, while other raw materials, reaction steps and reaction conditions were the same as those in step (2) in Example 1, so as to obtain Compound P33.

MALDI-TOF (m/z): $C_{43}H_{24}N_2O_2S$, whose calculated value was 632.16 and measured value was 632.12.

Results of the elemental analysis of the compound: calculated value: C 81.62, H 3.82, N 4.43, O 5.06, S 5.07; measured value: C, 81.61; H, 3.81; N, 4.44; O, 5.06; S, 5.07.

Example 5

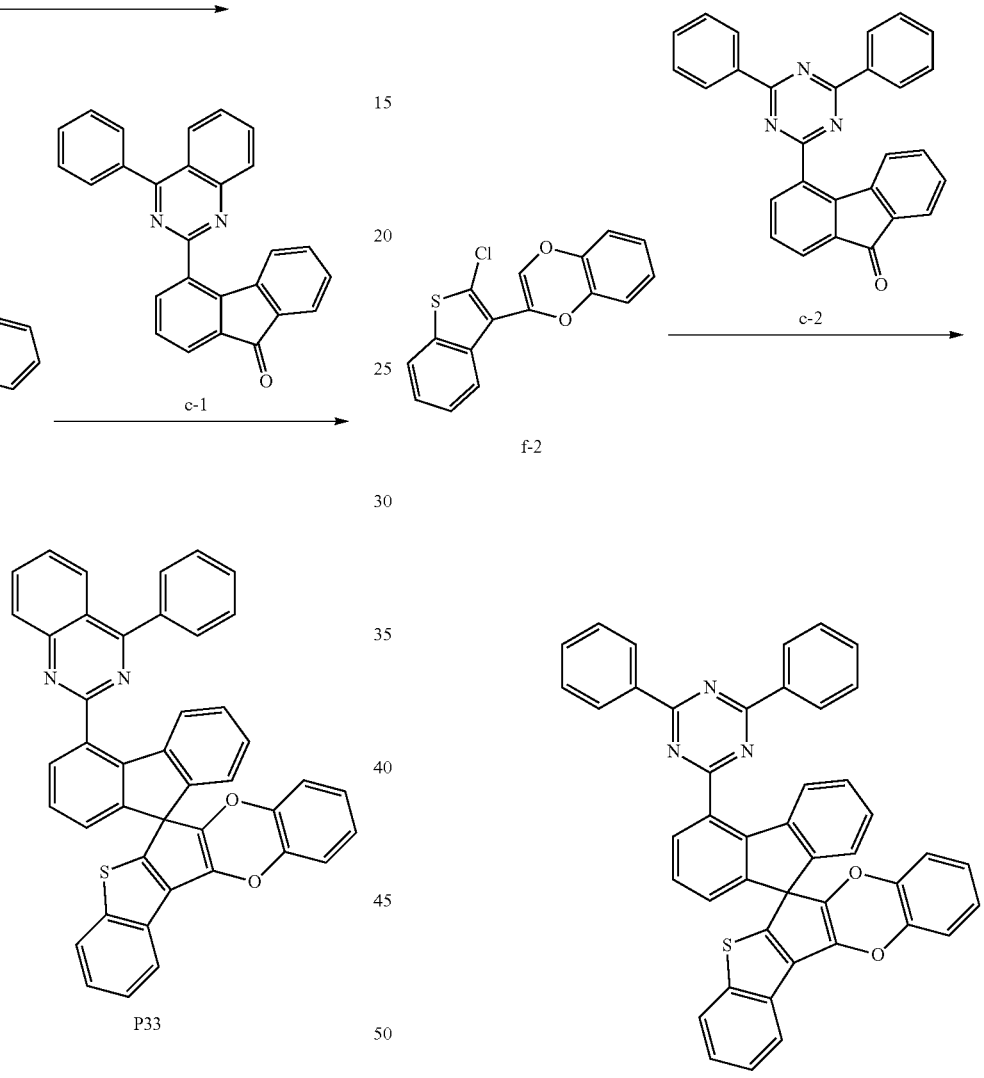

The preparation method of Compound P37 differs from step (2) in Example 1 in that Intermediate f-1 was replaced with an equimolar amount of f-2 and Intermediate c-1 was replaced with an equimolar amount of c-2, while other raw materials, reaction steps and reaction conditions were the same as those in step (2) in Example 1, so as to obtain Compound P37.

MALDI-TOF (m/z): $C_{44}H_{25}N_3O_2S$, whose calculated value was 659.17 and measured value was 659.14.

Results of the elemental analysis of the compound: calculated value: C 80.10, H 3.82, N 6.37, O 4.85, S 4.86; measured value: C 80.09, H 3.83, N 6.37, O 4.85, S 4.86.

Example 6

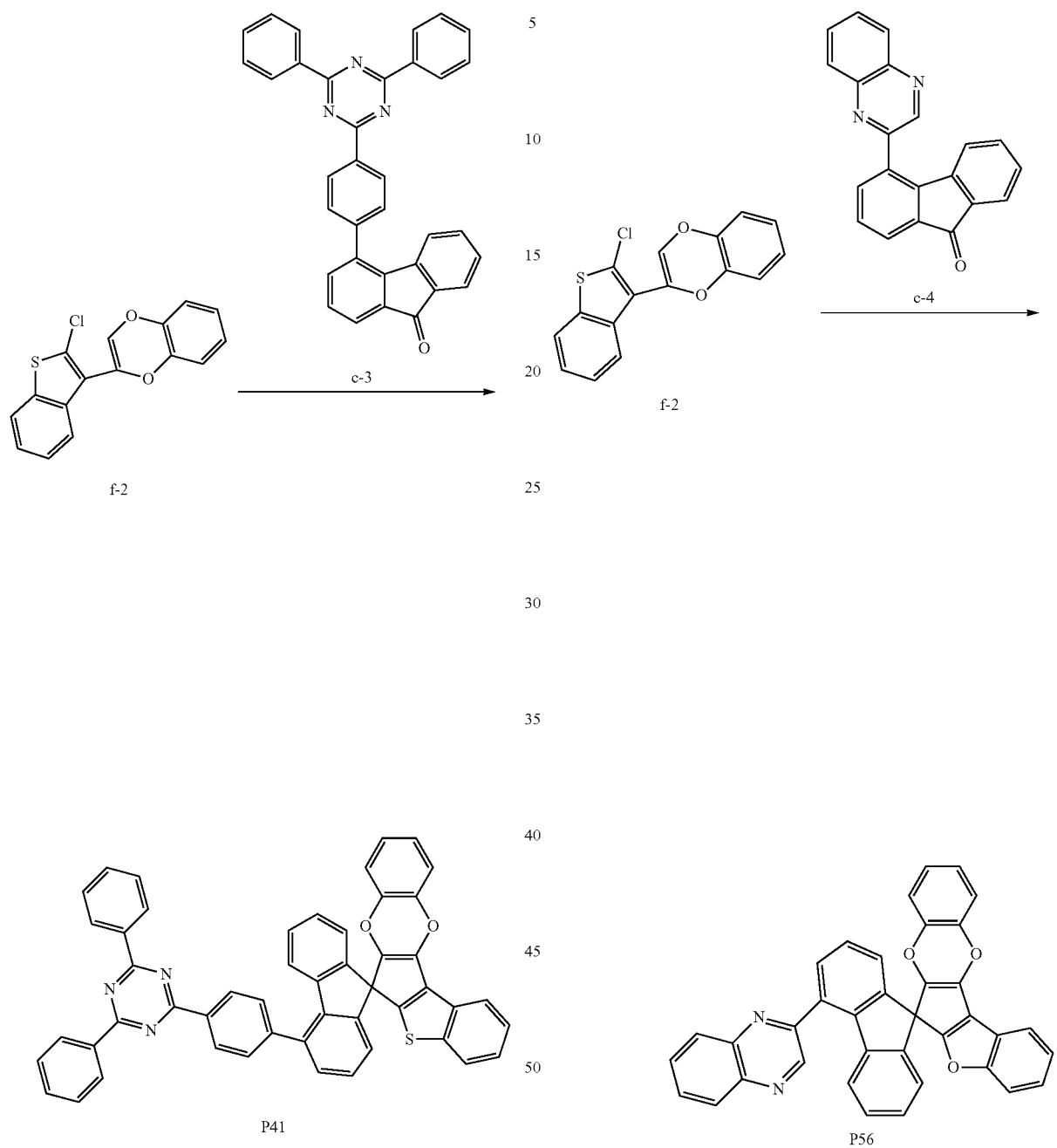

The preparation method of Compound P41 differs from step (2) in Example 1 in that Intermediate f-1 was replaced with an equimolar amount of f-2 and Intermediate c-1 was replaced with an equimolar amount of c-3, while other raw materials, reaction steps and reaction conditions were the same as those in step (2) in Example 1, so as to obtain Compound P41.

MALDI-TOF (m/z): $C_{50}H_{29}N_3O_2S$, whose calculated value was 735.20 and measured value was 735.18.

Results of the elemental analysis of the compound: calculated value: C 81.61, H 3.97, N 5.71, O 4.35, S 4.36; measured value: C 81.60, H 3.98, N 5.71, O 4.35, S 4.36.

Example 7

The preparation method of Compound P56 differs from step (2) in Example 1 in that Intermediate f-1 was replaced with an equimolar amount of f-2 and Intermediate c-1 was replaced with an equimolar amount of c-4, while other raw materials, reaction steps and reaction conditions were the same as those in step (2) in Example 1, so as to obtain Compound P56.

MALDI-TOF (m/z): $C_{37}H_{20}N_2O_3$, whose calculated value was 540.15 and measured value was 540.12.

Results of the elemental analysis of the compound: calculated value: C 82.21, H 3.73, N 5.18, O 8.88; measured value: C 82.20, H 3.74, N 5.18, O 8.88.

Example 8

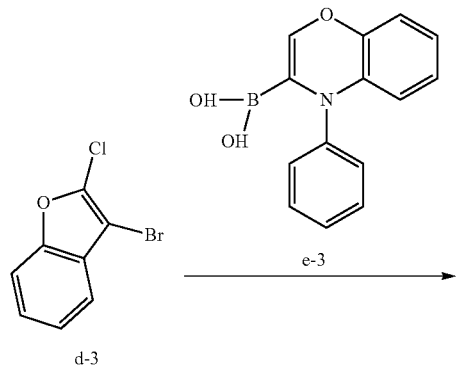

d-3

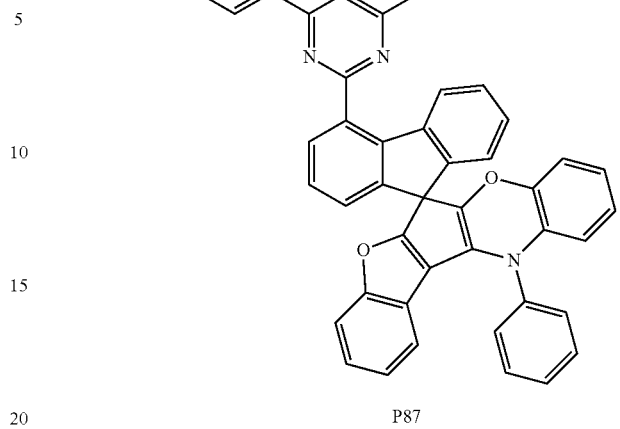

P87

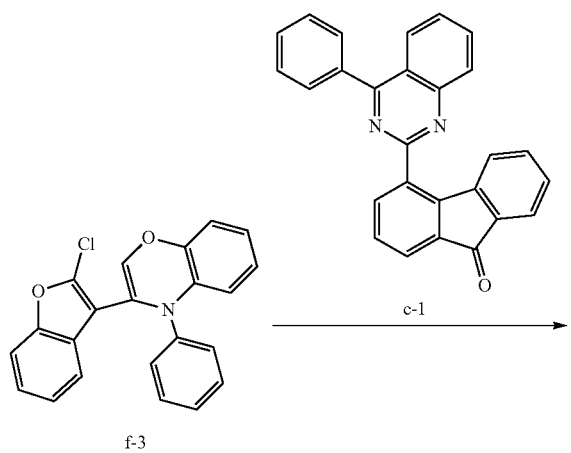

f-3

The preparation method of Intermediate f-3 differs from step (1) in Example 1 in that Intermediate d-1 was replaced with an equimolar amount of d-3 and Intermediate e-1 was replaced with an equimolar amount of e-3, while other raw materials, reaction steps and reaction conditions were the same as those in step (1) in Example 1, so as to obtain Compound f-3.

MALDI-TOF (m/z): $C_{22}H_{14}ClNO_2$, whose calculated value was 359.07 and measured value was 359.05.

The preparation method of Compound P87 differs from step (2) in Example 1 in that Intermediate f-1 was replaced with an equimolar amount of f-3, while other raw materials, reaction steps and reaction conditions were the same as those in step (2) in Example 1, so as to obtain Compound P87.

MALDI-TOF: (m/z): $C_{49}H_{29}N_3O_2$, whose calculated value was 691.23 and measured value was 632.10.

Results of the elemental analysis of the compound: calculated value: C 85.07, H 4.23, N 6.07, O 4.63; measured value: C 85.06, H 4.24, N 6.07, O 4.63.

Example 9 Synthesis of P47

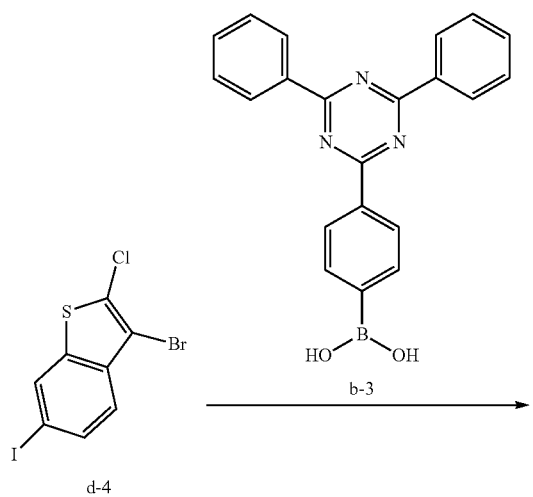

d-4

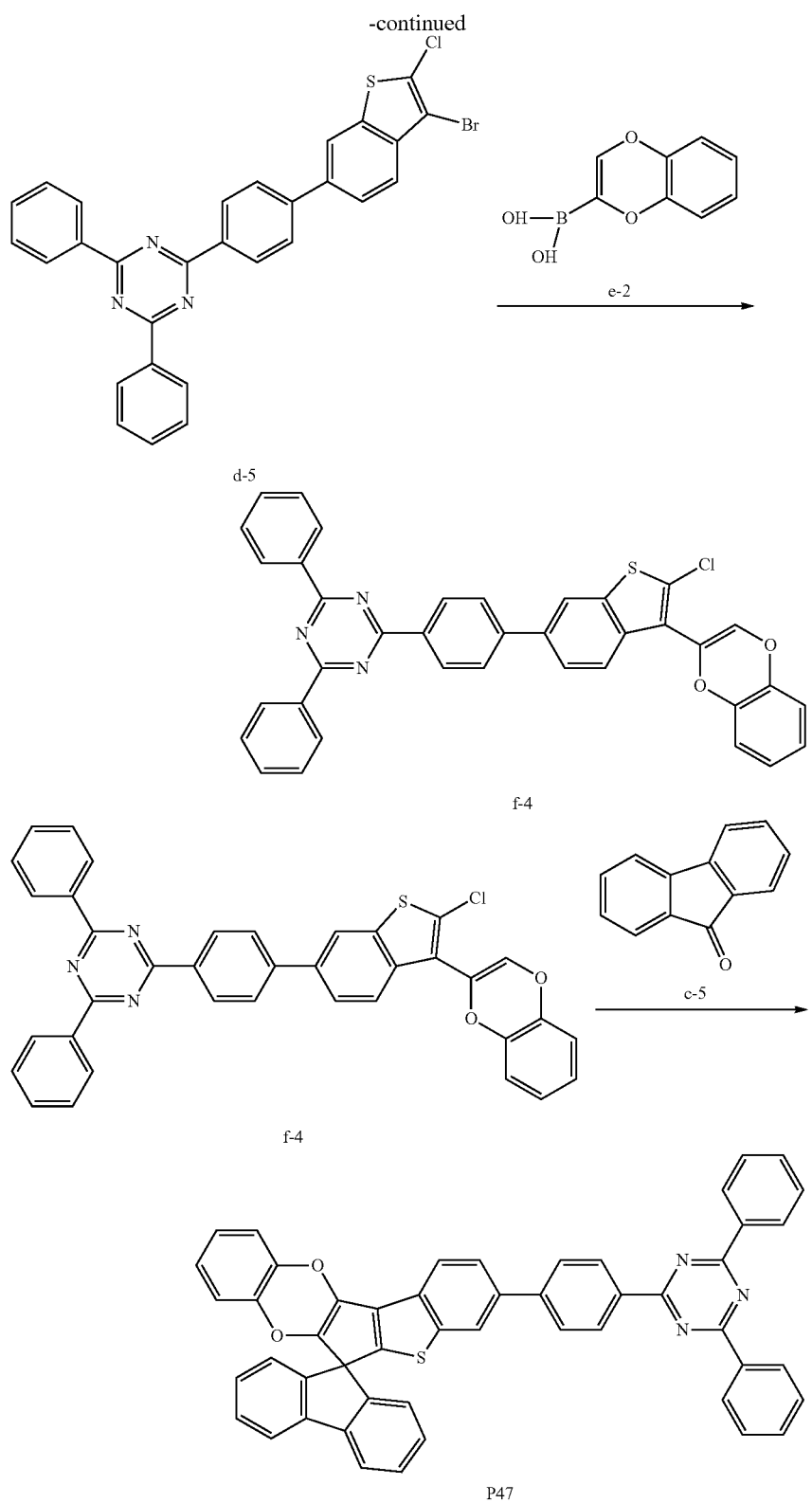

Synthesis of Intermediate d-5

Compound d-4 (60 mmol), Compound b-3 (65 mmol), potassium carbonate (0.3 mol), tetrahydrofuran (250 mL), water (120 mL) and tetrakis(triphenylphosphine)palladium (0.6 g) were added in sequence to a three-necked flask, heated to reflux for 12 h under nitrogen protection, cooled, extracted with dichloromethane, concentrated, and purified the crude product through column chromatography to obtain Intermediate d-5.

The preparation method of Intermediate f-4 differs from step (1) in Example 1 in that Intermediate d-1 was replaced with an equimolar amount of d-5 and Intermediate e-1 was replaced with an equimolar amount of e-2, while other raw materials, reaction steps and reaction conditions were the same as those in step (1) in Example 1, so as to obtain Compound f-4.

MALDI-TOF (m/z): $C_{37}H_{22}ClN_3O_2S$, whose calculated value was 607.11 and measured value was 607.10.

The preparation method of Compound P47 differs from step (2) in Example 1 in that Intermediate f-1 was replaced with an equimolar amount of f-4, while other raw materials, reaction steps and reaction conditions were the same as those in step (2) in Example 1, so as to obtain Compound P47 was obtained.

MALDI-TOF (m/z): $C_{50}H_{29}N_3O_2$, whose calculated value was 735.20 and measured value was 735.18.

Results of the elemental analysis of the compound: calculated value: C 81.61, H 3.97, N 5.71, O 4.35, S 4.36; measured value: C 81.60, H 3.96, N 5.72, O 4.35, S 4.36.

Comparative Example 1

Synthesis of Comparative Compound

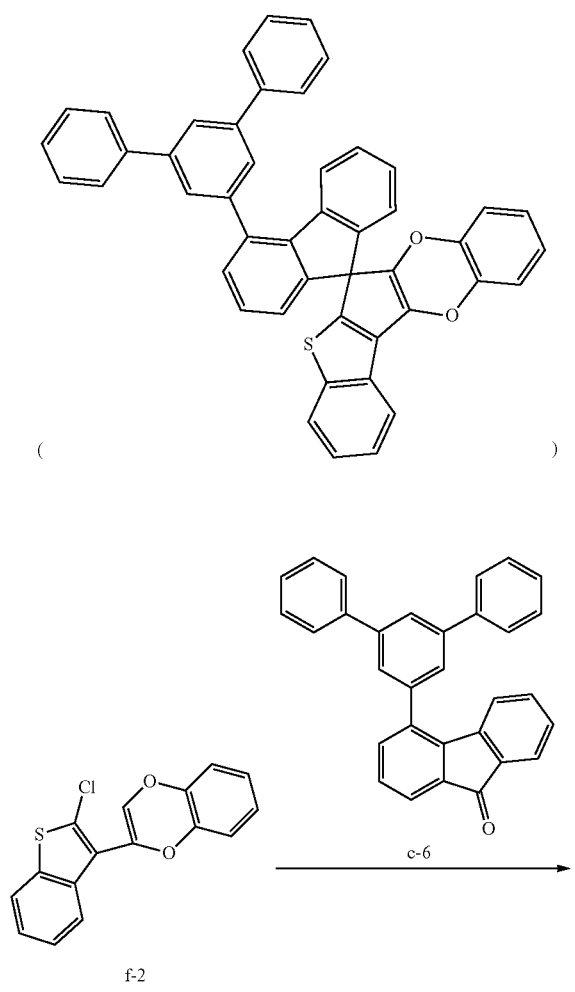

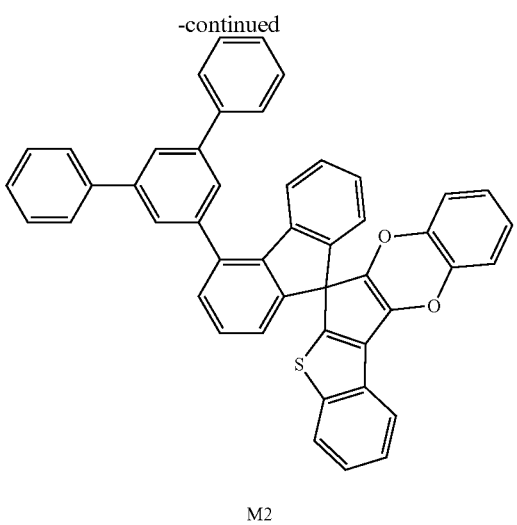

M2

The preparation method of Compound M2 differs from step (2) in Example 1 in that Intermediate f-1 was replaced with an equimolar amount of f-2 and Intermediate c-1 was replaced with an equimolar amount of c-6, while other raw materials, reaction steps and reaction conditions were the same as those in step (2) in Example 1, so as to obtain Compound M2.

MALDI-TOF (m/z): $C_{47}H_{28}O_2S$, whose calculated value was 656.18 and measured value was 656.15.

Results of the elemental analysis of the compound: calculated value: C 85.96, H 4.31, O 4.86, S 4.88; measured value: C 85.95, H 4.30, O 4.87, S 4.88.

Device Example 1

This example provides an organic light-emitting device. As shown in FIG. 1, the organic light-emitting device includes a substrate 1, an ITO anode 2, a first hole transport layer 3, a second hole transport layer 4, an electron blocking layer 5, a light-emitting layer 6, a first electron transport layer 7, a second electron transport layer 8, a cathode 9 (magnesium-silver electrode, where a mass ratio of magnesium to silver is 9:1) and a capping layer (CPL) 10, wherein the ITO anode 2 has a thickness of 15 nm, the first hole transport layer 3 has a thickness of 10 nm, the second hole transport layer 4 has a thickness of 95 nm, the electron blocking layer 5 has a thickness of 30 nm, the light-emitting layer 6 has a thickness of 30 nm, the first electron transport layer 7 has a thickness of 30 nm, the second electron transport layer 8 has a thickness of 5 nm, the magnesium-silver electrode 9 has a thickness of 15 nm, and the capping layer (CPL) 10 has a thickness of 100 nm.

The OLED device was prepared by the steps below.

(1) A glass substrate 1 was cut into a size of 50 mm×50 mm×0.7 mm, sonicated in isopropyl alcohol and deionized water for 30 minutes separately, and then exposed to ozone for about 10 minutes for cleaning. The obtained glass substrate having the ITO anode 2 was installed onto a vacuum deposition apparatus.

(2) A hole buffer layer materials HT-1:HAT-CN was evaporated by means of vacuum evaporation on the ITO anode 2 to obtain a layer with a thickness of 10 nm, where the mass ratio of compound HT-1 to compound HAT-CN was 98:2, and the layer was used as a first hole transport layer 3.

(3) A second hole transport layer 4 material HT-1 was vacuum evaporated on the first hole transport layer 3 to obtain a layer with a thickness of 95 nm, and the layer was used as a second hole transport layer 4.

(4) A material Prime-1 was evaporated on the second hole transport layer 4 to obtain a layer with a thickness of 30 nm, and the layer was used as an electron blocking layer 5.

(5) A light-emitting layer 6 was co-deposited on the electron blocking layer 5, wherein the Organic Compound P13 provided by Example 1 of the present disclosure was used as a host material, Ir(piq)2(acac) was used as a doped material, the mass ratio of the Organic Compound P13 to Ir(piq)2(acac) was 19:1, and the thickness of the light-emitting layer was 30 nm.

(6) A Compound ET-1 of a first electron transport layer 7 was vacuum evaporated on the light-emitting layer 6 to obtain the first electron transport layer 7 with a thickness of 30 nm.

(7) A material LiF of a second electron transport layer 8 was vacuum evaporated on the first electron transport layer 7 to obtain the second electron transport layer 8 with a thickness of 5 nm.

(8) Magnesium and silver were vacuum evaporated on the second electron transport layer 8 to obtain the cathode 9 with a thickness of 15 nm, wherein a mass ratio of magnesium and silver was 9:1.

(9) A hole-type material CPL-1 with a high refractive index was vacuum evaporated on the cathode 9 for use as the cathode coating layer (capping layer or CPL) 10 with a thickness of 100 nm.

The materials HAT-CN, HT-1, Prime-1, Ir(piq)2(acac), ET-1 and CPL-1 mentioned in the above steps have the following structural formulas:

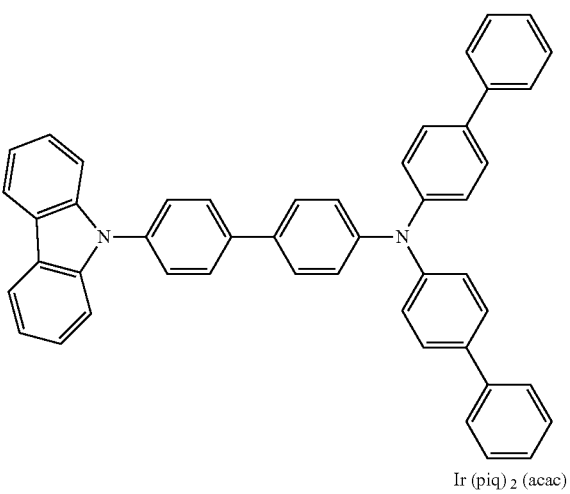

Prime-1

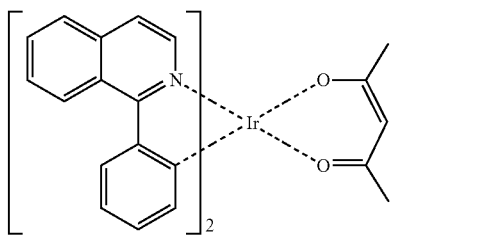

Ir (piq)$_2$ (acac)

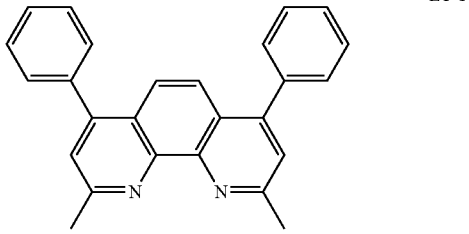

ET-1

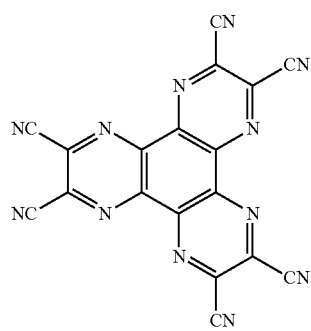

HAT-CN

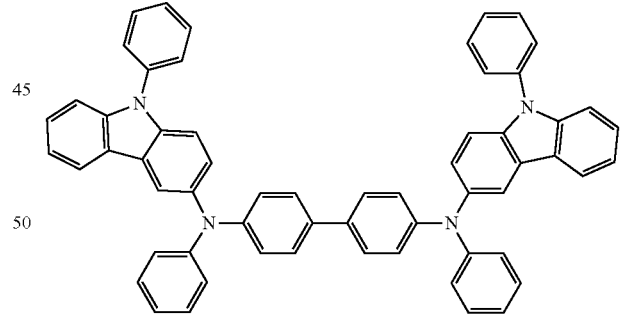

CPL-1

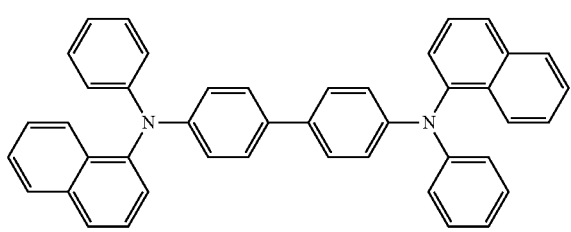

HT-1

Device Example 2

This device example differs from Device Example 1 only in that Organic Compound P13 in step (5) was replaced with an equivalent amount of Organic Compound P17 provided by the present disclosure. The other preparation steps were the same.

Device Example 3

This device example differs from Device Example 1 only in that Organic Compound P13 in step (5) was replaced with an equivalent amount of Organic Compound P21 provided by the present disclosure. The other preparation steps were the same.

Device Example 4

This device example differs from Device Example 1 only in that Organic Compound P13 in step (5) was replaced with an equivalent amount of Organic Compound P33 provided by the present disclosure. The other preparation steps were the same.

Device Example 5

This device example differs from Device Example 1 only in that Organic Compound P13 in step (5) was replaced with an equivalent amount of Organic Compound P37 provided by the present disclosure. The other preparation steps were the same.

Device Example 6

This device example differs from Device Example 1 only in that Organic Compound P13 in step (5) was replaced with an equivalent amount of Organic Compound P41 provided by the present disclosure. The other preparation steps were the same.

Device Example 7

This device example differs from Device Example 1 only in that Organic Compound P13 in step (5) was replaced with an equivalent amount of Organic Compound P56 provided by the present disclosure. The other preparation steps were the same.

Device Example 8

This device example differs from Device Example 1 only in that Organic Compound P13 in step (5) was replaced with an equivalent amount of Organic Compound P87 provided by the present disclosure. The other preparation steps were the same.

Device Example 9

This device example differs from Device Example 1 only in that Organic Compound P13 in step (5) was replaced with an equivalent amount of Organic Compound P47 provided by the present disclosure. The other preparation steps were the same.

Device Comparative Example 1

This device comparative example differs from Device Example 1 only in that Organic Compound P13 in step (5) was replaced with an equivalent amount of Comparative Compound

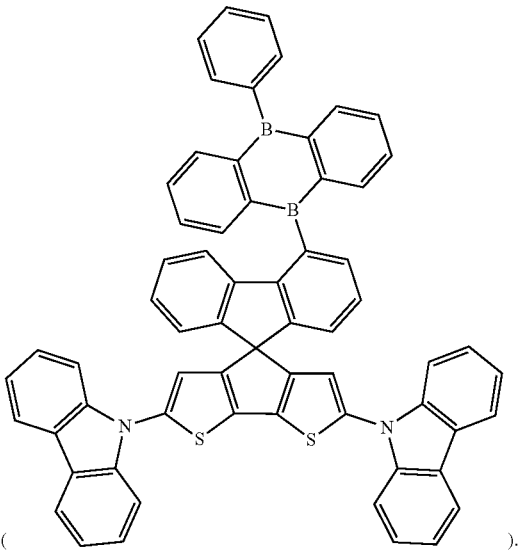

M1

The other preparation steps were the same.

Device Comparative Example 2

This device comparative example differs from Device Example 1 only in that Organic Compound P13 in step (5) was replaced with an equivalent amount of Comparative Compound

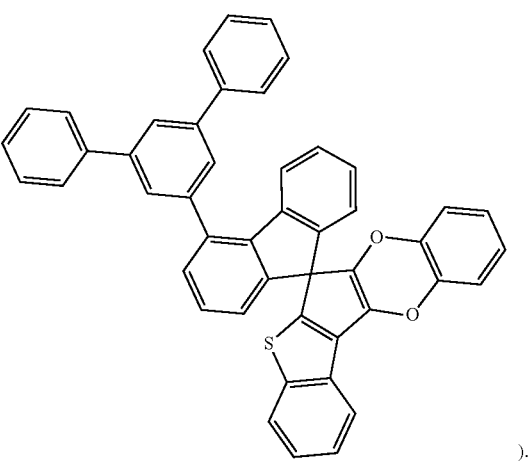

M2

The other preparation steps were the same.

Performance Evaluation of OLED Devices

A Keithley 2365A digital nanovoltmeter was used for testing currents of the OLED device at different voltages, and then the currents were divided by a luminescence area to obtain current densities of the OLED device at different voltages. A Konicaminolta CS-2000 spectroradiometer was used for testing the brightness and radiation energy flux densities of the OLED device at different voltages. According to the current densities and brightness of the OLED device at different voltages, a turn-on voltage and current efficiency (CE, Cd/A) at the same current density (10 mA/cm$^2$) were obtained, where Von denotes the turn-on voltage when the brightness is 1 cd/m$^2$. A lifetime LT95 was obtained (under a testing condition of 50 mA/cm$^2$) by measuring the time taken for the OLED device to reach 95% of its initial brightness. Specific data is shown in Table 1.

TABLE 1

Results of performance detection of OLED devices

| OLED Device | Host Material of the Light-emitting layer | Von (V) | CE (Cd/A) | LT95 (h) |
| --- | --- | --- | --- | --- |
| Device Example 1 | P13 | 95.60% | 106.20% | 106.10% |
| Device Example 2 | P17 | 95.20% | 107.30% | 106.30% |
| Device Example 3 | P21 | 94.90% | 107.90% | 105.80% |
| Device Example 4 | P33 | 95.10% | 106.80% | 106.50% |
| Device Example 5 | P37 | 95.30% | 106.60% | 105.90% |
| Device Example 6 | P41 | 94.90% | 105.10% | 106.10% |
| Device Example 7 | P56 | 95.20% | 106.30% | 106.60% |
| Device Example 8 | P87 | 96.80% | 104.50% | 103.90% |
| Device Example 9 | P47 | 97.30% | 102.20% | 102.20% |
| Device Comparative Example 1 | Comparative Compound M1 | 98.60% | 101.00% | 101.90% |
| Device Comparative Example 2 | Comparative Compound M2 | 100.00% | 100.00% | 100.00% |

As can be seen from the data in Table 1, compared with the device in Comparative Example 1, the electroluminescent device using the organic compound of the present disclosure has a lower turn-on voltage which is reduced by about 3.2% to 5.1% (as shown in Table 1, the turn-on voltage is the relative turn-on voltage obtained by taking the turn-on voltage of Device Comparative Example 2 as 100%) so that the power consumption of the device can be effectively reduced; the device using the organic compound of the present disclosure has higher current efficiency which is about 2.2% to 7.9% higher than that of Comparative Example 2 (as shown in Table 1, the current efficiency is the relative current efficiency obtained by taking the current efficiency of Device Comparative Example 2 as 100%); and the device using the organic compound of the present disclosure has a longer lifetime which is about 2.2% to 6.6% longer than that of the device in Comparative Example 1 (as shown in Table 1, LT95 is the relative LT95 obtained by taking LT95 of Device Comparative Example 2 as 100%).

The applicant has stated that although the organic compound and the application thereof in the present disclosure are described through the preceding embodiments, the present disclosure is not limited to the preceding embodiments, which means that the implementation of the present disclosure does not necessarily depend on the preceding embodiments. It should be apparent to those skilled in the art that any improvements made to the present disclosure, equivalent replacements of raw materials selected in the present disclosure, additions of adjuvant ingredients, selections of specific methods, etc., all fall within the protection scope and the disclosure scope of the present disclosure.

What is claimed is:

1. An organic compound, wherein the organic compound has a structure represented by Formula I:

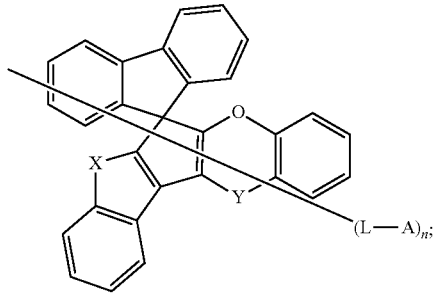

Formula I wherein L is independently selected from a single bond, substituted or unsubstituted C6 to C30 aryl or substituted or unsubstituted C5 to C30 heteroaryl;
A is independently selected from cyano, substituted or unsubstituted C6 to C40 arylamine or substituted or unsubstituted C5 to C30 heteroaryl;
X and Y are independently selected from O, S,

or M—R, wherein M is N, Si-R or B, and R is C1 to C10 linear or branched alkyl, C1 to C10 alkoxy, C6 to C20 aryl or C6 to C20 arylamino; and
n is an integer from 1 to 16.

2. The organic compound according to claim 1, wherein a substituent in the substituted C6 to C30 aryl, substituted C5 to C30 heteroaryl or substituted C6 to C40 arylamine is protium, deuterium, halogen, cyano, C1 to C10 linear or branched alkyl, C1 to C10 alkoxy, C6 to C20 aryl or C6 to C20 arylamino.

3. The organic compound according to claim 1, wherein L is independently selected from a single bond, substituted or unsubstituted phenyl, substituted or unsubstituted biphenyl, substituted or unsubstituted naphthyl, or substituted or unsubstituted anthryl;
wherein a substituent in the substituted group is selected from deuterium, tritium, cyano or phenyl.

4. The organic compound according to claim 1, wherein A is independently selected from cyano, substituted or unsubstituted diphenylamine, substituted or unsubstituted triphenylamine, substituted or unsubstituted carbazolyl, substituted or unsubstituted triazinyl, substituted or unsubstituted quinolyl, or substituted or unsubstituted isoquinolyl;
wherein a substituent in the substituted group is selected from protium, deuterium, halogen, cyano, C1 to C10 linear or branched alkyl, C1 to C10 alkoxy, C6 to C20 aryl, or C6 to C20 arylamino.

5. The organic compound according to claim 1, wherein X and Y are independently selected from O or S.

6. The organic compound according to claim 1, wherein R is phenyl, pyridyl, biphenyl, pyridyl-phenyl, phenyl substituted with at least one cyano group, pyridyl substituted with at least one cyano group, biphenyl substituted with at least one cyano group or pyridyl-phenyl substituted with at least one cyano group.

7. The organic compound according to claim 1, wherein the organic compound has a structure represented by Formula II:

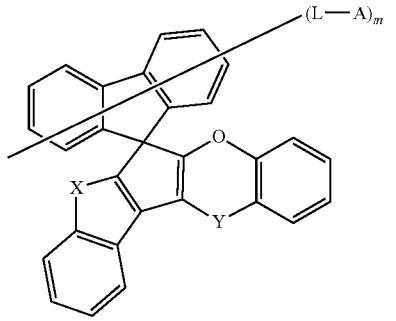

Formula II wherein L is independently selected from a single bond, substituted or unsubstituted C6 to C30 aryl or substituted or unsubstituted C5 to C30 heteroaryl;

A is independently selected from cyano, substituted or unsubstituted C6 to C40 arylamine or substituted or unsubstituted C5 to C30 heteroaryl;

X and Y are independently selected from O, S,

or M—R, wherein M is N, Si-R or B, and R is C1 to C10 linear or branched alkyl, C1 to C10 alkoxy, C6 to C20 aryl or C6 to C20 arylamino; and m is an integer from 1 to 8.

8. The organic compound according to claim 1, wherein the organic compound is any one of the following compounds:

P01

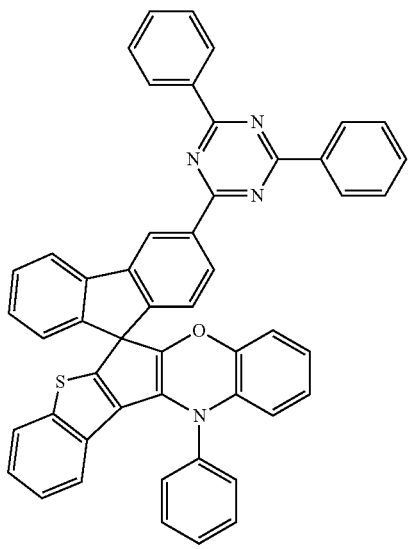

P02

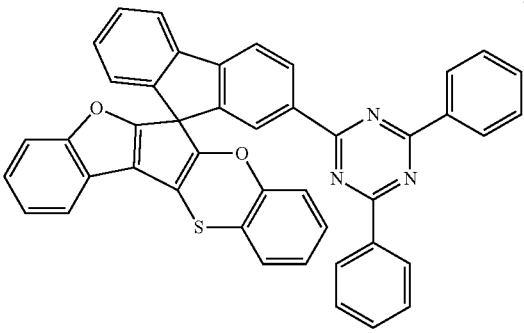

P03

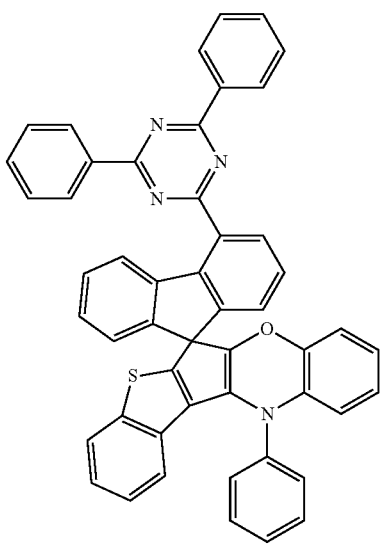

P04

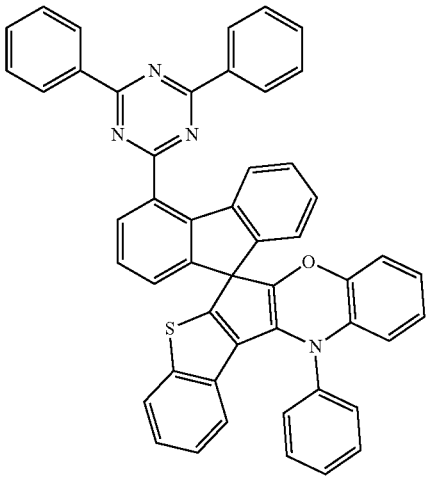

P05
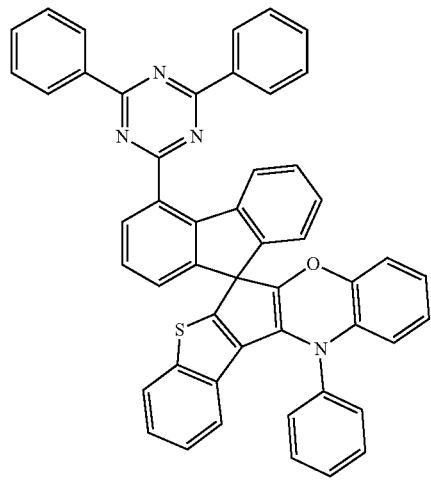
P06
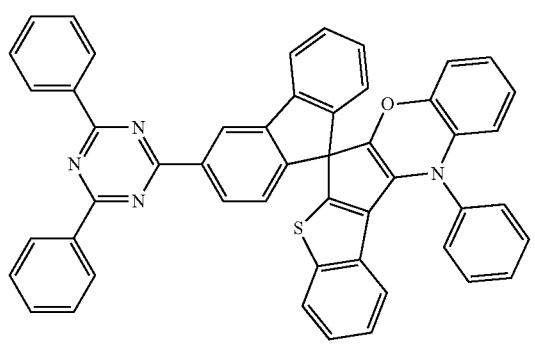
P07
P08
P09
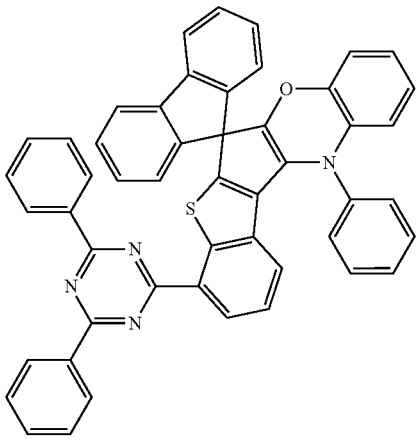
P10
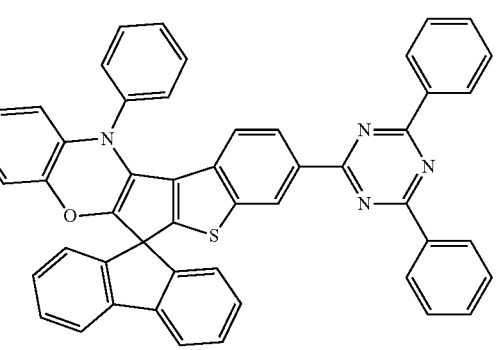
P11
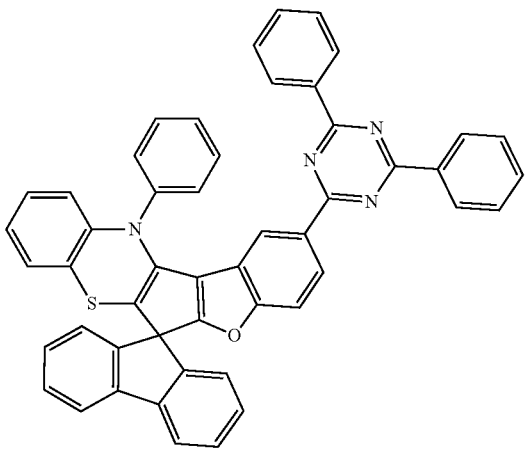
P12
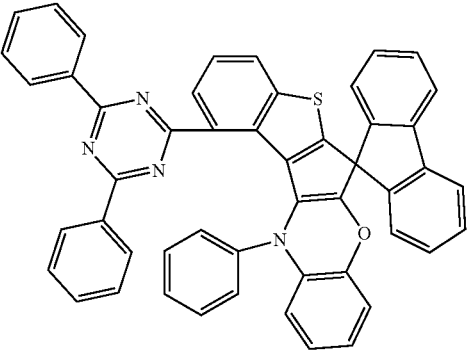

P13 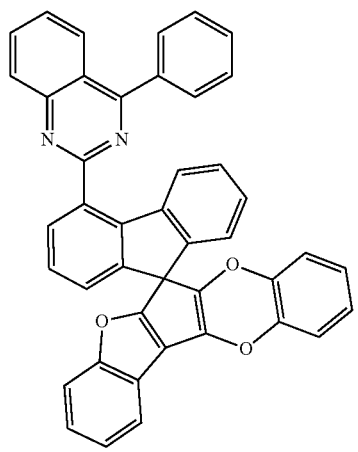
P17 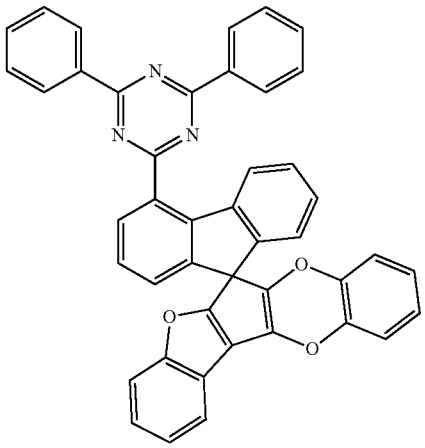
P14 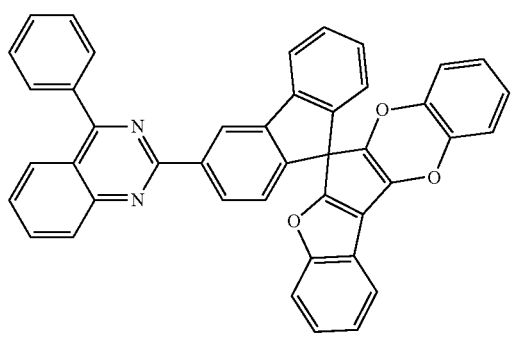
P18 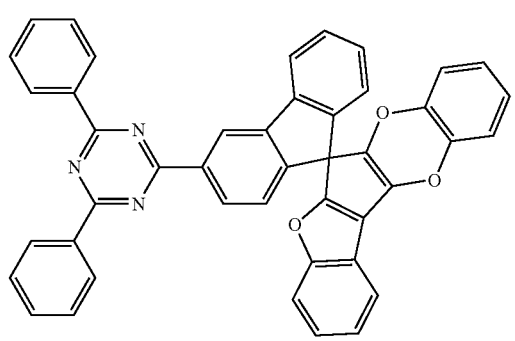
P15 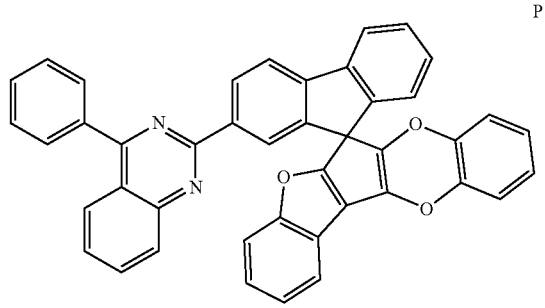
P19 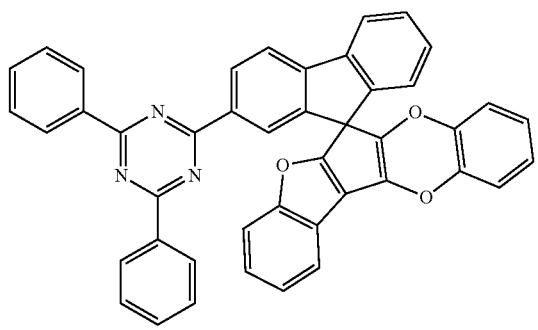
P16 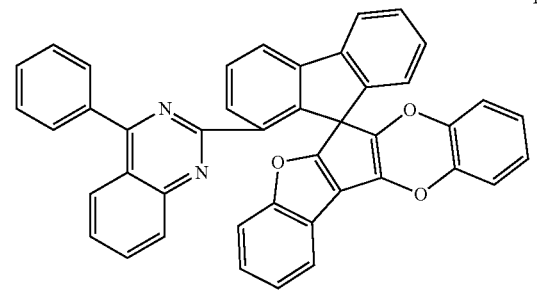
P20 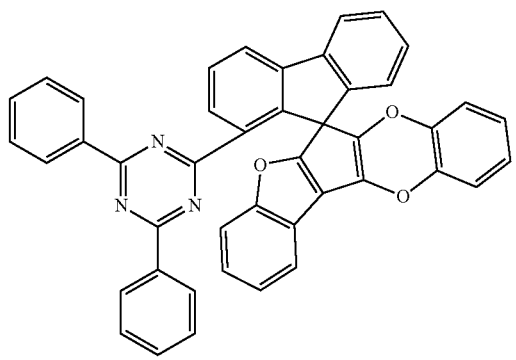

P21
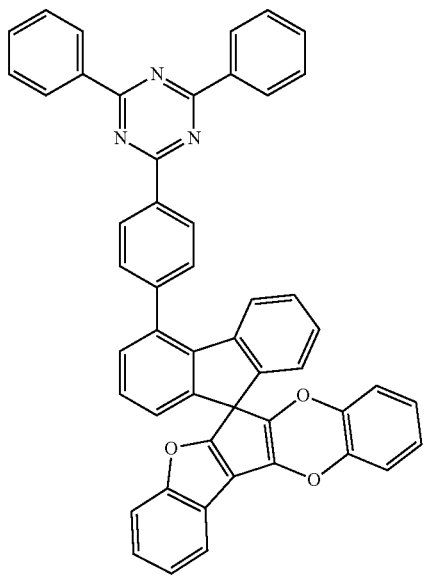
P22
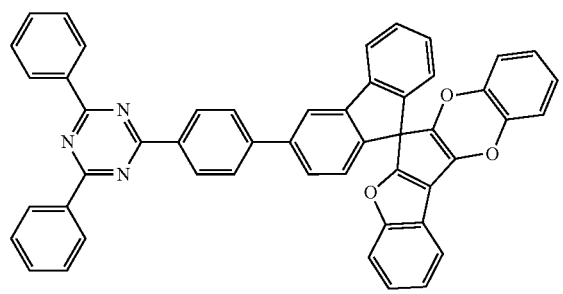
P23
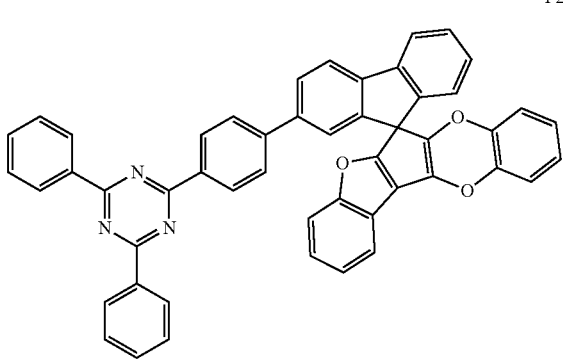
P24
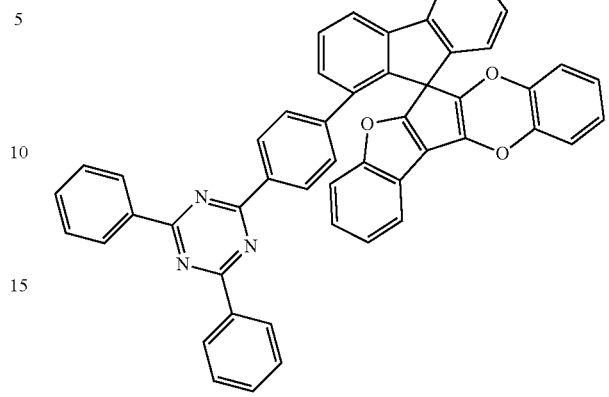
P25
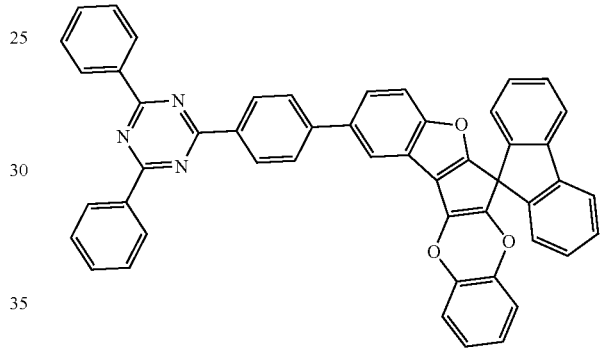
P26
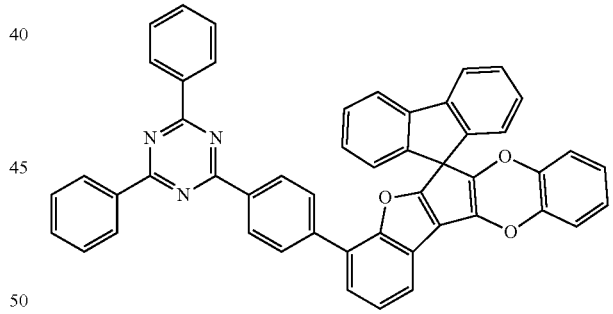
P27
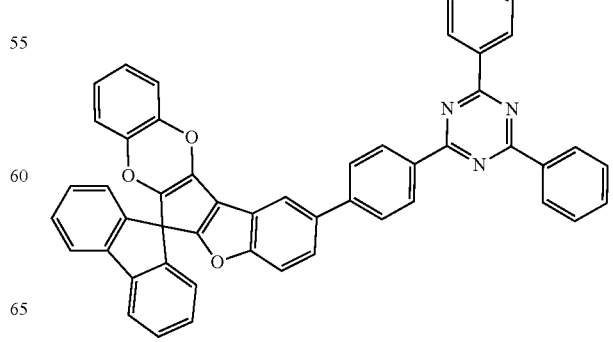

-continued
P28
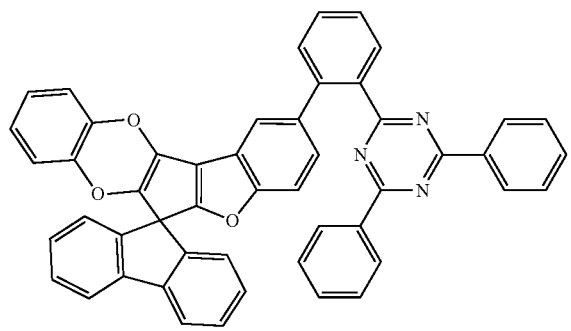
P29
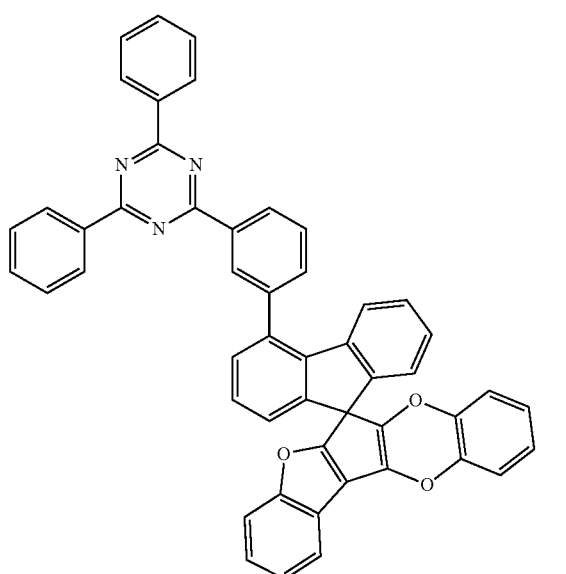
P30
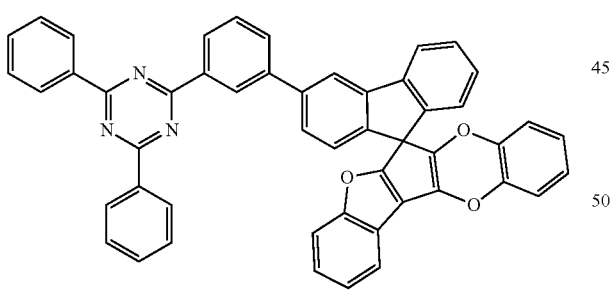
P31
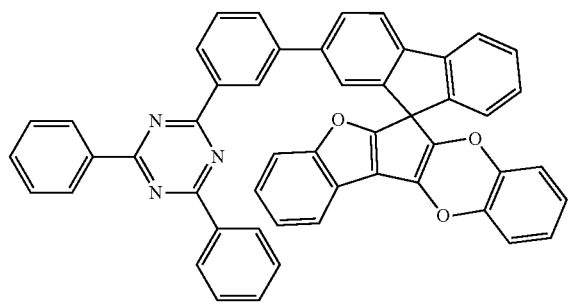
P32
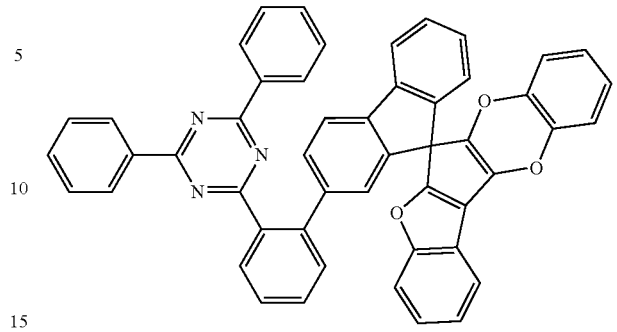
P33
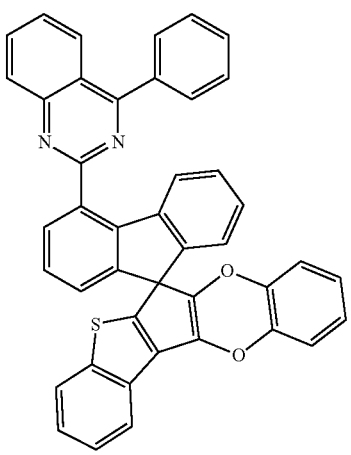
P34
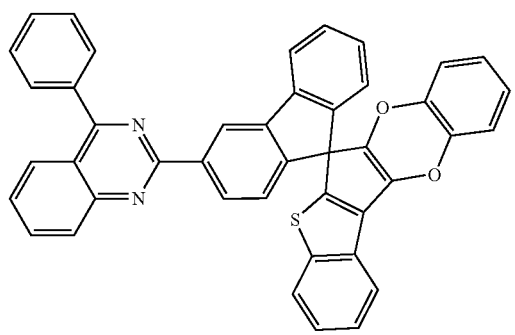
P35
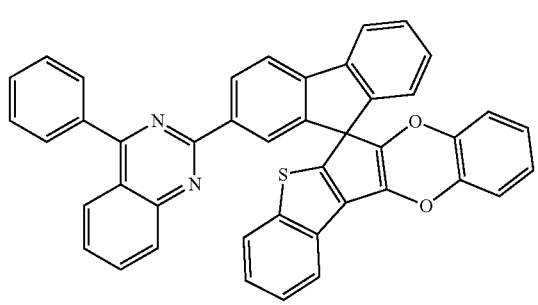

-continued
P36
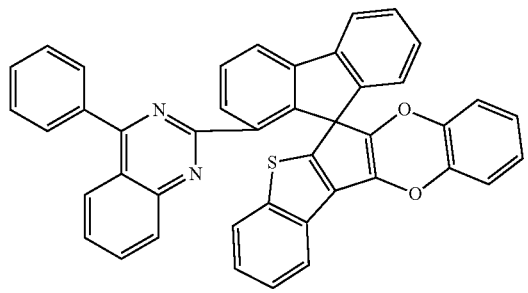
P37
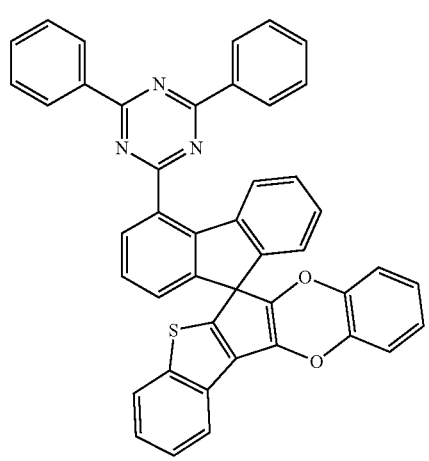
P38
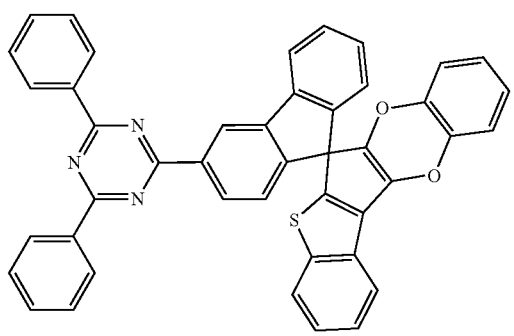
P39
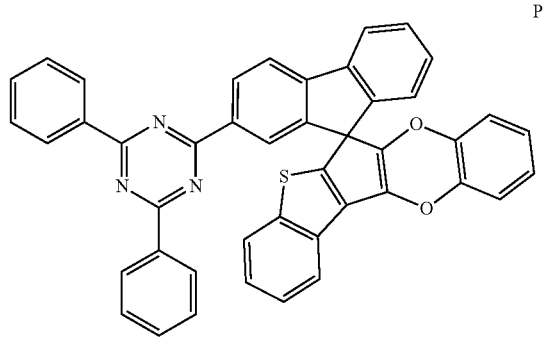
P40
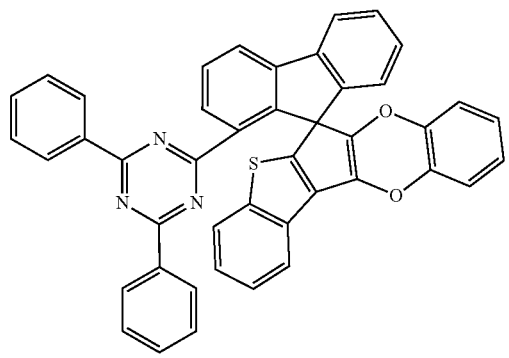
P41
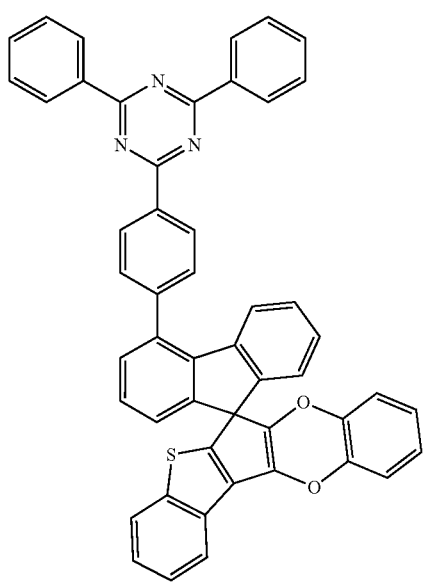
P42
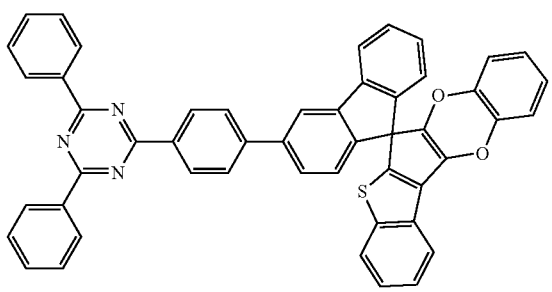
P43
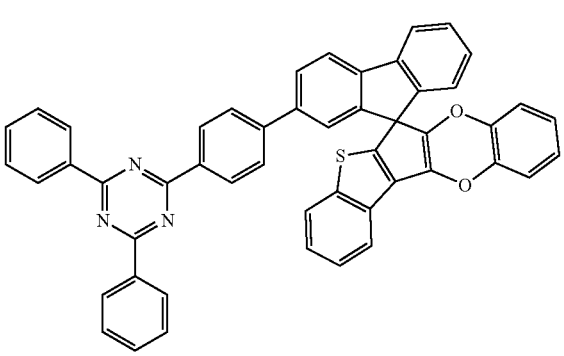

P44
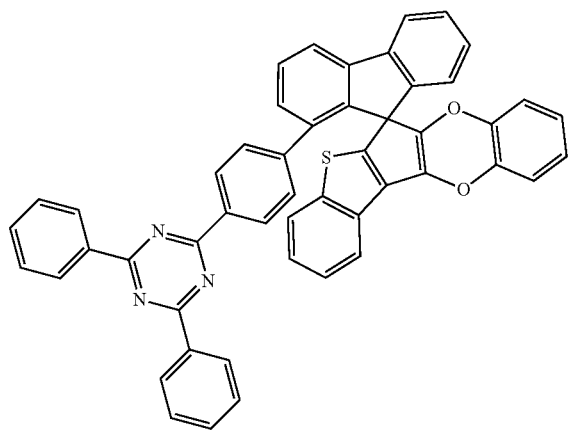
P45
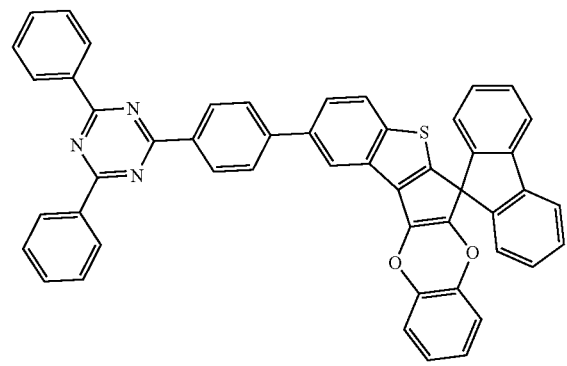
P46
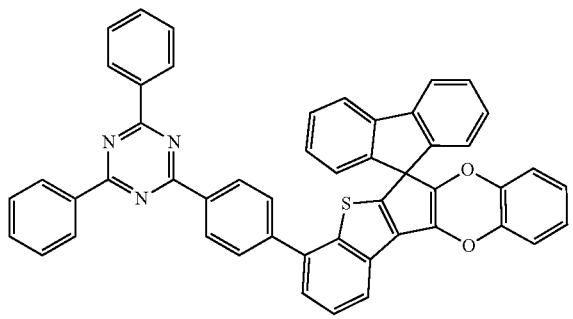
P47
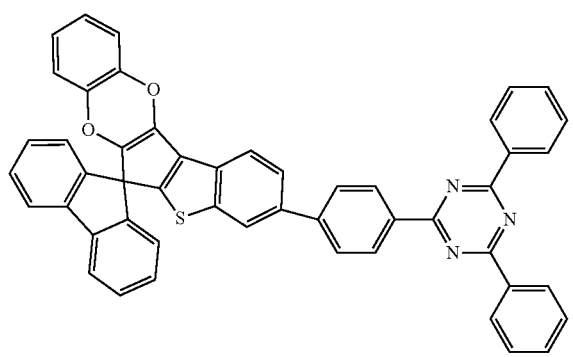
P48
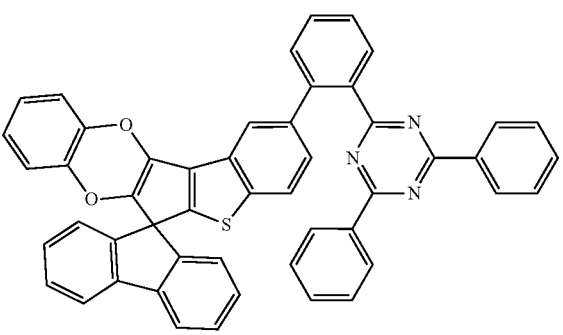
P49
P50
P51
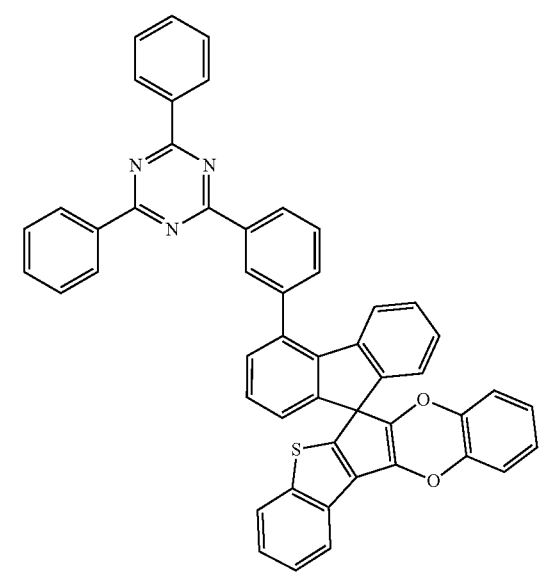
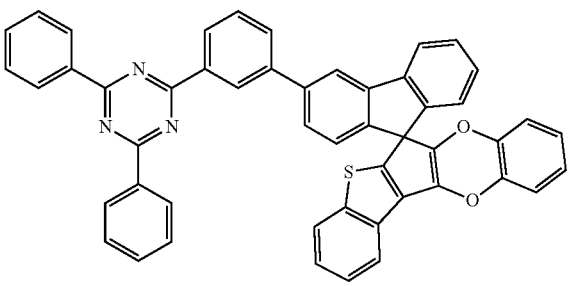

-continued
P52
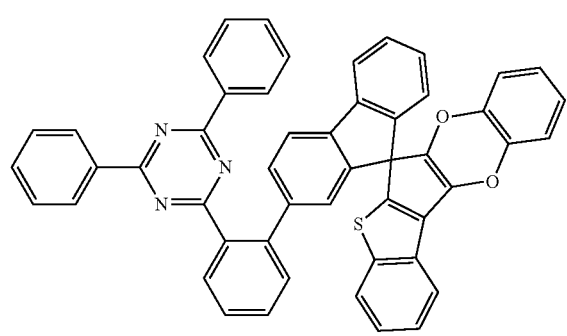
P53
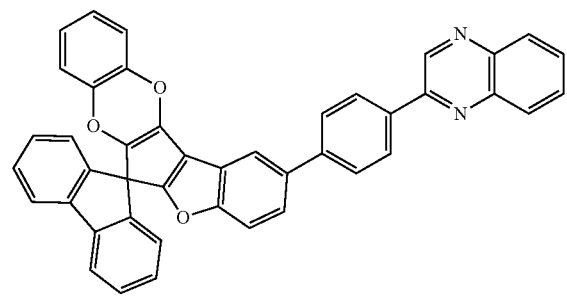
P54
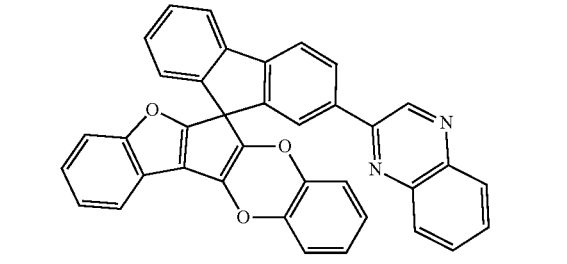
P55
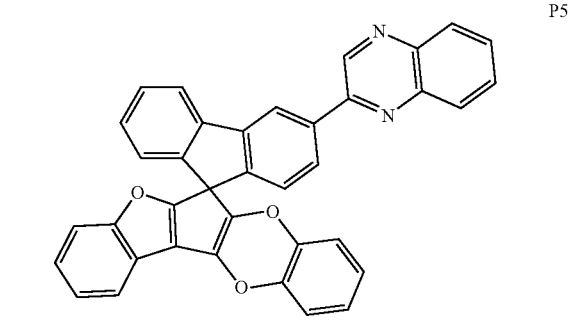
P56
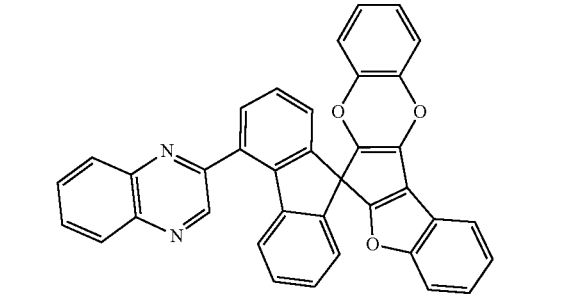
-continued
P57
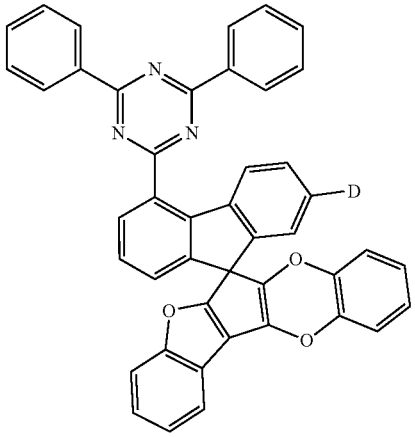
P58
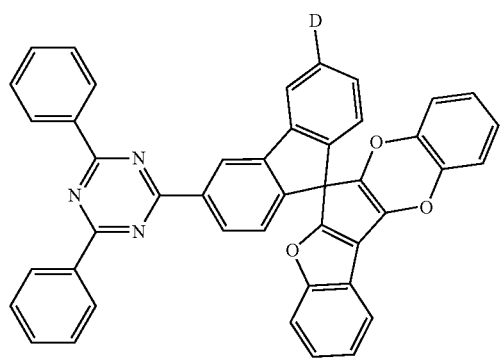
P59
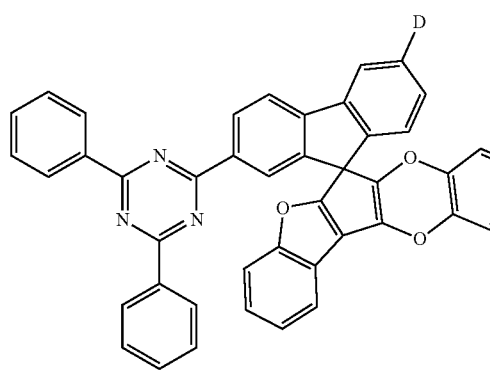
P60
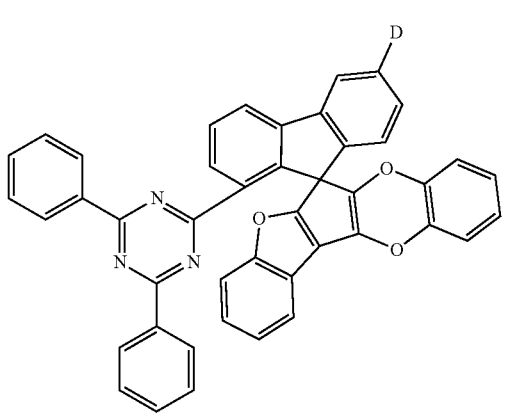

P61
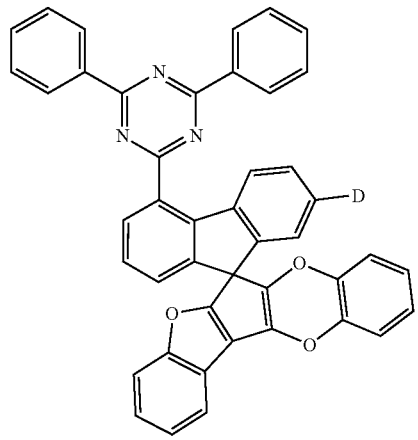
P62
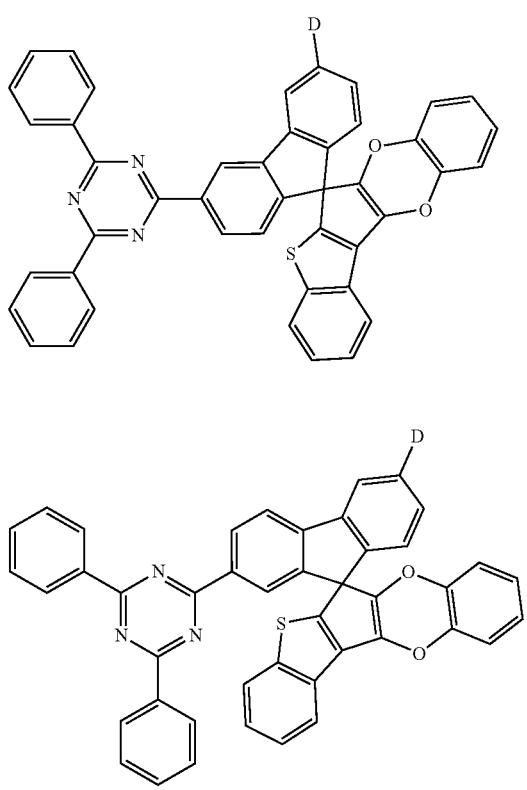
P63
P64
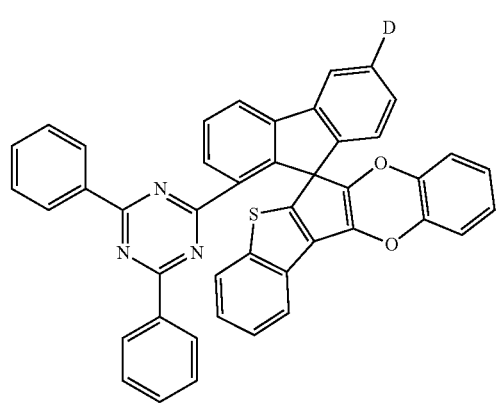
P65
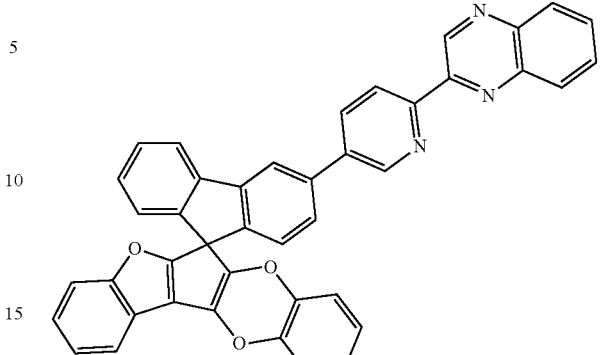
P66
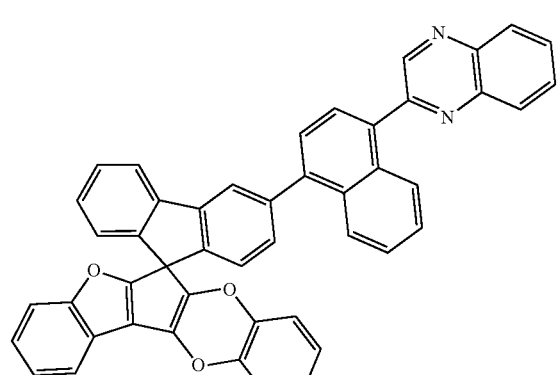
P67

P68
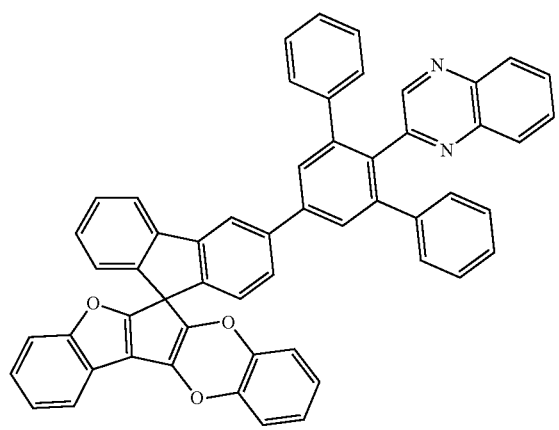
P69
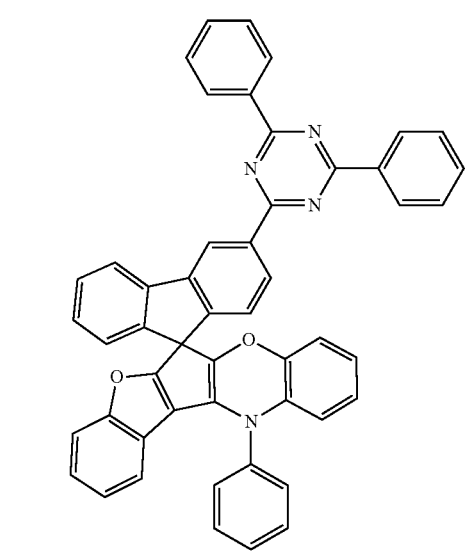
P70
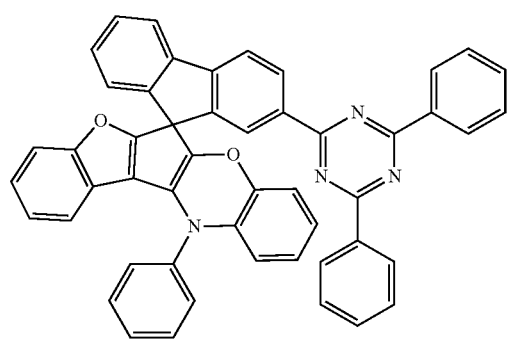
P71
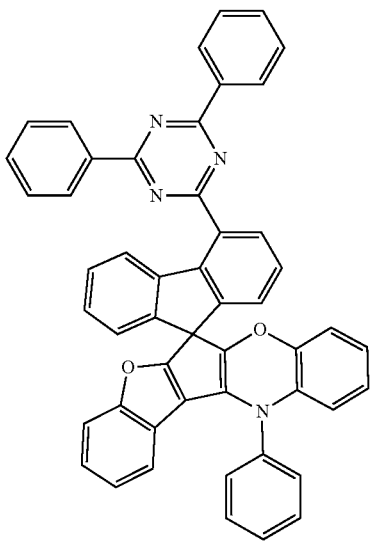
P72
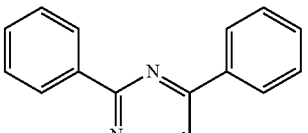
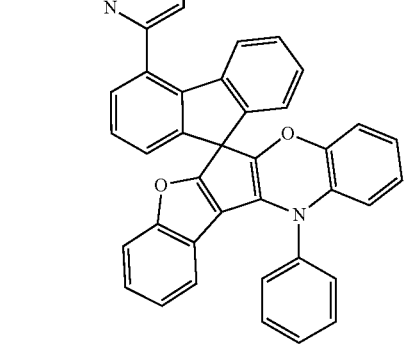
P73
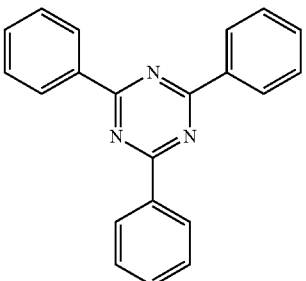
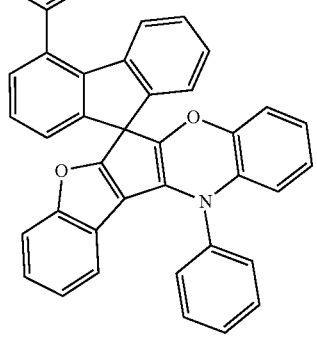

-continued
P74
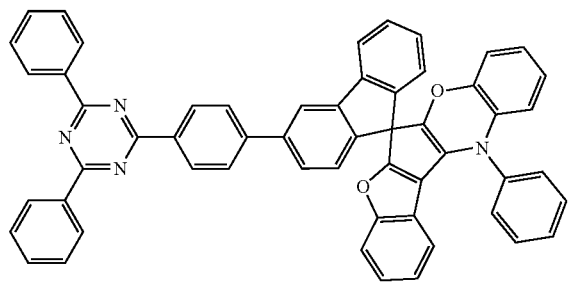
P75
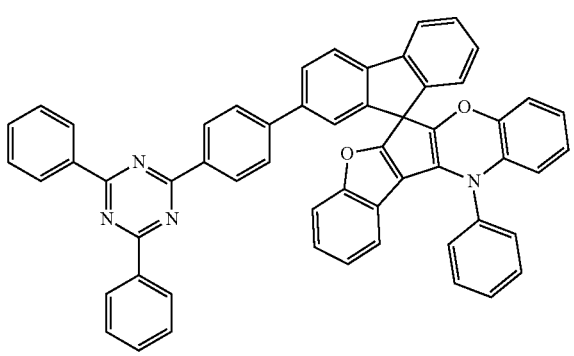
P76
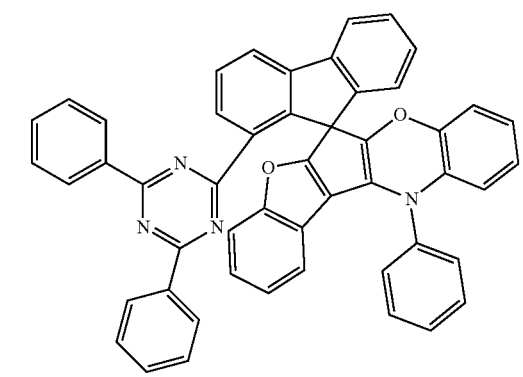
P77
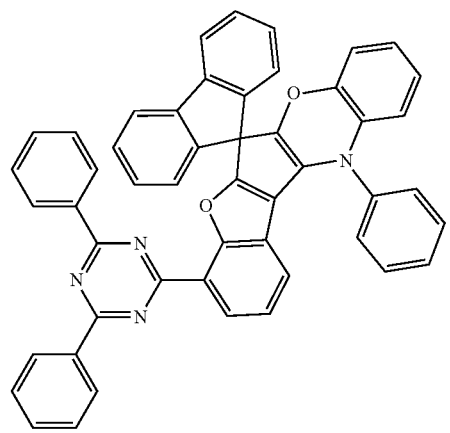
P78
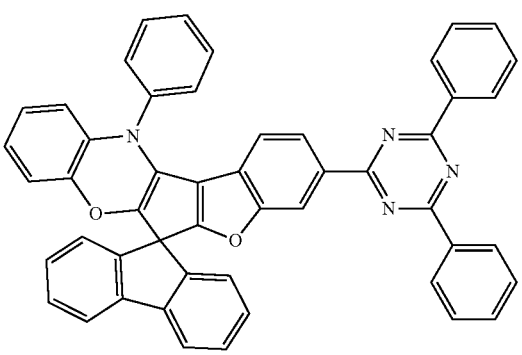
P79
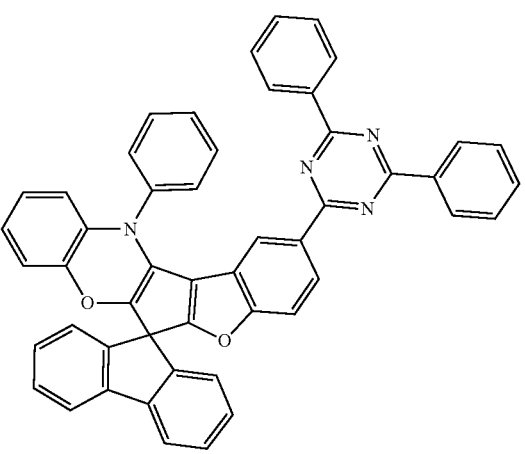
P80
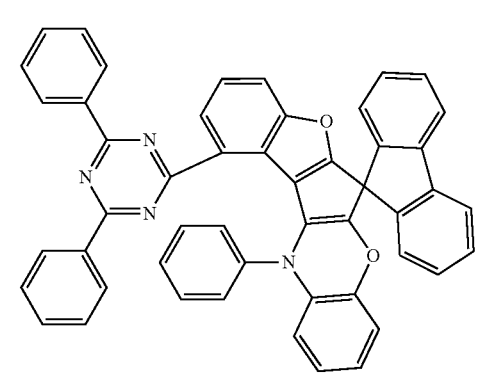
P81
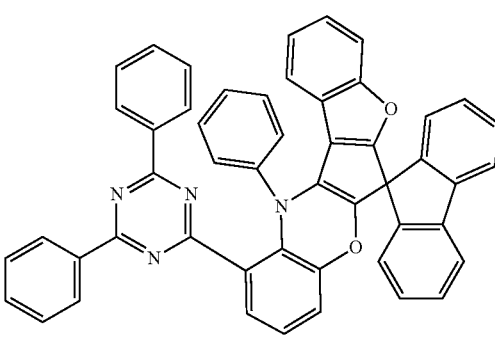

P82
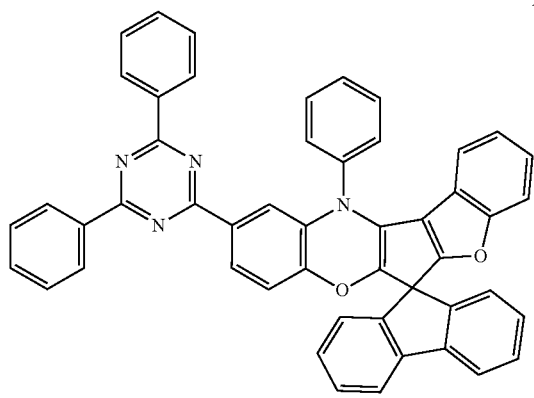
P83
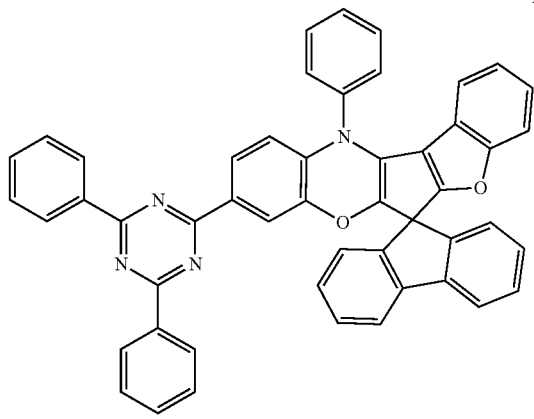
P84
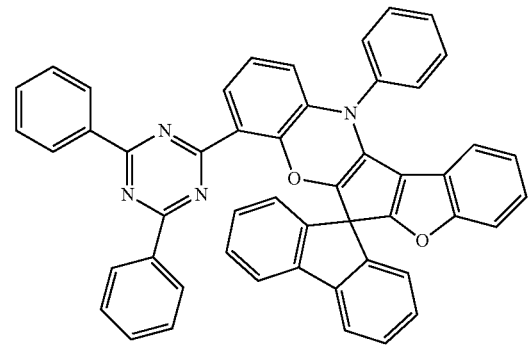
P85
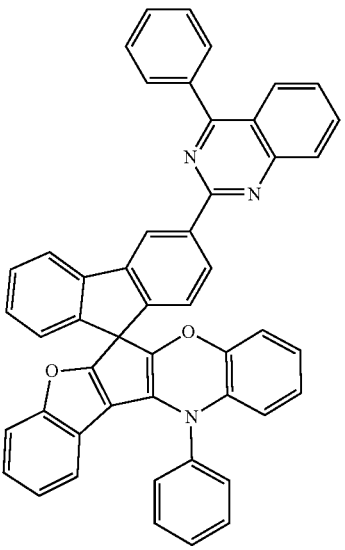
P86
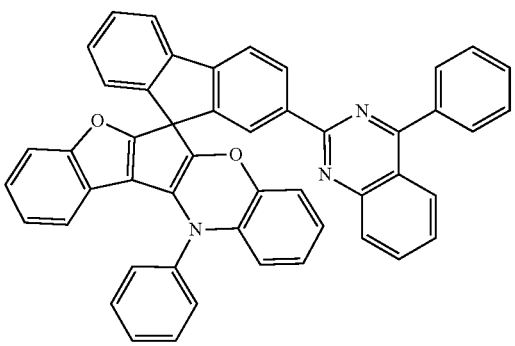
P87
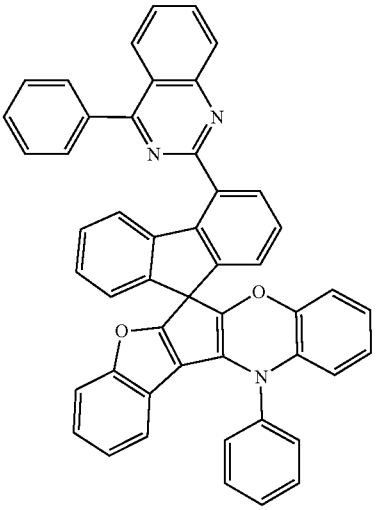

-continued
P88
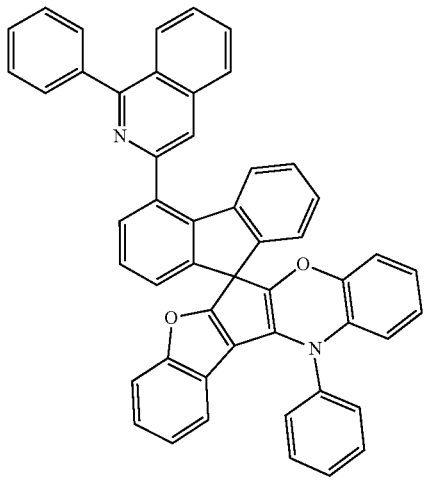
P89
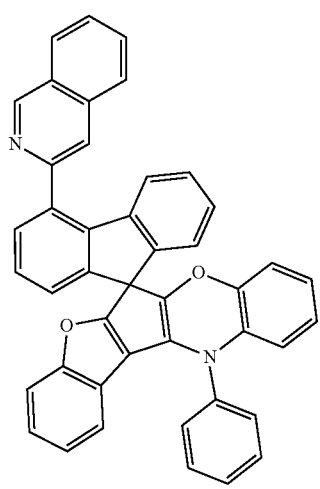
P90
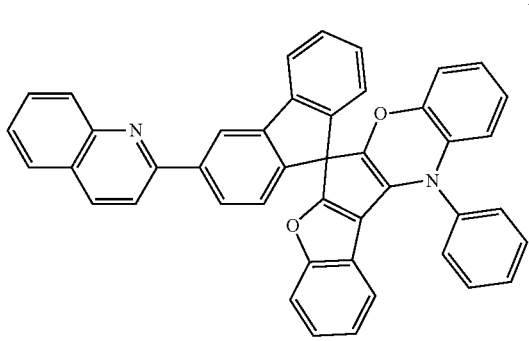
P91
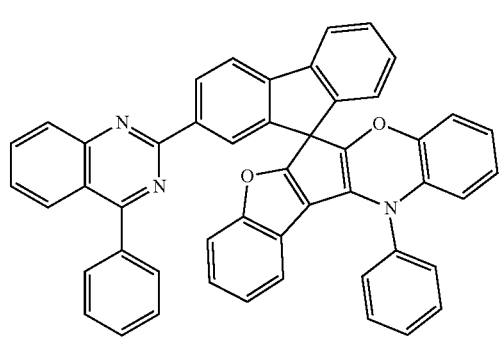
P92
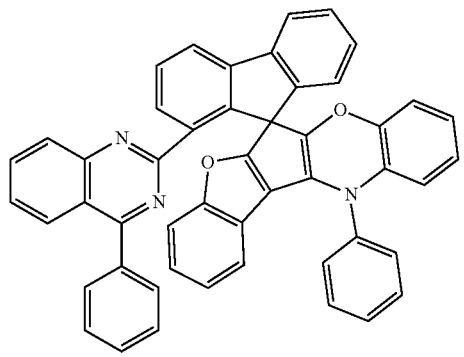
P93
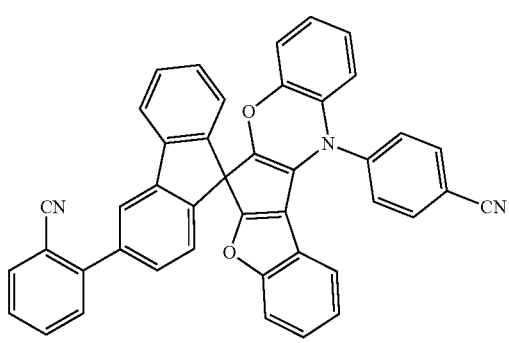
P94
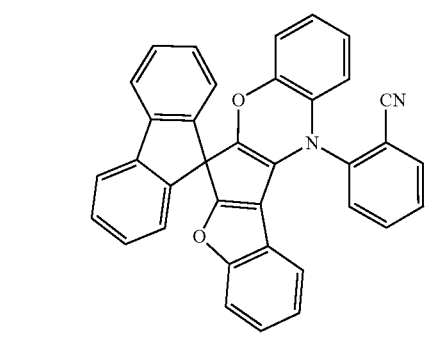
P95
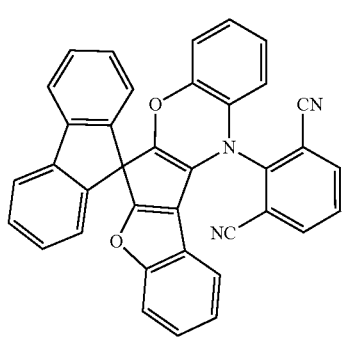

-continued
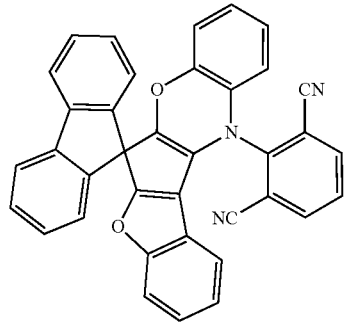
P96
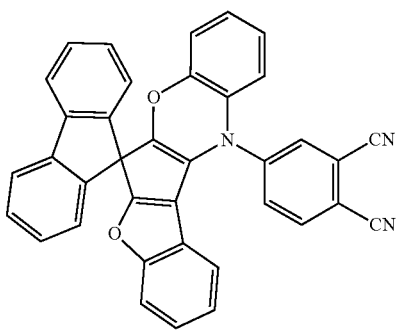
P100
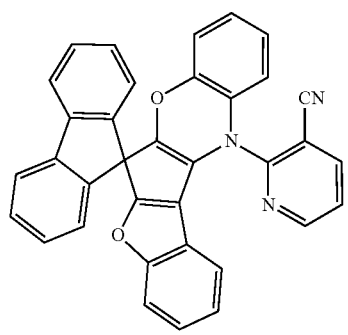
P97
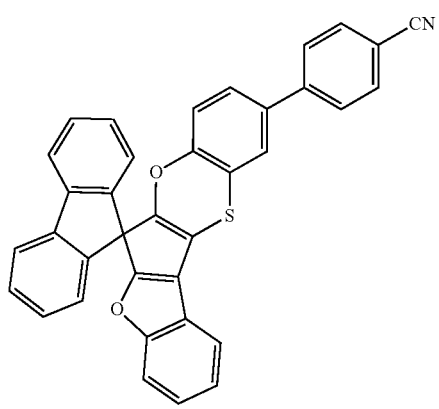
P101
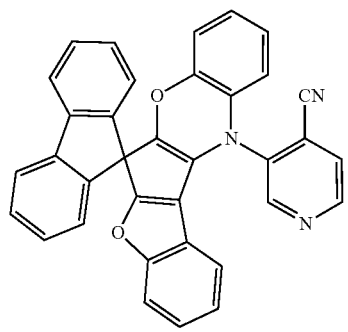
P98
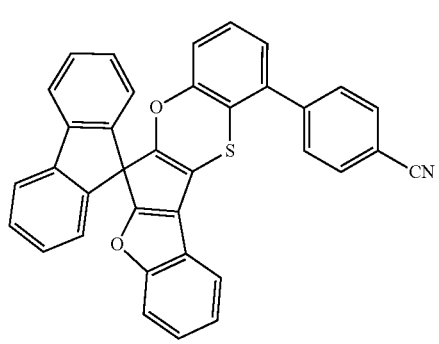
P102
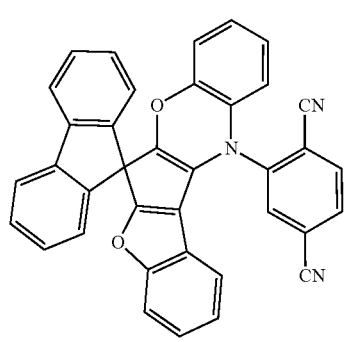
P99
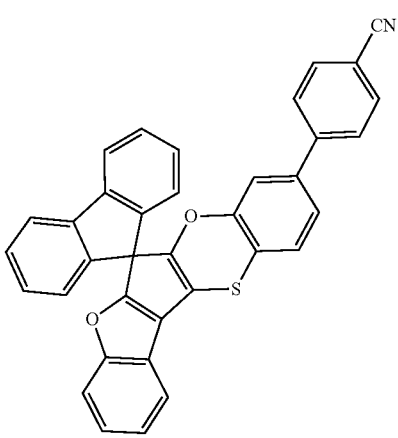
P103

P104
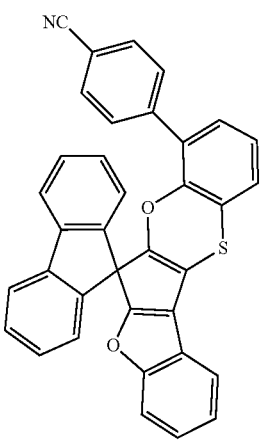
P105
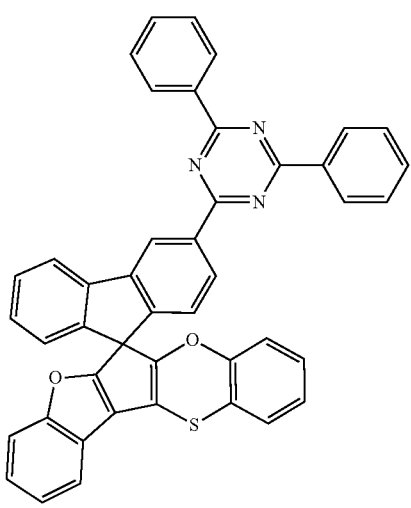
P106
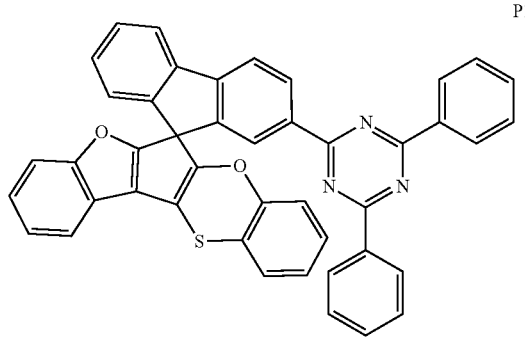
P107
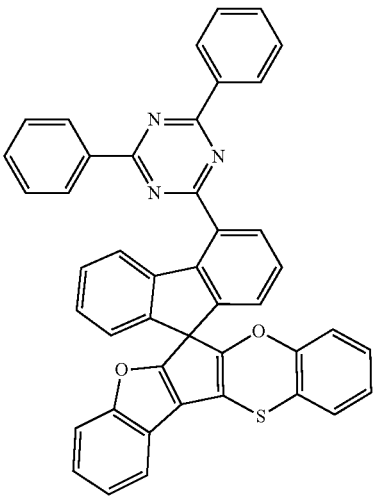
P108
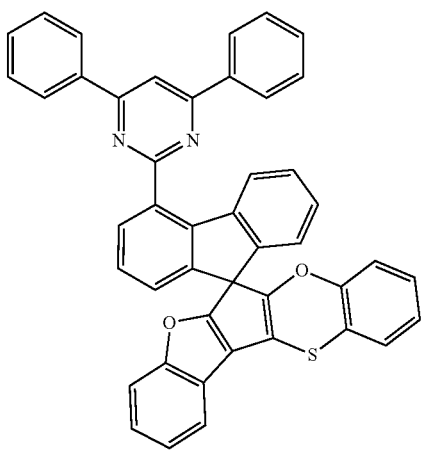
P109
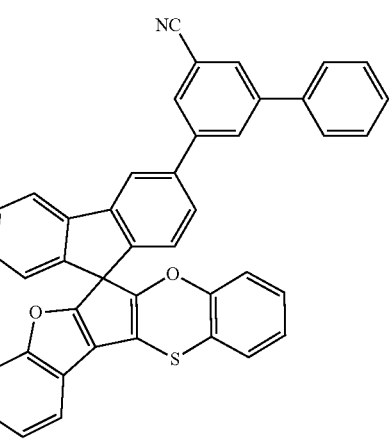

P110
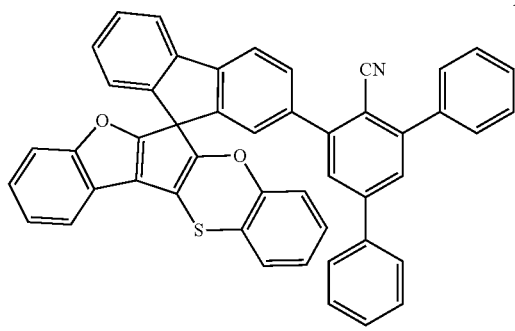
P111
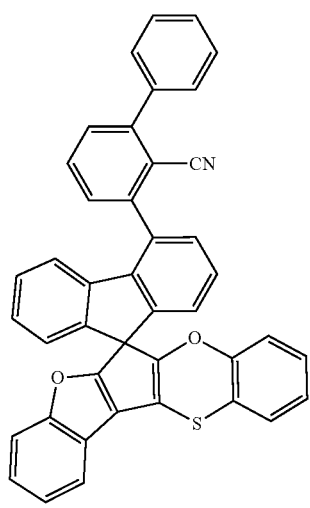
P112
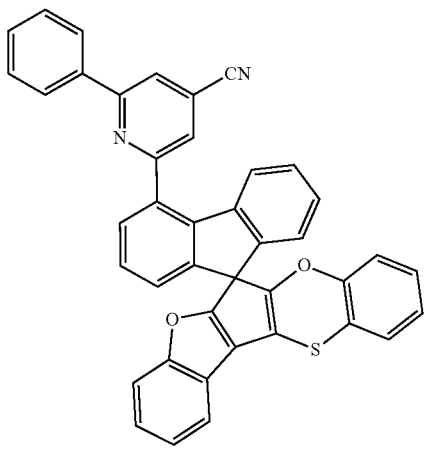
P113
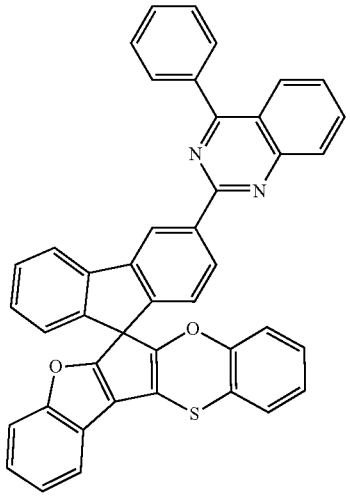
P114
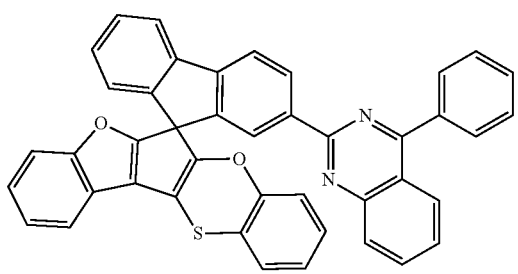
P115
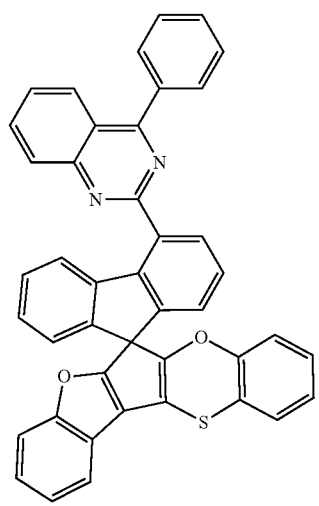

P116 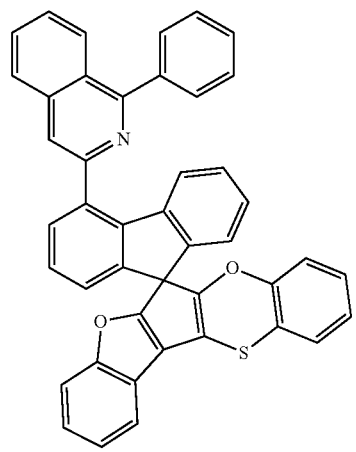
P120 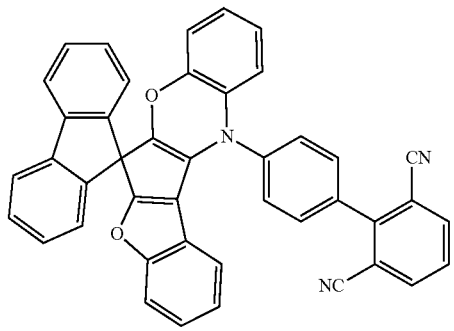
P117 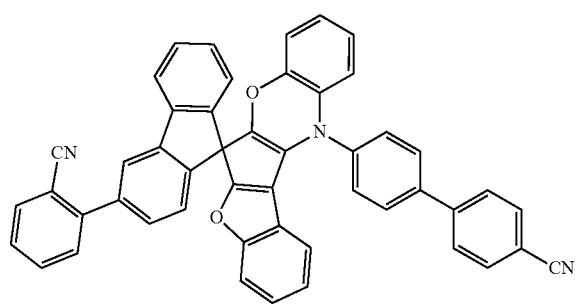
P121 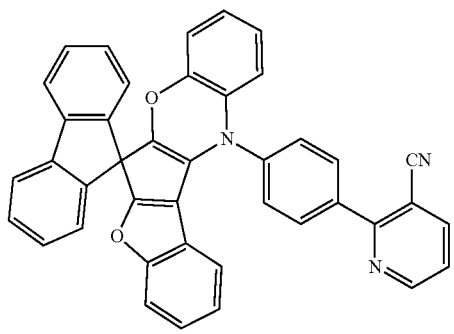
P118 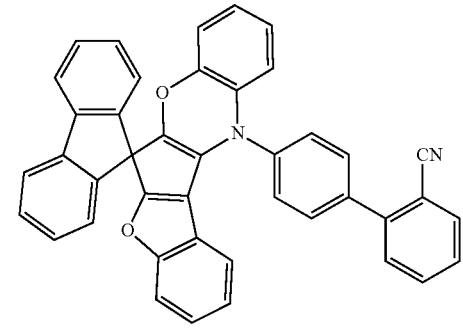
P122 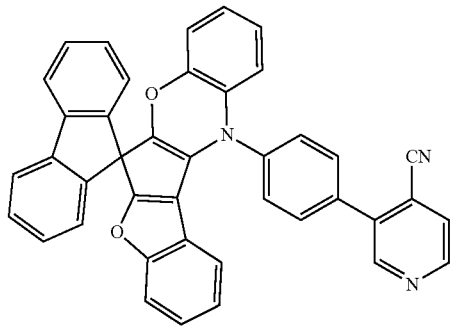
P119 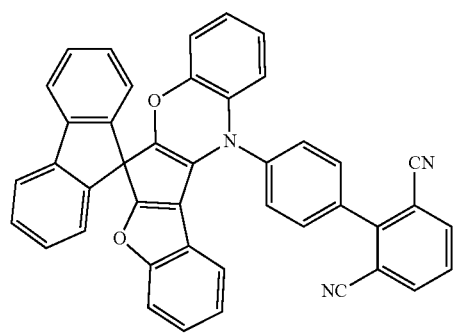
P123 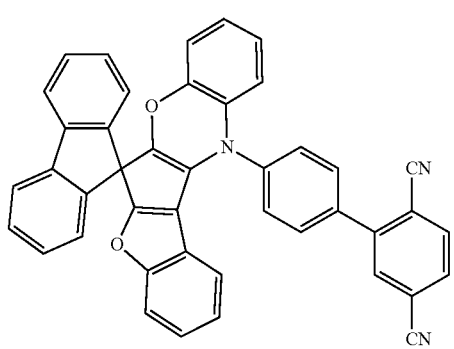

-continued
P124
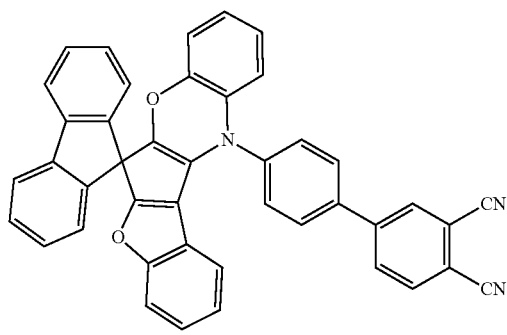
P125
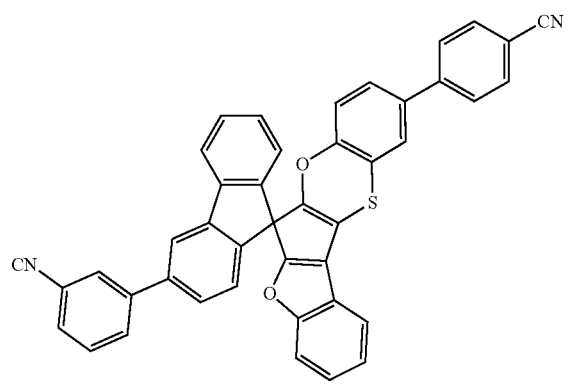
P126
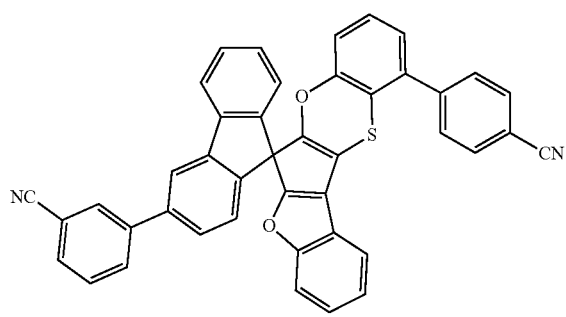
P127
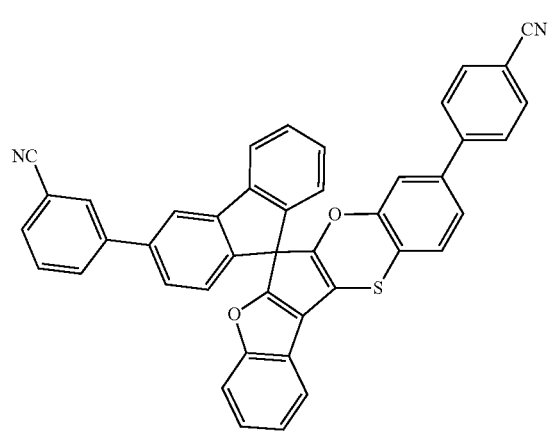
-continued
P128
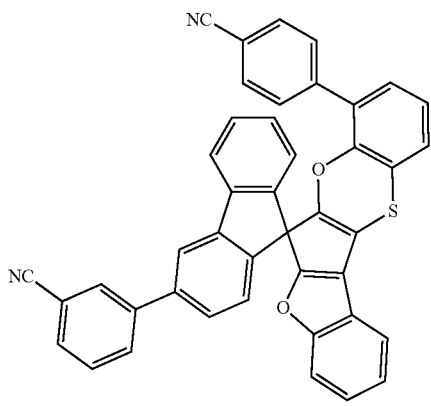
P129
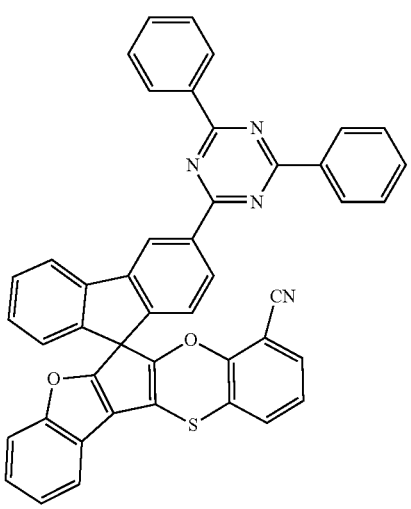
P130
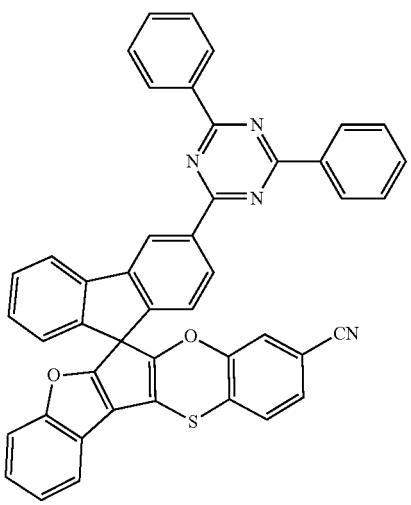

P131 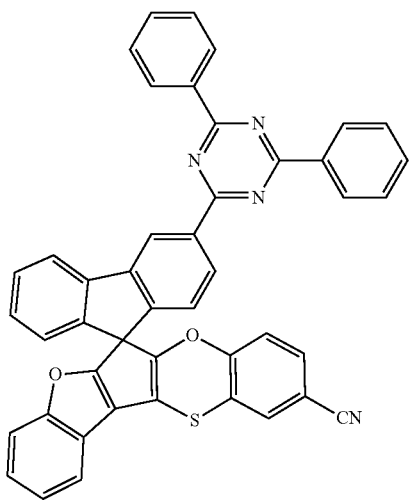

P134 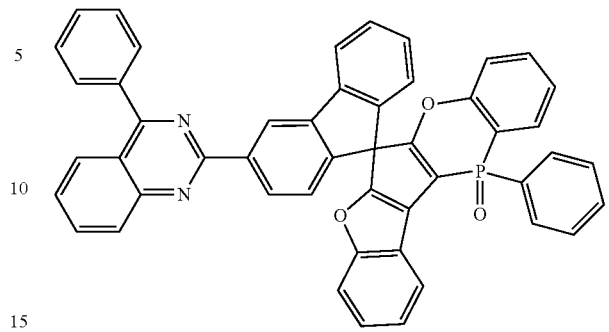

P135 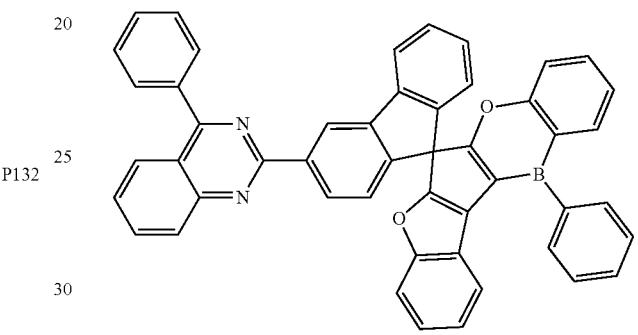

P132 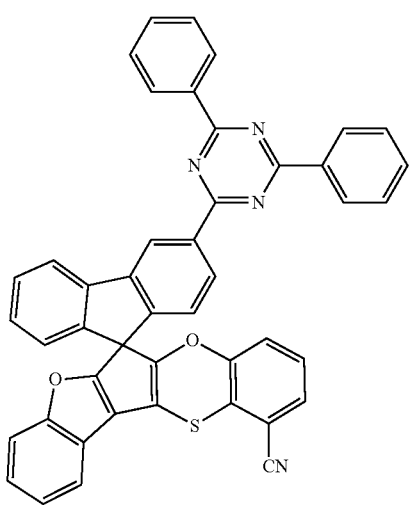

P136 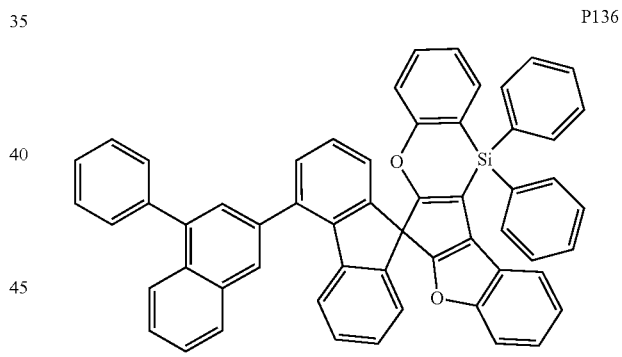

P133 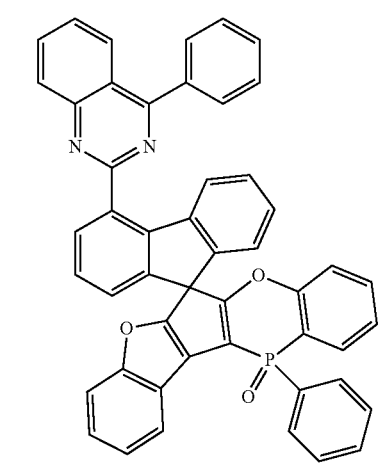

wherein D represents deuterium.

9. An organic electroluminescent material, comprising the organic compound according to claim 1.

10. A light-emitting layer material, comprising the organic compound according to claim 1.

11. An organic light-emitting diode (OLED) device, comprising an anode, a cathode and an organic thin film layer disposed between the anode and the cathode, wherein a material of the organic thin film layer comprises the organic compound according to claim 1.

12. The OLED device according to claim 11, wherein the organic thin film layer comprises a light-emitting layer which comprises a host material and a doped material, wherein the host material comprises the organic compound, wherein the organic compound has a structure represented by Formula I:

Formula I

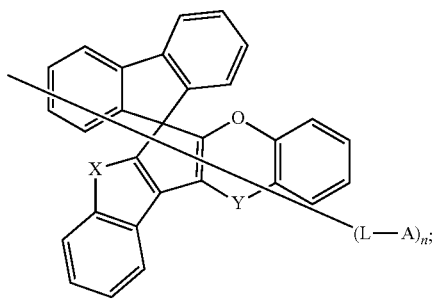

(L—A)$_n$;

wherein L is independently selected from a single bond, substituted or unsubstituted C6 to C30 aryl or substituted or unsubstituted C5 to C30 heteroaryl;

A is independently selected from cyano, substituted or unsubstituted C6 to C40 arylamine or substituted or unsubstituted C5 to C30 heteroaryl;

X and Y are independently selected from O, S,

or M—R, wherein M is N, Si-R or B, and R is C1 to C10 linear or branched alkyl, C1 to C10 alkoxy, C6 to C20 aryl or C6 to C20 arylamino; and n is an integer from 1 to 16.

13. A display panel, comprising the OLED device according to claim 11.

14. An organic light-emitting display device, comprising the display panel according to claim 13.

* * * * *